US011717288B2

(12) United States Patent
Edoga et al.

(10) Patent No.: US 11,717,288 B2
(45) Date of Patent: Aug. 8, 2023

(54) REMOTE SURGICAL SUTURE SYSTEM

(71) Applicant: Vesteck, Inc., West Chester, PA (US)

(72) Inventors: John K. Edoga, New York, NY (US); Thierry Richard, Villiers le Mahieu (FR); Edward Wulfman, Woodinville, WA (US); Kent Stalker, San Marcos, CA (US)

(73) Assignee: Vesteck, Inc., West Chester, PA (US)

( * ) Notice: Subject to any disclaimer, the term of this patent is extended or adjusted under 35 U.S.C. 154(b) by 0 days.

(21) Appl. No.: 17/841,373

(22) Filed: Jun. 15, 2022

(65) Prior Publication Data

US 2022/0313244 A1     Oct. 6, 2022

Related U.S. Application Data

(63) Continuation of application No. PCT/US2021/048888, filed on Sep. 2, 2021.

(60) Provisional application No. 62/706,682, filed on Sep. 2, 2020.

(51) Int. Cl.
*A61B 17/068* (2006.01)
*A61B 17/064* (2006.01)

(52) U.S. Cl.
CPC ...... *A61B 17/0682* (2013.01); *A61B 17/0644* (2013.01); *A61B 2017/0641* (2013.01)

(58) Field of Classification Search
None
See application file for complete search history.

(56) References Cited

U.S. PATENT DOCUMENTS

| 7,954,688 | B2 | 6/2011 | Argentine et al. |
| 8,157,146 | B2 | 4/2012 | Edoga et al. |
| 8,627,992 | B2 | 1/2014 | Edoga et al. |
| 9,179,915 | B2 | 11/2015 | Edoga et al. |
| 2003/0033006 | A1 | 2/2003 | Phillips et al. |
| 2010/0044410 | A1* | 2/2010 | Argentine ............ A61B 17/11 227/179.1 |
| 2011/0077672 | A1 | 3/2011 | Fleischman et al. |

(Continued)

FOREIGN PATENT DOCUMENTS

| EP | 2 877 106 A1 | 6/2015 |
| WO | WO 2014/018954 A1 | 1/2014 |

OTHER PUBLICATIONS

International Search Report and Written Opinion dated Feb. 4, 2022 for International Application No. PCT/US2021/048888, 18 pages.

*Primary Examiner* — Shaun L David
(74) *Attorney, Agent, or Firm* — Cooley LLP

(57) ABSTRACT

Systems, devices and methods described herein relate to endovascular devices for delivering sutures for securing grafts or other objects to patient vessels. In some embodiments, a suture includes a set of two legs having proximal ends joined to each other and elongate bodies that extend parallel to one another such that the set of two legs form a U-shaped structure. A suture delivery system can include a housing configured to contain a suture in a flattened configuration, and a deployment element having a ribbon-shaped distal portion disposed in the housing and including a set of formations, where the housing and the set of formations of the deployment element are configured to collectively constrain the suture in the flattened configuration until the suture is released through the opening of the housing.

28 Claims, 33 Drawing Sheets

(56) References Cited

U.S. PATENT DOCUMENTS

2012/0277853 A1 11/2012 Rothstein
2015/0201947 A1\* 7/2015 Hill .................... A61B 17/1227
606/157

\* cited by examiner

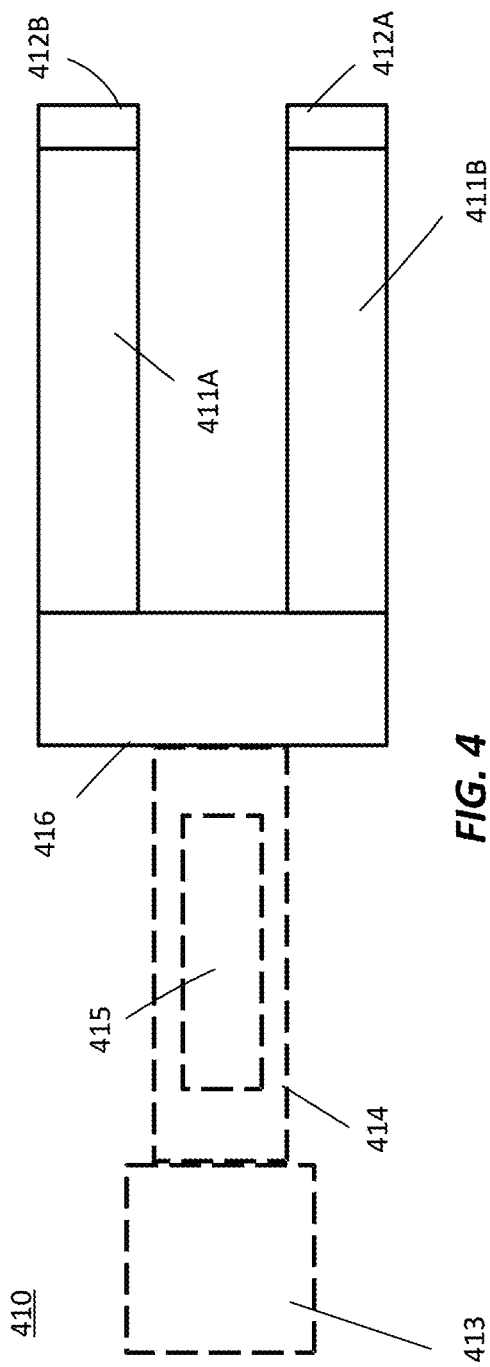
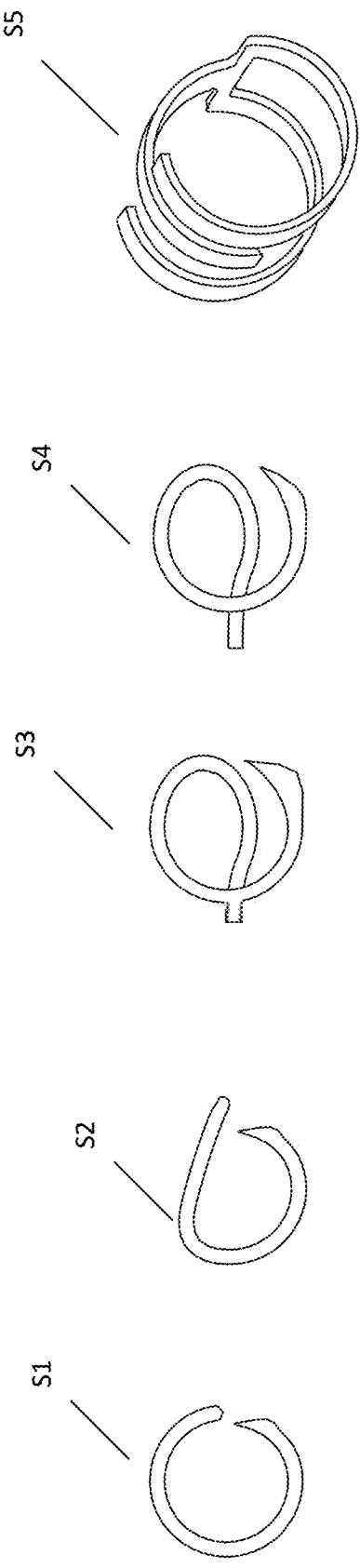
FIG. 4
FIG. 5A  FIG. 5B  FIG. 5C  FIG. 5D  FIG. 5E

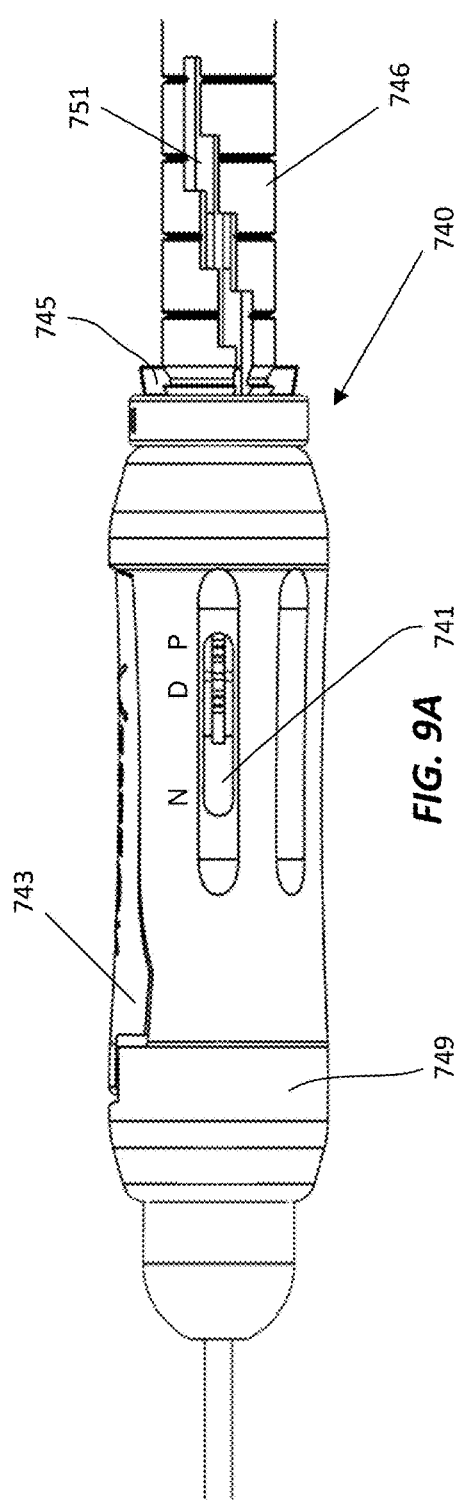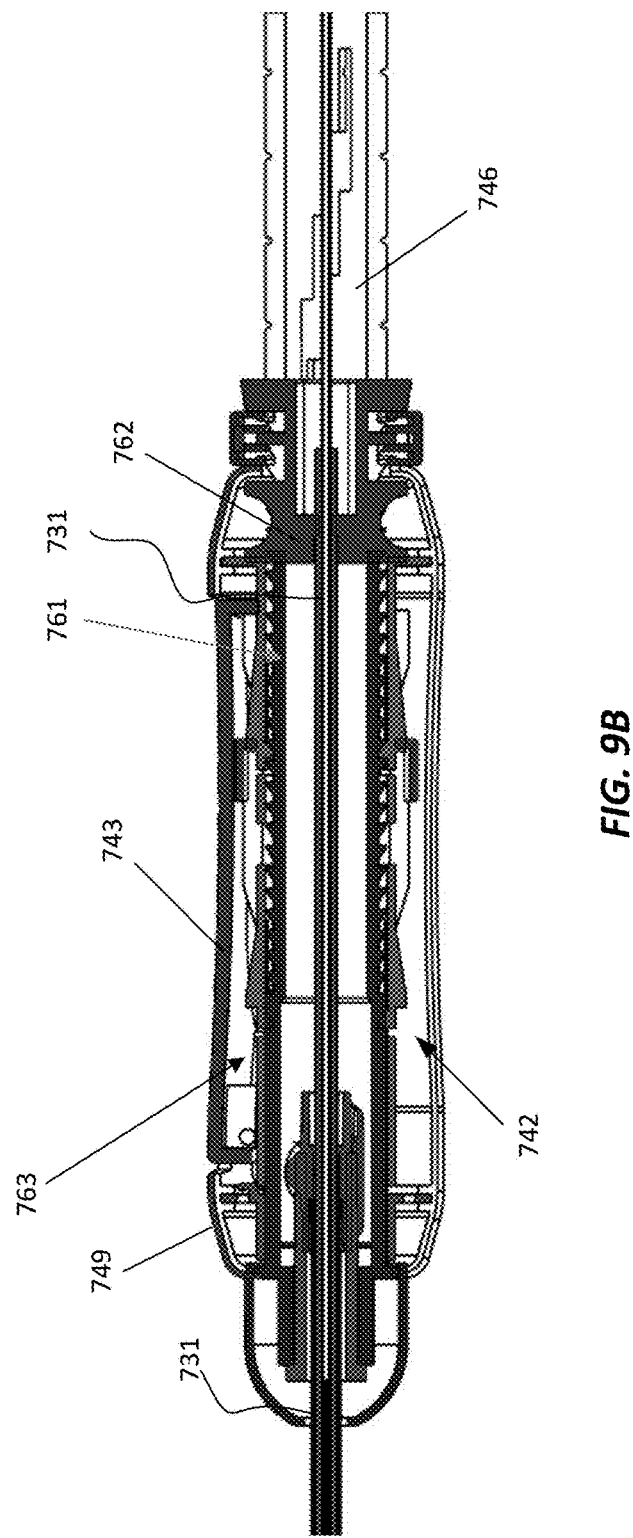
FIG. 9A
FIG. 9B

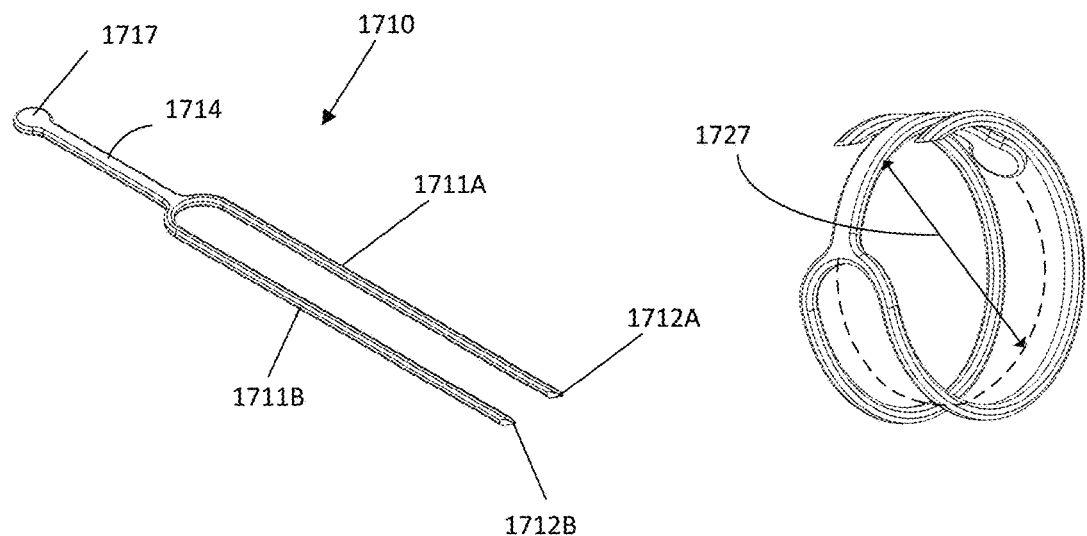
FIG. 17A
FIG. 17B
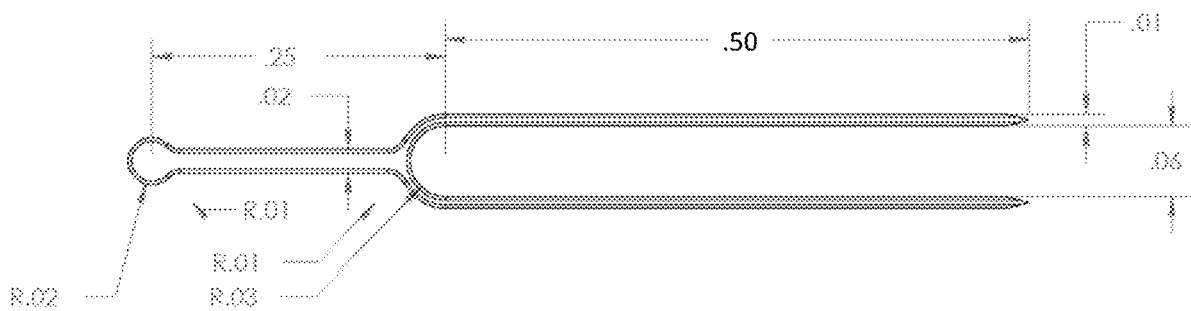
FIG. 17C

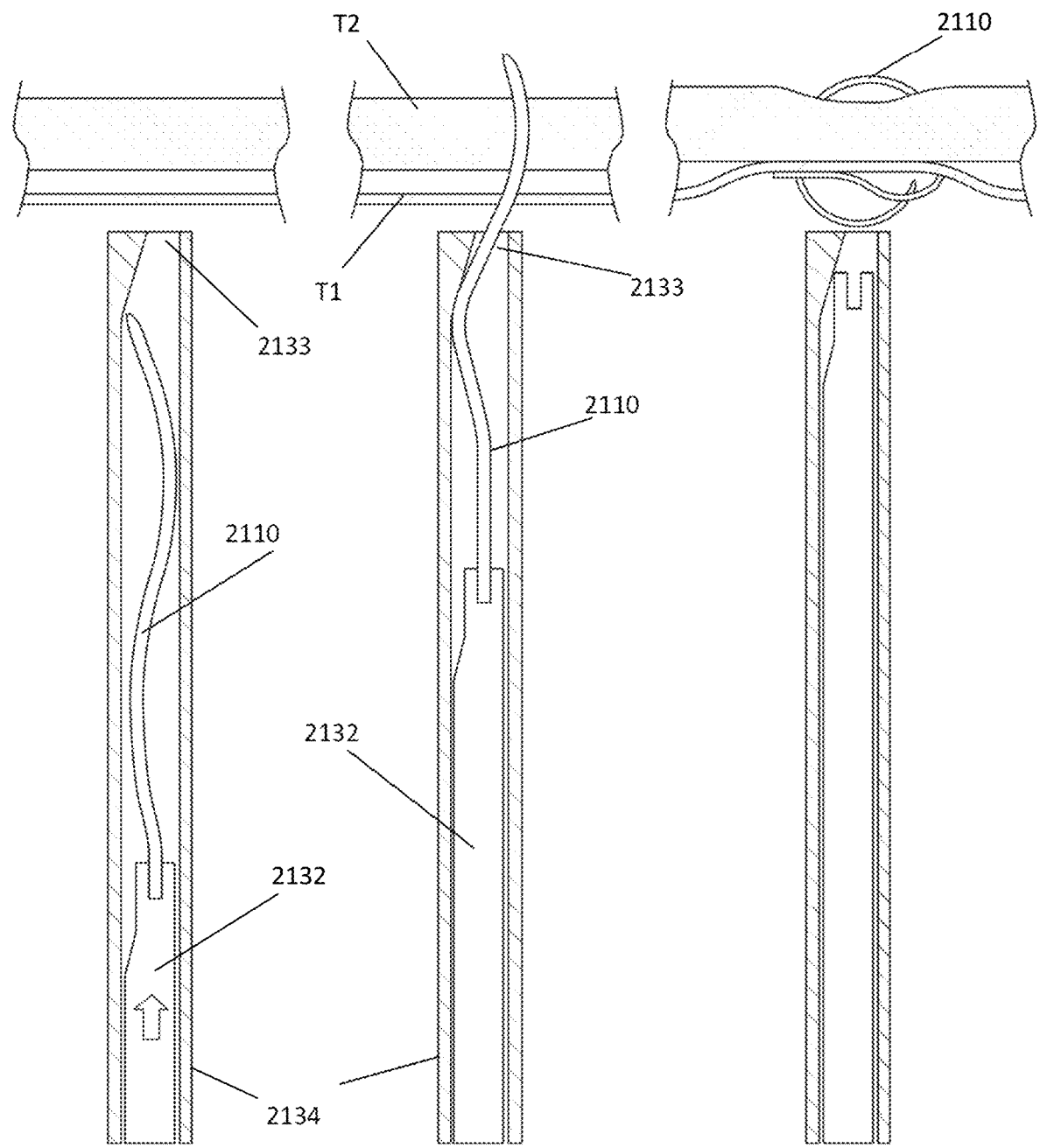
FIG. 21A  FIG. 21B  FIG. 21C

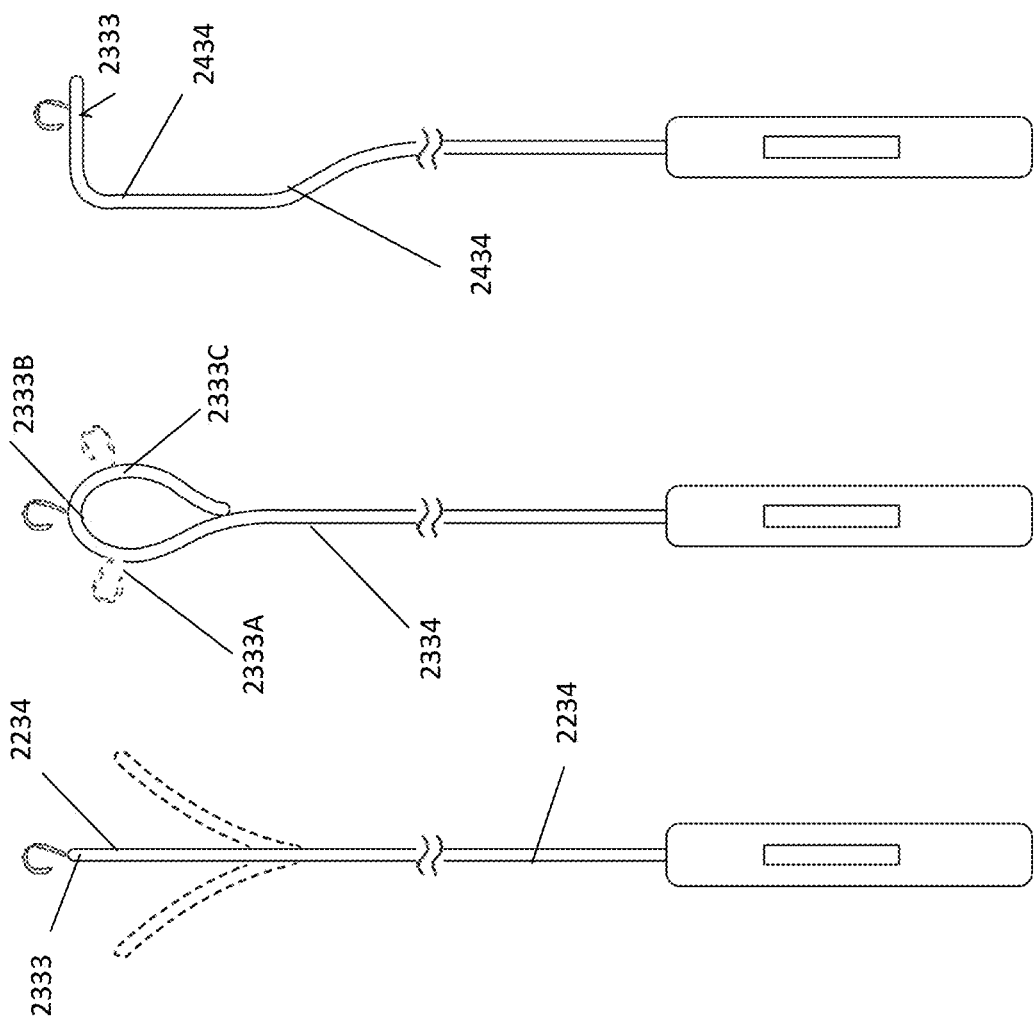

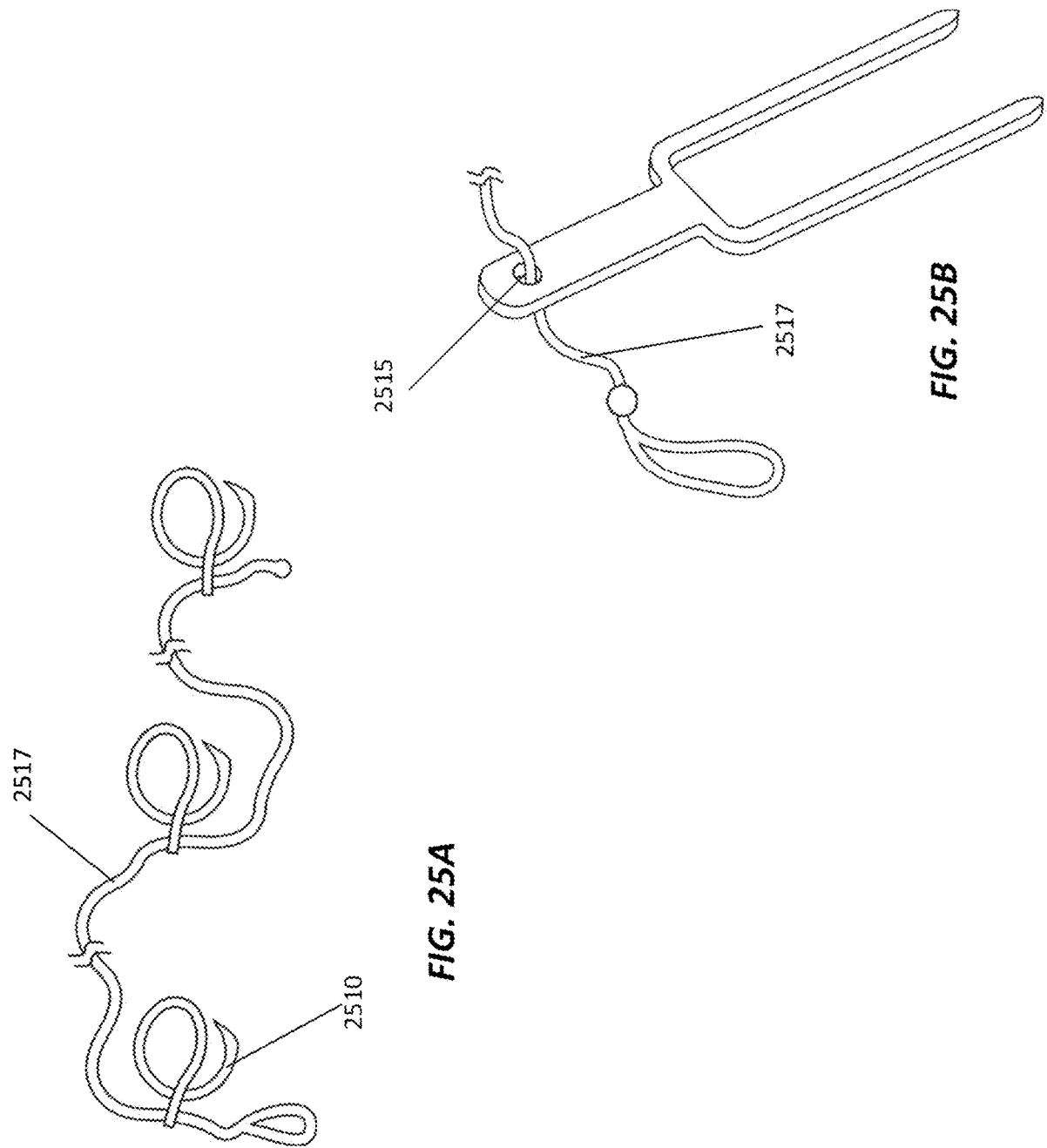

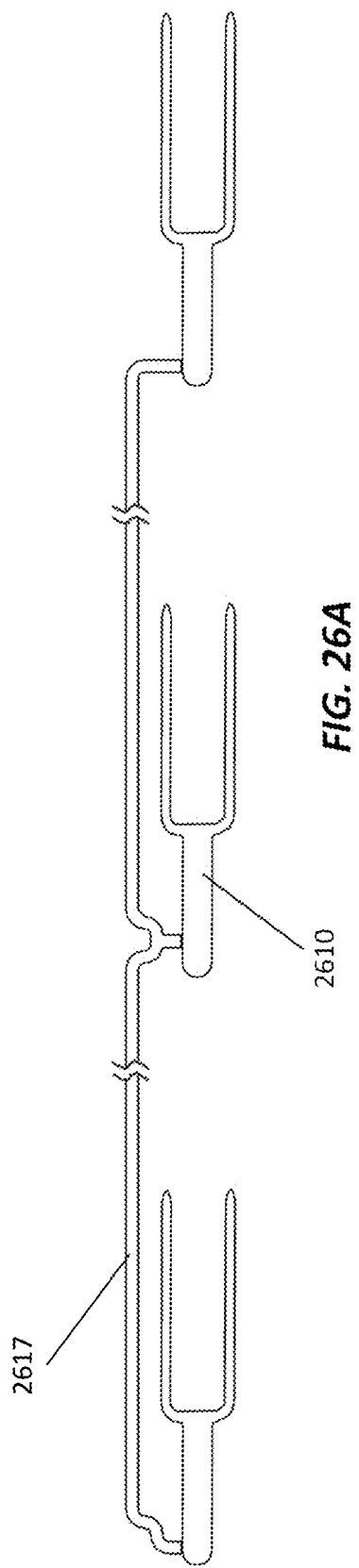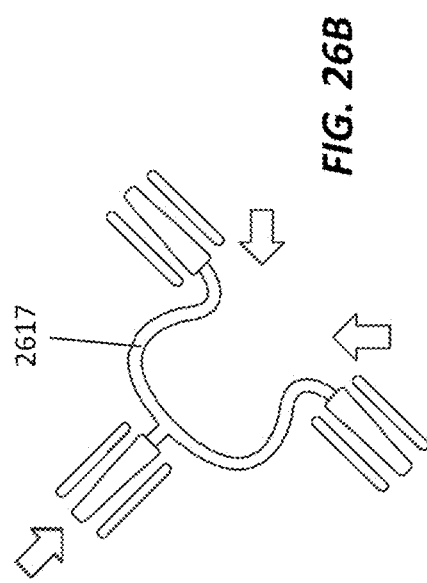

REMOTE SURGICAL SUTURE SYSTEM

CROSS-REFERENCE TO RELATED APPLICATIONS

This application is a continuation of International Patent Application No. PCT/US2021/048888, entitled "Remote Surgical Suture System," filed Sep. 2, 2021, which claims priority to U.S. Provisional Patent Application No. 62/706,682, entitled "Remote Surgical Suture System," filed on Sep. 2, 2020, the disclosures of which are incorporated by reference herein in their entireties.

TECHNICAL FIELD

The present disclosure generally relates to endovascular devices and methods thereof, and in particular to endovascular suture delivery systems and methods of treating vascular disease.

BACKGROUND

Remote surgical and interventional procedures are often done to avoid the trauma and potential complications of open surgery. An example is percutaneously placed grafts for treatment of abdominal aortic aneurysms (AAA), or AAA endovascular repair, which can avoid the major trauma of open surgical aortic repair. Remote surgery and interventional procedures can be done on major organs including heart, liver, kidneys, and the like. Other examples of minimally invasive or remote surgery include minimally invasive gastrointestinal and musculoskeletal surgeries.

Open surgery, however, can provide better long-term outcomes, partly because surgeons can use sutures in a secure manner to attach grafts and other materials to patient vessels to achieve a desired long-term result. Remote surgical and interventional procedures may not be able to achieve placement of sutures in a manner that mimics the secure sutures surgeons place when performing open surgery. The AAA grafts mentioned above are an example where surgically tied sutures ensure the graft and the aorta do not move relative to another as the patient ages and the body changes. Complications from endovascular grafts which are not, typically sutured in place can include endovascular leaks, increased risk of aneurysm failures, and the like. Similar examples exist for minimally invasive remote surgery as compared to open surgery in other areas of the body such as those listed above, oftentimes for the same reason of not being able to place secure sutures.

Some examples exist of devices that intend to hold a graft in place. One example is an anchoring mechanism that can be delivered percutaneously to a location of a graft and used to anchor the graft to a wall of the aorta. For example, U.S. Pat. No. 8,157,146, titled "Stapling Device," issued Apr. 17, 2012, and U.S. Pat. No. 8,627,992, titled "Endovascular Stapler," issued Jan. 14, 2014, describe examples of staple delivery devices for delivering staples for fixation with a graft and aorta. Such devices, however, can be limited in their ability to deliver multiple anchoring mechanisms or staples and in delivering anchoring mechanisms or staples that clamp the graft and the aorta together to prevent the mechanisms from backing out.

Thus, there is a need for systems, devices, and methods that can be placed in a percutaneous procedure, that can securely hold and clamp, and can deliver multiple sutures.

SUMMARY

Systems, devices and methods described herein relate to endovascular devices for delivering sutures for securing grafts or other objects to patient vessels. In some embodiments, a suture includes: a set of two legs having proximal ends joined to each other and elongate bodies that extend parallel to one another such that the set of two legs form a U-shaped structure, the set of legs having distal ends that terminate in sharpened tips that are configured to penetrate through a portion of a graft and a vessel wall adjacent to the portion of the graft; a tail coupled to the U-shaped structure, the suture configured to transition from a flattened configuration in which the tail extends in a direction opposite to the direction of the elongate bodies of the two legs to a curved configuration in which the tail and the set of two legs are curved, the set of legs and the tail configured to exert forces in opposite directions when the suture is in the curved configuration such that the set of legs and the tail are configured to hold the portion of the graft and the vessel wall relative to one another.

In some embodiments, a suture delivery system, includes: a housing configured to contain a suture in a flattened configuration, the housing defining an opening for releasing the suture from an interior of the housing such that the suture can automatically transition from the flattened configuration into a curved configuration; a deployment element having a ribbon-shaped distal portion disposed in the housing, the ribbon-shaped distal portion of the deployment element having a surface with a set of formations configured to interface with the suture, the housing and the set of formations of the deployment element configured to collectively constrain the suture in the flattened configuration until the suture is released through the opening of the housing; and an actuator configured to move the deployment element relative to the housing to release the suture from the opening of the housing.

In some embodiments, a suture delivery system includes: a housing configured to contain a suture in a flattened configuration, the housing defining an opening for releasing the suture from an interior of the housing such that the suture can automatically transition from the flattened configuration into a curved configuration, the housing at least partially constraining the suture in the flattened configuration until the suture is released through the opening of the housing; a deployment element having a distal portion disposed in the housing, the distal portion of the deployment element having one or more formations configured to interface with the suture; a biasing mechanism disposed about a shaft, the biasing mechanism configured to transition between an undeployed configuration in which the biasing mechanism extends generally parallel to the housing and the distal portion of the deployment element and an expanded configuration in which a portion of the biasing mechanism bows outward in a direction away from the housing to form an asymmetrical shape that presses the housing against a suture site; and an actuator configured to move the deployment element relative to the housing when the biasing mechanism is in the deployed configuration to release the suture from the housing to deploy the suture in the suture site.

In some embodiments, a suture delivery method includes: manipulating a first control mechanism of a suture delivery system to expand a biasing mechanism of the suture delivery system, the biasing mechanism when expanded configured to press a housing of the suture delivery system against a portion of a graft disposed in a vessel, the housing configured to constrain a suture in a flattened configuration and including an opening through which the suture can be deployed from the housing such that the suture can transition to a natural curved configuration; manipulating a second control mechanism of the suture delivery system one or more times to cause a deployment element disposed within the housing to move proximally to partially deploy the suture from the housing such that a set of legs of the suture exit the opening of the housing and curve to penetrate through the portion of the graft and the vessel; and manipulating the second control mechanism one or more additional times to cause the deployment element to continue to move proximally to fully deploy the suture from the housing such that a tail of the suture that extends opposite to the legs exit the opening of the housing and curve to press against material disposed between the set of legs of the suture to hold the graft and the vessel relative to one another.

In some embodiments, a suture delivery method includes: manipulating a first control mechanism of a suture delivery system to expand a biasing mechanism of the suture delivery system, the biasing mechanism when expanded configured to press a housing of the suture delivery system against a portion of a graft disposed in a vessel, the housing configured to constrain a suture in a flattened configuration and including an opening through which the suture can be deployed from the housing such that the suture can transition to a natural curved configuration; with a mode selector of the suture delivery system in a first position such that a second control mechanism of the suture delivery system is engaged with a drive system of the suture delivery system, manipulating the second control mechanism one or more times to cause a deployment element disposed within the housing to move proximally to partially deploy the suture from the housing; in response to the mode selector being set to a second position, disengaging the second control mechanism from the drive system; and moving the deployment element distally to retract the suture back into the housing.

BRIEF DESCRIPTION OF DRAWINGS

FIG. 4 is a schematic diagram of a suture, according to am embodiment.

FIGS. 5A-5E depict different examples of sutures, according to various embodiments.

FIGS. 9A-9B are side and cross-sectional views, respectively, of a handle of a suture delivery system, according to an embodiment.

FIGS. 17A-17C are different views of an example suture that can be used with the suture advancement and retraction element depicted in FIGS. 15-16, according to an embodiment.

FIGS. 21A-21C depict a progression of releasing a suture from a suture delivery device where the suture is released from a distal end of the system, according to an embodiment.

FIGS. 22-24 depict example distal ends of a suture delivery system, according to an embodiment.

FIG. 25A depicts an example of connected sutures, according to an embodiment.

FIG. 25B is a detailed view of a suture with a connecting element for connecting to other sutures, according to an embodiment.

FIGS. 26A-26B depict different views of connected sutures, according to an embodiment.

DETAILED DESCRIPTION

Described herein are systems, devices, and methods for delivering sutures. In some embodiments, the systems, devices, and methods described herein may be used to bind together (e.g., to suture) a portion of an aorta and a graft, placing sutures during an endoscopic sleeve gastroplasty, during laparoscopic or robotic hernia repair, or during any other minimally invasive surgery procedures.

In some embodiments, the device described in this disclosure is an interventional medical device designed to deliver sutures to secure together a graft and a vessel wall. In some cases, a graft may be formed from a body tissue of a patient and in other cases, the graft may be engineered from other tissues (e.g., plastic, fabric, or other suitable soft and flexible tissue that may be penetrated by a suture). In an example embodiment an endovascular graft may be secured to the aorta for AAA repair. For instance, an example procedure for AAA repair generally involves delivering a graft to the inside of an aorta, and then securing the graft in place to form a stable channel for blood flow. After a graft is in place, the disclosed device can be used to deliver multiple sutures to the site of the graft to secure the graft to the neighboring vessel wall.

Figure 1:
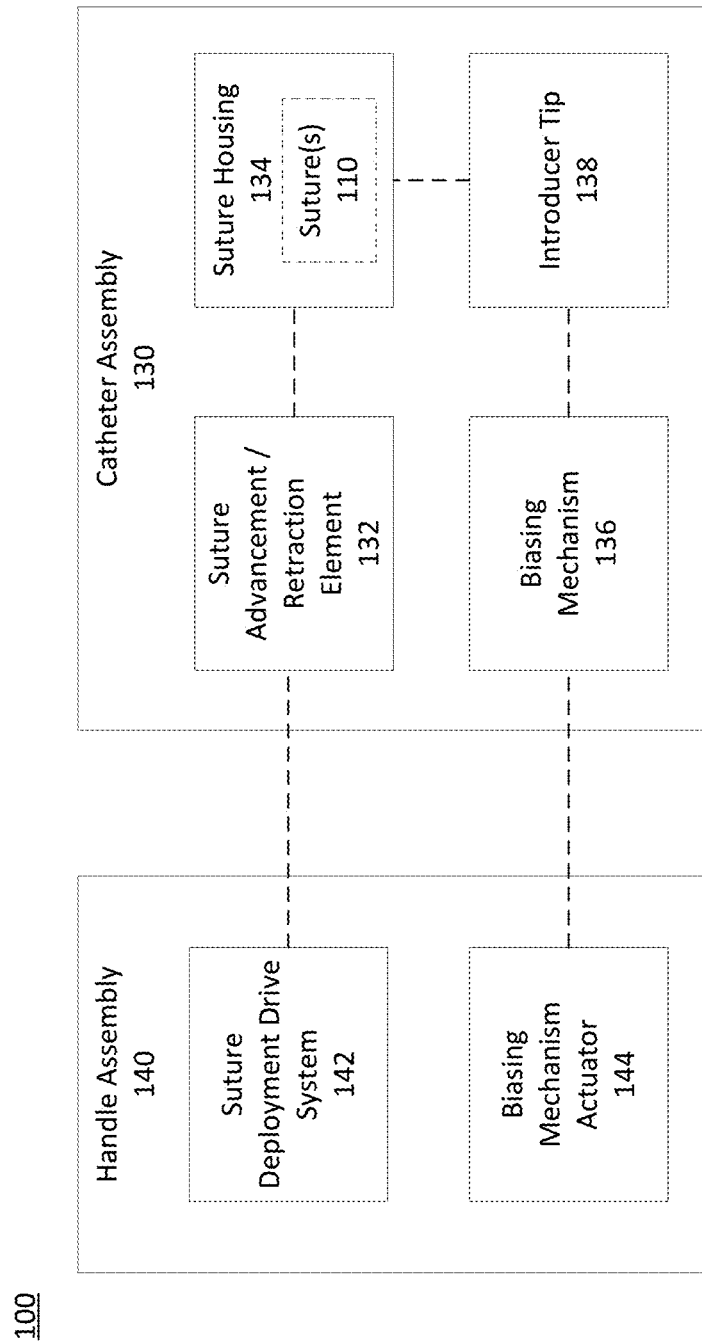
FIG. 1 is a schematic block diagram of a suture delivery system for endovascularly delivering sutures, according to an embodiment.

FIG. 1 is a schematic view of an example suture delivery system 100 for placing sutures 110 in a body of a patient, according to embodiments. Sutures 110 can be delivered into a portion of a patient's body via a catheter assembly 130. In some embodiments, a distal portion of the catheter assembly 130 may be guided to a region of a body that requires suturing (e.g., to the region in which a graft needs to be secured to a vessel wall such as the aorta of a patient. The distal portion of the catheter assembly 130 can be guided via a guidewire. For example, the catheter assembly 130 can define a guidewire lumen (not depicted) that can receive a guidewire and be guided along the guidewire to a suture site. Alternatively or additionally, the distal portion of the catheter assembly 130 can be guided via an access or introducer sheath to a suture site. For example, an access sheath may have been placed within the patient's vasculature, and the distal portion of the catheter assembly 130 can be advanced through the access sheath to the suture site. The distal portion of the catheter assembly 130 can be configured to release sutures at the suture site or region that requires suturing to bind or secure tissues and/or other material together (e.g., the aorta and the graft). As illustrated in FIG. 1, catheter assembly 130 can include a suture housing 134 configured to contain sutures 110. Suture housing 134 forms an enclosure that can constrain the sutures 110 inside (e.g., in a first state such as a flattened state, as further described below) and may include a suitable deployment window or opening for releasing sutures 110. The enclosure of suture housing 134 may have any suitable form for containing the sutures 110. In some embodiments, the suture housing 134 can have an elongate shape and can have a cross-sectional area that is or is substantially rectangular, square, trapezoidal, circular, etc.

Sutures 110 can be configured to clamp tissue and other materials together. For example, sutures 110 can include different portions that exert opposing forces that clamp together tissue and other materials or create a tightening effect on such tissue and other materials. In various embodiments, sutures 110 are configured to change shape (e.g., bend and/or fold) when being released from suture housing 134. In other words, sutures 110 can be configured to transition from a first configuration to a second configuration when the suture is released from the suture housing 134. The first configuration can be a constrained configuration, such as, for example, a flattened configuration. The second configuration can be a natural or deployed configuration, such as, for example, a curved configuration. In some cases, sutures 110 may be configured to automatically or spontaneously transition into the deployed configuration when sutures 110 are released from suture housing 134. For example, sutures 110 may be formed of shape-memory material or superelastic material and can be configured to revert back to a natural state (e.g., a curved state) while being released from the suture housing 134. Alternatively, in some cases, forces and/or torques may be exerted on sutures 110 to facilitate or cause the transition of the sutures 110 into their deployed configuration. Example shape-memory or superelastic materials may be metals, such as Nickel-Titanium alloy (nitinol), stainless steel, Elgiloy or cobalt alloy, plastic, or other materials known in the art that has the desired flexibility and strength to be flattened and can reform to the desired state and effectively clamp different materials or tissue together when released from suture housing 134. In example embodiments, nitinol50 ($Ni_{0.5}Ti_{0.5}$), nitinol60 ($Ni_{0.4}Ti_{0.6}$) or other compositions of nitinol described by $Ni_{1-x}Ti_x$ may be used. In some cases, sutures 110 may be made from plastic, metal, or a combination of plastic and/or metal materials. In some embodiments, sutures 110 may include coatings, such as radiopaque coatings, or markers, as further described below. Various embodiments of sutures 110 are further described below with reference to FIGS. 4-5E.

Catheter assembly 130 further includes a suture advancement/retraction element (SARE) or suture deployment element 132. As part of suture advancement, SARE 132 is configured to release sutures 110 from suture housing 134. In some embodiments, SARE 132 is configured to release each of sutures 110 by moving a suture toward a deployment window (e.g., an opening) in suture housing 134 and pushing the suture through the deployment window. As a part of suture retraction, SARE 132 is configured to retract a suture that is partially released back into the suture housing 134. In some embodiments, SARE 132 may retract the suture by moving the suture away from the deployment window of suture housing 134. In some embodiments, SARE 132 can be configured to move the sutures 134 by sliding (e.g., advancing and retracting) within the suture housing 134. For example, a distal portion of the SARE 132 can be disposed within the housing 134 and be configured to slide or move relative to the housing to move the sutures 110. Further details of advancing and retracting sutures 110 from suture housing 134 using SARE 132 are discussed below. Additionally, various embodiments of SARE 132 are also discussed below.

In some embodiments, SARE 132 can be implemented as an elongate structure with at least a region that has a flattened shape. For example, SARE 132 can have a ribbon-shaped structure or have a portion for receiving sutures 110 (e.g., a distal portion) that has a ribbon-shaped structure. In some embodiments SARE 132 can be implemented as a sled, e.g., an elongate strip having a rectangular cross-sectional area. The SARE 132 can include a plurality of formations that are configured to receive respective portions of the sutures 134. In some embodiments, the plurality of formations can have a repeating pattern such that subsets or formations are configured to receive an individual suture. In some embodiments, the plurality of formations can include ridges, notches, groove, channels, canals, or any other suitable structure for receiving and interfacing with a portion of a suture 110. In some embodiments, the sutures 110 can be disposed serially (e.g., in a row) along a length of a portion of the SARE 132, e.g., along a distal portion of the SARE 132 where the plurality of formations are disposed. The SARE 132 and the suture housing 134 collectively can be configured to constrain the sutures 110 in a first configuration (e.g., a flattened configuration). In some embodiments, the SARE 132 can be configured to interface with each suture 110 along its entire length, e.g., to minimize or reduce natural curving or warping of the suture 110 back to a natural curved state. As can be appreciated, sutures 110 that are memory set to a curved configuration but are constrained in a flattened state within the suture housing 134 can have a tendency to revert back to their curved configuration (e.g., via twisting or warping). As such, the SARE 132 can be designed with formations that are configured to receive and radially constrain portions of the sutures to reduce unintended movement of the sutures, thereby ensuring that they exit the suture housing 134 substantially normal to a deployment window of the housing 134. Further details of the radial constraining of sutures are provided with reference to FIGS. 13 and 16.

Catheter assembly 130 further includes an introducer tip 138 located at the distal end of catheter assembly 130. Introducer tip 138 may be an atraumatic structure (e.g., having a substantially conical, spherical, or other atraumatic shape) configured to facilitate introduction and navigation of catheter assembly 130 through patient vasculature to a region of the patient that requires suturing. In some embodiments, the introducer tip 138 can be coupled to a distal end of the suture housing 134, while a distal end of the SARE 132 can be free floating within the housing 134. As such, the SARE 132 can be configured to move or slide relative to the housing 134 when the introducer tip 138, the housing 134, and/or other components of the catheter assembly 130 are anchored or held in place within the patient, e.g., via a biasing mechanism 136 as further described below.

Catheter assembly 130 also includes a biasing mechanism 136. Biasing mechanism 136 is configured to change shape (e.g., expand). In other words, biasing mechanism 136 can be configured to transition from a first undeployed configuration in which the biasing mechanism 136 can extend generally or substantially parallel to a longitudinal axis of the catheter assembly 130 to a second deployed or expanded configuration in which the biasing mechanism 136 bows outward from the longitudinal axis. In some embodiments, the biasing mechanism 136 can be deployed to press a material, such as, for example, a graft, against a portion of tissue, such as, for example, a vessel wall (e.g., aortic wall). The biasing mechanism 136 can be configured to press a portion of the housing 134 containing the sutures 110 against the graft and tissue wall such that a window of the housing 134 through which the sutures 110 can be deployed is pressed against the graft. Such placement of the housing 134 and the window for deploying the sutures 110 can enable the suture delivery system 110 to deploy or deliver sutures through the window such that they directly contact and can penetrate through the graft and vessel wall. Further details of the sutures as they are deployed, and how the sutures can generate clamping or tightening effects on the tissue, are described with reference to later figures.

In an example embodiment, biasing mechanism 136 may be inserted into a vessel or a body cavity (e.g., in an aorta, a graft, or any other suitable vessel or body cavity) and may be expanded such that the biasing mechanism 136 directly contacts a portion of a material for suturing. The biasing mechanism in its expanded configuration can be configured to press against the walls of the vessel or body cavity to secure itself and other components coupled to it in place within the patient anatomy. Such securing or anchoring can ensure that a distal portion of the catheter assembly 130 and/or various components at the distal portion of the catheter assembly 130 do not move during a suturing procedure. For example, the biasing mechanism 136 can be coupled to the introducer tip 138, which can also be coupled to the suture housing 134. As such, expansion of the biasing mechanism 136 can maintain the introducer tip 136 and the suture housing 134 in place relative to a graft or vessel wall. The SAKE 134 can then move (e.g., slide) within the suture housing 134 to deploy sutures out of the suture housing 134. In some cases, the biasing mechanism 136 can be undeployed (e.g., reverted back to its unexpanded state) to allow the distal portion of the catheter assembly 130 to move relative to the patient anatomy. In some embodiments, the biasing mechanism 136 can be implemented as an expandable mesh or basket formed of a plurality of wires. In some embodiments, the plurality of wires can be formed of a metallic material such as stainless steel, while in other embodiments, the plurality of wires can be formed of a flexible polymer or plastic. In some embodiments, the biasing mechanism 136 can be implemented as a balloon. In some embodiments, the biasing mechanism 136 can be deployed by moving an inner or other shaft relative to the other. For example, a distal end of the biasing mechanism 136 can be coupled to an inner shaft, and a proximal end of the biasing mechanism 136 can be coupled to an outer shaft. Movement of the inner or outer shaft relative to the other can then deploy the biasing mechanism 136, i.e., transition the biasing mechanism from its unexpanded configuration to its expanded configuration. In some embodiments, markings can be provided at a proximal end of the suture deliver system 100 (e.g., in handle assembly 140) that provides guidance to a surgeon on the degree or extent of expansion of the biasing mechanism 136. In some embodiments, biasing mechanism 136 can be configured to expand to a structure having a maximum diameter of between about 5 mm to about 60 mm, including all values and subranges therebetween. Other details and embodiments of biasing mechanism 136 are further discussed below.

According to various embodiments, and consistent with the disclosed embodiment shown in FIG. 1, various operations of catheter assembly 130 are controlled by a medical professional (e.g., a surgeon) through a use of a handle assembly 140. For example, the surgeon may operate elements of handle assembly 140 to deploy and/or retract sutures 110 via SARE 132, to deploy, partially deploy, or contract biasing mechanism 136, or to move catheter assembly 130 to a new position within a body of a patient. In some cases, operations of catheter assembly 130 guided by a surgeon operating handle assembly 140 may be based on imaging obtained during a surgical procedure. In an example embodiment, the imaging may be used to determine whether the sutures 110 are being properly placed through graft and/or tissue within a patient or to observe any relevant events that may influence the surgical procedure (e.g., internal bleeding, incorrect folding of tissue, a rupture of a tissue, and the like). Any suitable imaging may be used during the surgical procedure. For example, ultrasound imaging, imaging using a computed tomography (CT) system, or imaging using internally placed cameras or optics can be used. While not depicted, in some embodiments, the system 110 can include imaging devices that are positioned to capture images or video of the deployment of the biasing mechanism and/or deployment of individual sutures.

Handle assembly 140 includes a suture deployment drive system (SDDS) 142. In some embodiments, SDDS 142 can include a suitable mechanism for moving SARE 132. In an example embodiment, the suitable mechanism can be a deployment lever (DL) operatively coupled with SARE 132.

A motion of the DL may control a motion of SARE 132, and, as a result, control the deployment and/or retraction of sutures 110 to or from tissues located within a patient. In some embodiments, SDDS 142 can include a button or other control mechanism that can be manipulated (e.g., depressed, slid, or otherwise moved) to move the SARE 132. In some embodiments, SDDS 142 can be coupled to an outer housing of the handle assembly 140, and the outer housing of the handle assembly 140 can be coupled to the SARE 132, e.g., via one or more connecting elements (e.g., shafts, fasteners, joints, etc.), Various embodiments of deployment drive system 142 are further described below.

Handle assembly 140 further includes a biasing mechanism actuator 144 configured to control expansion/contraction of biasing mechanism 136. In an example embodiment, biasing mechanism actuator 144 may include a slider or other suitable component (e.g., button, wheel, etc.) that can be moved (e.g., slid) to deploy the biasing mechanism 136. In some embodiments, the handle assembly 140 can include markings indicating a distance that the slider has been advanced, which can correspond or be associated with a degree or amount that the biasing mechanism 136 has been expanded. For example, the markings can indicate when the biasing mechanism 136 has been expanded to having a diameter of about 5 millimeters (mm), about 10 mm, about 15 mm, about 20 mm, about 25 mm, about 30 mm, about 35 mm, about 40 mm, about 45 mm, about 50 mm, about 55 mm, or about 60 mm, including all values and ranges therebetween. Various embodiments of biasing mechanism actuator 144 are described with reference to later figures below.

Figure 2:
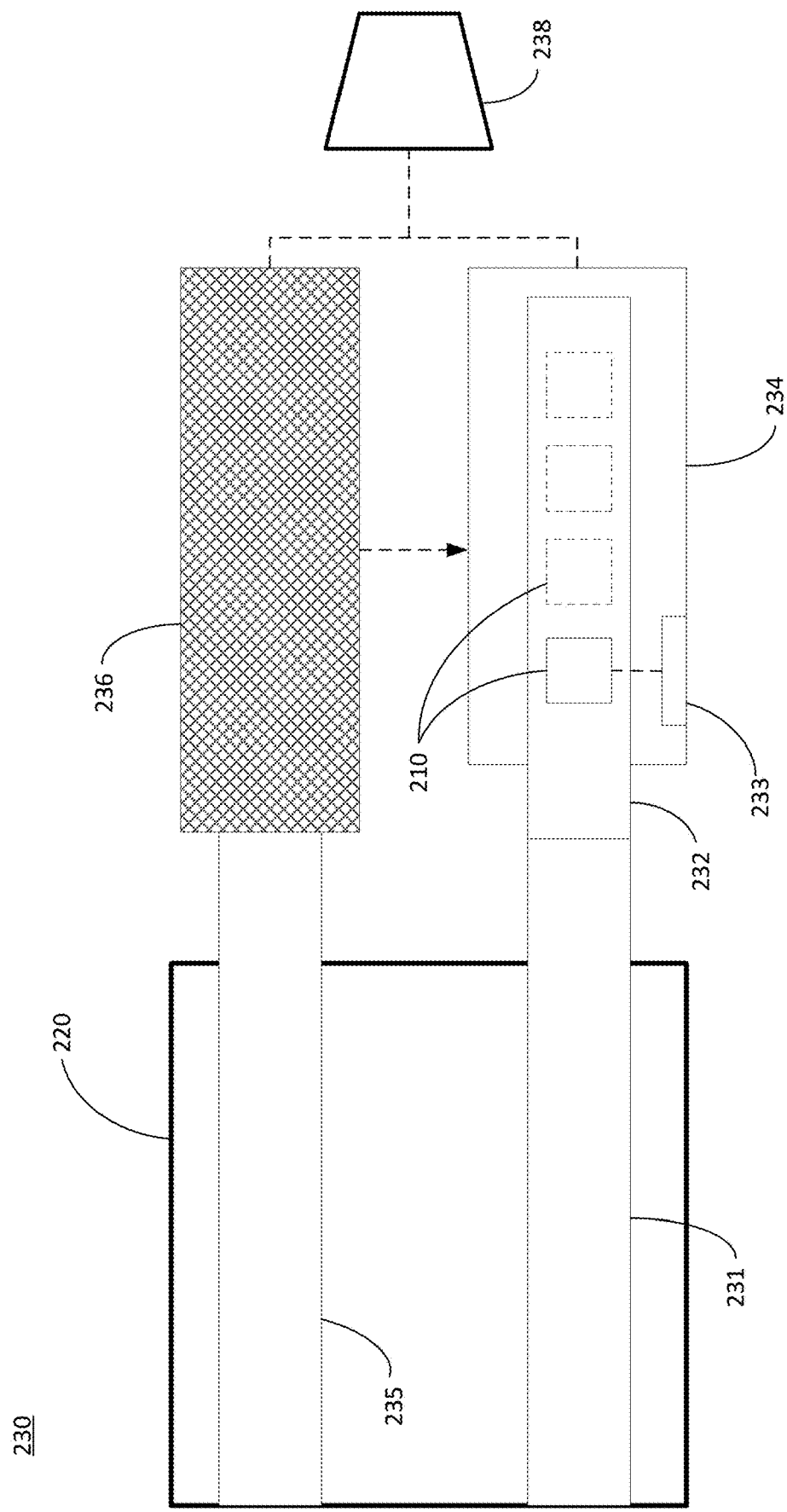
FIG. 2 is a schematic diagram of a catheter assembly of a suture delivery system, according to an embodiment.

FIG. 2 shows an example of catheter assembly 230 of a suture delivery system, according to embodiments. Catheter assembly 230 can include components that are structurally and/or functionally similar to other catheter assemblies described herein, including, for example, catheter assembly 130. For example, catheter assembly 230 includes an introducer tip 238, a biasing mechanism 236, a SARE 232, a suture housing 234, a set of sutures 210 placed on SARE 232, and a deployment window 233 located in suture housing 234. Further, catheter assembly 230 includes one or more shafts 231, 235 that can be used to couple the SARE 232, the biasing mechanism 236 and/or other components of the catheter assembly 230 to actuators and/or drive components disposed at a proximal end of the suture delivery device. The catheter assembly 230 can also include an outer sheath 220 or catheter 220 that defines a lumen for receiving the shafts 231, 235 and/or other components of the catheter assembly 230.

In some embodiments, biasing mechanism 236 can include a distal end coupled to introducer tip 238, and a proximal end coupled to shaft 235. In some embodiments, shaft 235 may be directly attached to biasing mechanism 236, while in other embodiments, shall 235 can be coupled via one or more other components to biasing mechanism 236. Similarly, in some embodiments, introducer tip 238 can be directly attached to biasing mechanism 236, while in other embodiments, introducer tip 238 can be coupled via one or more other components to biasing mechanism 236. For example, in a particular embodiment, introducer 238 can be coupled to a distal end of an additional shaft (e.g., a shaft that is disposed within a lumen of shaft 235 or an inner shaft), and the distal end of the biasing mechanism 236 can be coupled to this additional shaft. In some embodiments, when shaft 235 moves towards introducer tip 238, a distance between a distal end of shaft 235 and introducer tip 238 is reduced, thus reducing the distance between the distal and the proximal ends of biasing mechanism 236. Such movement can cause the biasing mechanism 236 to transition from an unexpanded configuration into an expanded configuration. In an example implementation, biasing mechanism 236 is an expandable mesh, e.g., a wire cage, basket, or other mesh-like structure formed of a plurality of wires that are woven or interleaved with one another. The wires can be formed of any suitable material, including, for example, nitinol, stainless steel, Elgiloy or cobalt alloy, plastic, or other materials known in the art that has the desired flexibility and strength. In some embodiments, the biasing mechanism 236 may be expanded by a different amount depending on the distance between the distal and the proximal ends of the biasing mechanism 236. Shaft 235 may be configured to move towards introducer tip 238 by at most a maximum distance, thus resulting in a maximum target expansion of biasing mechanism 236. In some embodiments, the biasing mechanism 236 in its maximum expanded state can have a diameter of about 20 mm, about 30 mm, about 40 mm, about 50 mm, about 60 mm, about 75 mm, or about 100 mm, including all values and ranges therebetween. In some cases, shaft 235 may be configured to move to a set of discrete positions (e.g., be configured to lock at a set of discrete positions), this resulting in a set of discrete expanded shapes or sizes for biasing mechanism 236. Alternatively, shaft 235 may be configured to move continuously from an initial position (e.g., corresponding to an unexpanded biasing mechanism 236) to the furthest position (i.e., move by the maximum target distance). In an example embodiment, the movement of shaft 235 is controlled by a surgeon via a slider, as further described with reference to later figures below.

In some cases, the biasing mechanism 236 may expand to a first configuration having a first shape and a first expanded volume and may expand in a second configuration having a second shape and a second expanded volume. In some embodiments, the first expanded volume may be larger than a second expanded volume. In some embodiments, the first shape may be different than the second shape. In an example embodiment, as further shown below, at least one of the first or the second shape may not be symmetric about a central axis of the biasing mechanism 236. In some embodiments, the biasing mechanism 236 may expand into an asymmetric structure or shape, e.g., in which a side of the biasing mechanism 236 that faces away from the housing 234 is configured to expand outwards (e.g., away from the housing 236) while a side of the biasing mechanism 236 that faces the housing 234 is configured to remain straight or unexpanded. In such embodiments, the side of the biasing mechanism 236 that faces the housing 234 may be generally flush and/or extend parallel to the housing 234 such that the biasing mechanism 236 when expanded can press the housing 234 against a portion of graft material and/or tissue without significantly deforming (e.g., curving or bending) the housing 234. Alternatively, in some embodiments, the biasing mechanism 236 can be configured to expand symmetrically about its central axis.

In some embodiments, shaft 235 may not be coupled to the biasing mechanism 236 but can be implemented as a sheath that covers the biasing mechanism 236. The sheath can then be retracted or advanced to allow the biasing mechanism 236 to expand out of the sheath or retract back into the sheath, respectively. In some embodiments, biasing mechanism 236 may be coupled to an elongate element (e.g., a shaft or rod) placed inside shaft 235, and shaft 235 can be configured to move relative to this elongate element. In such embodiments, biasing mechanism 236 may be an expandable mesh configured to self-expand (e.g., due to being formed from shape-memory or superelastic material) when shaft 235 is moved in a direction away from a distal end of catheter assembly 230 (i.e., in a direction away from introducer tip 238). In some cases, depending on a position of shaft 235 relative to biasing mechanism 236, biasing mechanism 236 may be fully expanded (e.g., when shaft 235 is fully retracted or moved maximally away from the distal end of catheter assembly 230), fully contracted (e.g., when shaft 235 is fully deployed or moved maximally towards the distal end of catheter assembly 230) or partially expanded when BAS 235 is partially retracted (or, in other words, partially deployed). In an example implementation of biasing mechanism 236 being an expandable mesh, the mesh may be formed from any suitable shape-memory material, such as nitinol, stainless steel, and the like.

It can be appreciated that biasing mechanism 236 formed as an expanded mesh is one possible illustrative way for implementing biasing mechanism 236, and various other implementations may be used. For example, biasing mechanism 236 may be an expandable balloon that may be inflated/deflated using any suitable fluid (e.g., gas or liquid, such as saline).

FIG. 2 further shows suture housing 234, which includes deployment window or opening 233. When biasing mechanism 236 is expanded, biasing mechanism 236 is configured to press a portion of the housing 234 against a portion of the graft and/or tissue. In particular, the biasing mechanism 236 when expanded can be configured to cause the deployment window 233 of the housing 234 to be pressed against the graft and/or tissue. The deployment window 233 can be through which one or more sutures 210 are deployed from within the housing 234. The sutures can be advanced one at a time out of the window 233 of the housing 234. Each time a suture is deployed, the biasing mechanism 236 can be undeployed or unexpanded, and the catheter assembly 230 moved such that the housing 234 is located at a different region of the graft and/or tissue. The biasing mechanism 236 can then be expanded or deployed again to press the housing 234 against the new region of graft and/or tissue. In some embodiments, the housing 234 can be configured to house or contain at least one suture, at least two sutures, at least three sutures, at least 4 sutures, at least 5 sutures, at least 6 sutures, at least 7 sutures, at least 8 sutures, at least 9 sutures, or at least 10 sutures, including all values and ranges therebetween. In an example embodiments, the housing 234 can be configured to house or contain between one and 4 sutures.

In the example embodiment shown in FIG. 2, SARE 232 can be disposed within housing 234. SARE 232 can have a proximal end that is attached to shaft 231. In use, movement of shaft 231 can cause a movement of SARE 232, such that SARE 232 can be controlled to deploy and/or retract a suture 210. In some embodiments, sutures 210 can be disposed in a distal portion of housing 234 that is distal to the window 233 such that each suture 210 can be pulled to deploy the suture through the deployment window 233. In such embodiments, the shaft 231 and SARE 232 can be moved proximally (i.e., away from introducer tip 238) to deploy a suture 210 and can be moved distally (i.e., toward introducer tip 238) to retract a suture 210 back into the housing 234. Alternatively, in other embodiments, SARE 232 may be moved towards introducer tip 238 to deploy a suture 210 and/or moved away from introducer tip 238 to retract a suture 210.

Consistent with the disclosed embodiment shown in FIG. 2, SARE 232 can move within suture housing 234. Sutures 210 can be held in a flattened configuration, as described with reference to FIG. 1, and can be received in formations disposed on a surface of SARE 232, as further described below. SARE 232 and the housing 234 collectively can constrain the sutures 210 in their flattened configuration. Sutures 210, when stored in suture housing 234, can experience elastic stress. When SARE 232 moves such that a suture (or at least a part of the suture) aligns with deployment window 233 and is deployed through the deployment window 233, the suture may curve (e.g., bend) automatically as it exits the deployment window. Example embodiments illustrating a process of a suture release are further described with reference to FIGS. 20A-20F below.

Catheter assembly 230 further includes an outer sheath 220 configured to enclose or receive at least some parts of elements 231-236, e.g., to provide a smooth profile for insertion and/or navigation of the catheter assembly 230. In some embodiments, outer sheath 220 can be configured to move relative to a distal portion of the catheter assembly 230, e.g., to cover one or more components at the distal end of the catheter assembly 230 (e.g., suture housing, biasing mechanism, SARE, etc.). As such, outer sheath 220 can be a retractable sheath that can cover the SARE, biasing mechanism, and other distal components during initial delivery of the catheter assembly 230 into the body and can be retracted prior to actuation of the biasing mechanism and SARE. In some embodiments, shafts 231, 235 can be disposed concentrically within the sheath 220. For example, shaft 235 can be disposed within a lumen of shaft 231, or vice versa.

In use, sutures 210 may be configured to be deployed after biasing mechanism 236 is expanded. The biasing mechanism 236, when expanded, can anchor or hold the housing 234 and other components of the catheter assembly 230 in place within a graft and/or vessel. The anchoring provided by the biasing mechanism 236 can ensure that the sutures 210 are deployed at a precise location that does not change as the SARE 232 and/or other components of the suture delivery system are actuated. In some embodiments, sutures 210 may be prevented from being deployed until biasing mechanism 236 has been properly expanded. For example, a locking mechanism can be used to prevent deployment of sutures 210 until the biasing mechanism 236 has been deployed. Such locking mechanism can be implemented via a mode selector, as further described with reference to FIG. 3. In some embodiments, the locking mechanism can be an inter-lock that can be configured to release the suture deployment control mechanism in response to the biasing mechanism 236 being deployed, e.g., in response to the shaft 235 advancing at least a minimum or pre-set distance to at least partially deploy the biasing mechanism.

Figure 3:
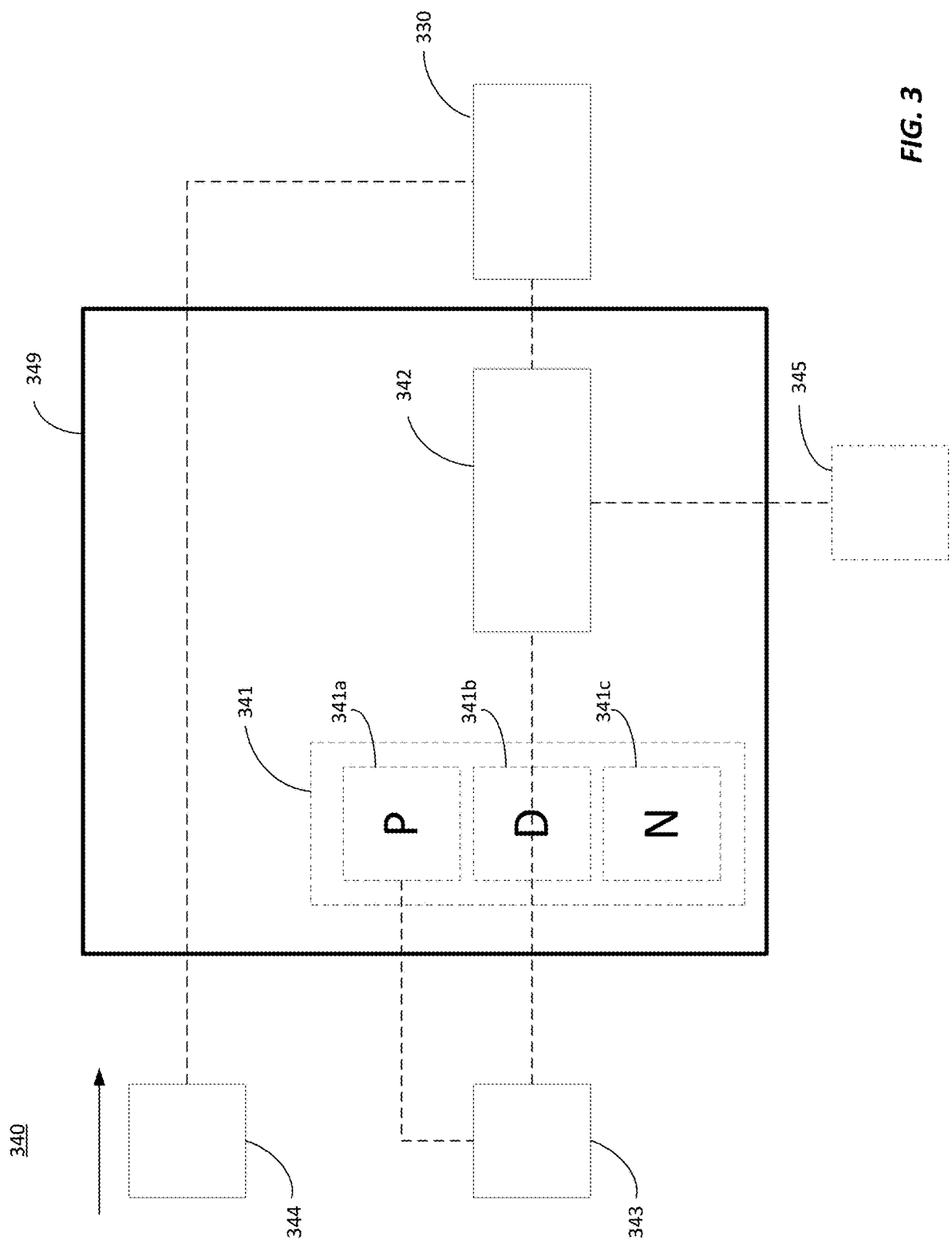
FIG. 3 is a schematic diagram of a handle assembly of a suture delivery system, according to an embodiment.

FIG. 3 shows an example of a handle assembly 340 of a suture delivery system, according to embodiments. Handle assembly 340 can include components that are structurally and/or functionally similar to other handle assemblies described herein, including for example, handle assembly 140. Handle assembly 340 can be coupled to a catheter assembly 330, which can be any of the catheter assemblies described herein, such as, for example, catheter assembly 130 and/or 230. Handle assembly 340 can include a handle housing 349. Handle housing 349 can house or support a suture deployment drive system 342, a suture deployment control mechanism 343, and optionally a mode selection system or mode selector 341 having configurations 341A-341C and/or a suture number selection mechanism (SNSM) 345. The handle assembly 340 can also include a biasing mechanism actuator 344.

Suture deployment control mechanism 343 and suture deployment drive system 342 allow a medical professional (e.g., a surgeon) to control deployment of a suture, e.g., through graft and/or tissue of a patient. In an example embodiment, the surgeon controls the deployment of the suture via suture deployment control mechanism 343. Suture deployment control mechanism 343 can be any suitable trigger or activation device, such as, for example, a lever, a button, a wheel, a slider, etc. When suture deployment control mechanism 343 is coupled to suture deployment drive system 342 and manipulated or actuated (e.g., depressed or pumped), suture deployment drive system 342 can cause a SAKE or suture deployment element of a catheter assembly (e.g., SARE 232, which can be implemented as a sled or ribbon-shaped structure) to move to advance a suture out of a suture housing of the catheter assembly (e.g., suture housing 234). As described above, the suture deployment element can be partially disposed within the suture housing, and can interface with one or more sutures. In some embodiments, manipulation of the suture deployment control mechanism 343 can cause a first portion of the handle assembly 340 to move relative to a second portion of the handle assembly 340. The first portion of the handle assembly 340 can be coupled to the suture deployment element of the catheter assembly, while the second portion of the handle assembly 340 can be coupled to the suture housing of the catheter assembly. As such, movement of the first portion of the handle assembly 340 relative to the second portion of the handle assembly 340 causes the suture deployment element of the catheter assembly to move relative to the suture housing. In some embodiments, manipulation of the suture deployment control mechanism 343 can cause the suture deployment element to move proximally (i.e., in a direction toward the handle assembly 340) relative to the suture housing, and sutures positioned distal of a suture deployment window of the suture housing can be pulled proximally toward the suture deployment window for deployment.

In some embodiments, each individual suture can be released from the suture housing in stages. For example, with each manipulation or actuation of the suture deployment control mechanism 343 (e.g., each pump or depression of a lever, button, or other control mechanism), a suture may advance out of a suture deployment window of the suture housing by a partial amount, e.g., be partially released from deployment window 233. After a series of actuations, a suture can be fully deployed. Prior to being fully deployed, the surgeon may reverse the deployment of the suture (e.g., retract the suture). Further details of deployment drive system 342 and operations of suture deployment control mechanism 343 are discussed below.

In some embodiments, a mode selection system or mode selector 341 determines coupling of deployment drive system 342 with suture deployment control mechanism 343. Mode selection system 341 allows a user to switch between engaging suture deployment control mechanism 343 with deployment drive system 342 and disengaging suture deployment control mechanism 343 from the deployment drive system 342. In some embodiments, the suture deployment control mechanism 343 can include a drive element (e.g., a drive clasp) that can be engaged and/or disengaged from a ratchet or ratcheting tube of the deployment drive system 342 via mode selection system 341. The mode selector allows a user to switch between: a first mode illustratively identified as a "P" mode (corresponding to a first configuration 341A), which locks suture deployment control mechanism 343 in a closed configuration or position and prevents its actuation (e.g., pressing or pushing); a second mode illustratively identified as a "D" mode (corresponding to a second configuration 341B), which engages suture deployment control mechanism 343 with the deployment drive system 342 for delivering the sutures; and a third mode illustratively identified as a "N" mode (corresponding to a third configuration 341C), which disengages suture deployment control mechanism 343 from the deployment drive system 342. In the "N" mode, the suture deployment control mechanism 343 being disengaged from the drive system 342 can enable a user to retract a suture back into a suture housing, e.g., by moving a first portion of the handle assembly 340 that is coupled to a suture deployment element relative to a second portion of the handle assembly 340 that is coupled to a suture housing. In use, the mode selector 341 can be set to the "P" mode when the user desires to prevent accidental deployment of sutures, e.g., during insertion, navigation, and/or repositioning of the catheter assembly. The mode selector 341 can be set to the "D" mode when the user desires to deploy one or more sutures. And the mode selector 341 can be set to the "N" mode when the user desires to retract one or more sutures. Further embodiments of mode selection system 341 are discussed below.

Optionally, in some embodiments, the suture housing of a suture delivery device may house a few sutures (e.g., two, three, four, five, and the like). In some embodiments, the handle assembly 340 can include a SNSM 345 that is configured to index from one suture to the next during deployment of multiple sutures. For example, the handle assembly 340 can include a stepped track, whereby each step of the track corresponds to a distance traversed by the suture deployment element to fully deploy a single suture. A protrusion or tooth can be disposed within the track, and advance within the track until it contacts the end of each step of the track. This protrusion can be coupled (via one or more intervening components) to the suture deployment element. As such, once the distance for deploying one suture is traversed by the suture deployment element, the track can lock further movement of the suture deployment element to prevent accidental deployment of a second suture at the same location as a first suture. In such embodiments, a SNSM 345 can be a control mechanism that allows a user to advance the protrusion onto the next step of the track, thereby allowing a second suture to be deployed. In some embodiments, the SNSM 345 can be a wheel or knob that can be rotated to advance the protrusion into the next step of the track. The SNSM 345 can include markings that act as a counter, thereby allowing a surgeon to select the number of the suture that the surgeon is deploying. The SNSM 345 can be configured to ensure that sutures are selectively deployed one at a time. In other words, SNSM 345 can prevent two sutures from being deployed at the same location. In an example embodiment, when SNSM 345 is implemented as a wheel, a rotation of a wheel by a prescribed amount may allow selection of a suture for deployment.

Biasing mechanism actuator 344 may be any suitable slider, lever, button, and the like configured to deploy (e.g., expand) or contract biasing mechanism 236. In an example embodiment, biasing mechanism actuator 344 may be a laterally sliding element configured to move between a first position corresponding to a contracted biasing mechanism 236 and a second position corresponding to a fully expanded biasing mechanism 236. In various embodiments, positions of the laterally sliding element between the first and the second position may correspond to a partially expanded biasing mechanism 236. In some embodiments, markings or other indicia present on the handle assembly 340 can indicate to a user the degree of expansion of the biasing mechanism. For example, a first marking can indicate that the biasing mechanism is expanded to a diameter of about 5 mm if the sliding element is aligned with the first marking, and a second marking can indicate that the biasing mechanism is expanded to a diameter of about 10 mm if the sliding element is aligned with the second marking. In some embodiments, markings indicating that the biasing mechanism has been expanded to certain diameter can include, for example, one or more of 5 mm, 10 mm, 15 mm, 20 mm, 25 mm, 30 mm, 35 mm, 40 mm, 45 mm, 50 mm, 55 mm, 60 mm, etc., or any other increments and/or values therebetween.

FIG. 4 shows a schematic illustration of an embodiment of a suture 410. Suture 410 can be structurally and/or functionally similar to other sutures described herein, including, for example, sutures 110, 210, etc.

Suture 410 may have a first prong or leg 411A and a second prong or leg 411B connected via a bridging element 416 that together form a U-shaped structure. In an embodiment, the legs 411A and 411B can have proximal ends joined to each other and elongate bodies that extend parallel to one another. Both legs 411A and 411B may have sharp respective ends or sharpened tips 412A and 412B, configured to penetrate through graft and/or tissue. Optionally, suture 410 may include a tail 414, which can optionally include an opening 415. Tail 414 may be an elongated region. In some embodiments, tail 414 can have a length that is less than the length of the legs 411A and 411B, e.g., tail 414 can have a length of about half of the length of legs 411A and 411B. Alternatively, tail 414 can have a length that is longer than the legs 411A and 411B. Opening 415 may be of any suitable shape (e.g., substantially rectangular, oval, circular, and the like). In an example embodiment, opening 415 may be configured to allow several sutures to be connected via a connecting element (e.g., an elongated element such as a segment of a wire, a thread, and the like) that may pass through opening 415. In some embodiments, tail 414 may optionally include a structure 413 and the tail end, which may be of any suitable shape (e.g., a circular shape, for example). In an example embodiment, tail 414 may smoothly transition into structure 413 (e.g., the transition may not have sharp edges), as the absence of the sharp edges may prevent tissue damage and/or tissue rupture. Similarly, tail 414 may smoothly transition into bridging element 416 connected to the legs 411A and 411B.

In various embodiments, suture 410 is configured to curl (e.g., bend or curve) into a deployed state or configuration when released from suture housing 234. For example, suture 410 can be formed of shape-memory or superelastic material and can have a natural state that forms a curved or annular shape. In some embodiments, suture 410 can be formed from laser cutting a metallic tube. As such, in its natural state, suture 410 can form a loop or annular shape that corresponds to a cross-section of the metallic tube. In some embodiments, suture 410 can be constrained in a straightened or flattened configuration within a suture housing of a suture delivery device (e.g., suture housing 134). In the flattened configuration, the tail 414 of the suture can extend in a direction opposite to the direction of the elongate bodies of the two legs 411A and 411B. When the suture 410 is released form the suture housing, the suture 410 can revert back to its curved or natural configuration in which the tail 414 and the two legs 411 and 411B are curved and can exert forces in opposite directions such that the tail 414 and the two legs 411 and 411B are configured to collectively hold a graft and/or vessel wall together. In particular, the tail 414 and the two legs 411A and 411B can create a clamping force or a tightening effect that can maintain a section of a graft and the vessel wall relative to one another. For example, the two legs 411A can curve to form an annular shape or loop, and the tail 414 once curved can be configured to reduce an effective diameter of the loops thereby creating a tightening effect. This tightening effect or clamping can further secure the hold that the suture 410 has on the graft and/or tissue held between the legs 411A and 411B and the tail 414.

In some embodiments, the tail 414 can have an opening 415, which can lead to a tail 414 with a wider width. In some embodiments, the wider width of the tail can increase a clamping force exerted by the tail. In some embodiments, the opening 415 can be configured to receive connection elements that can be used to couple multiple sutures 414 together. Further details of connected sutures are described with reference to FIGS. 25A-26B.

In some embodiments, when suture 410 does not include tail 414 (e.g., only includes legs 411A and 411B that are joined together), the suture 410 may transition into a curved configuration having shape S1, as shown in FIG. 5A. Alternatively, in some embodiments, a suture 410 that does not include tail 414 (e.g., only includes legs 411A and 411B that are joined together) may transition into a curved configuration having a flatter shape S2, as shown in FIG. 5B. In some embodiments, a flatter shape S2 may be beneficial as it can bind tissues e.g., a graft tissue and an aorta tissue) closer to each other than shape S1.

In some embodiments, a suture 410 containing legs 411A and 411B and a tail 414 may transition into a curved configuration having a shape S3, as shown in FIG. 5C. Tail 414 may be used to press on tissue and/or material disposed between the legs 411A and 411B to further bind or clamp together the graft and/or tissue. Tail 414 can be configured to bend as shown in FIG. 5C such that tail 414 has an increased bend radius past the U-shaped structure of the tails 411A and 411B, invading inside the diameter of suture 410 and improving the damping of suture 410. In some embodiments, a suture 410 including legs 411A and 411B and a tail 414 can transition into a curved configuration having shape S4, as shown in FIG. 5D. The shape S4 can be flatter and can lead to greater clamping forces. In an example embodiment, tail 414 forming shape S4 can be wider than tail 414 forming shape S3, which can also increase clamping forces generated by the tail 414.

In some embodiments, a suture 410 may include regions that contain radiopaque markers or a radiopaque coating. For example, tail 414, bridging element 416, or legs 411A and/or 411B may include radiopaque markers (e.g., a ring, collar, band, or plate) or be coated with a radiopaque material. For example, a portion of tail 414 may include a radiopaque marker or be coated with a radiopaque material. In an example embodiment, the radiopaque material may be platinum, gold, and the like.

In various embodiments, sutures 410 can be created by laser cutting from a metal tube such as nitinol or stainless steel. In some embodiments, after laser cutting the sutures 410, the sutures 410 can be electropolished or polished via other methods to create rounded edges, e.g., to avoid unintentional cutting of tissue. Although other materials might be used, nitinol or stainless steel are exemplary examples of materials with spring-like resilience and strength, such that they can formed in the curved shape, flattened for delivery, and revert to their curved shape when fully deployed. Sutures 410 when transitioned back into their curved shape can create sufficient clamping or tightening forces that ensure that material held between the legs 411A, 411B and the tail 414 of the suture 414 are maintained together, retaining such material together against physiologic forces, for example, such as blood flow in an aorta.

FIG. 5E shows that another shape S5 for a suture 410 in a curved configuration, in which tail 414 is configured to fit between prongs 411A and 411B. The suture 410 in FIG. 5E may be manufactured by laser cutting suture 410 from a metal tube, as described above. As depicted, the suture 410 in its curved configuration can have a diameter that generally corresponds to a diameter of a cross-section of the metal tube from which the suture is cut.

Figure 6A:
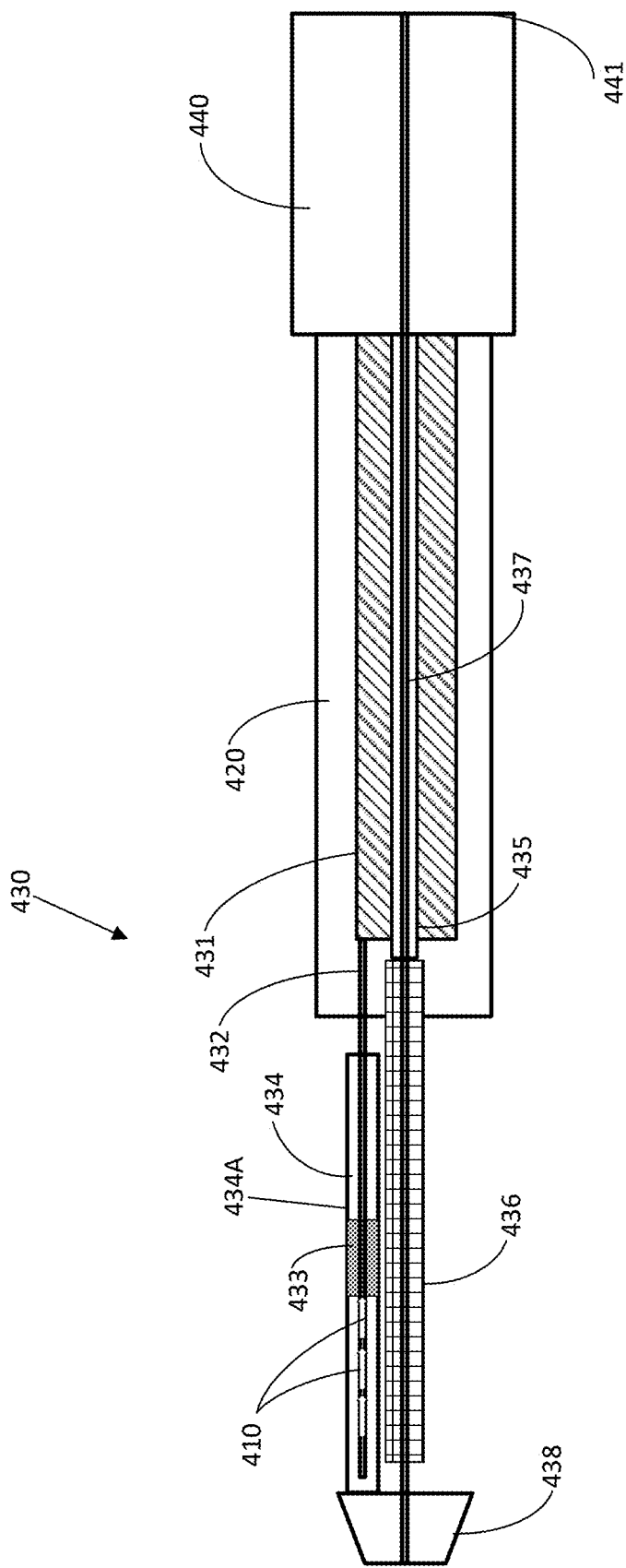
FIGS. 6A-6B schematically depict a catheter assembly of a suture delivery system in different configurations, according to an embodiment.
Figure 6B:
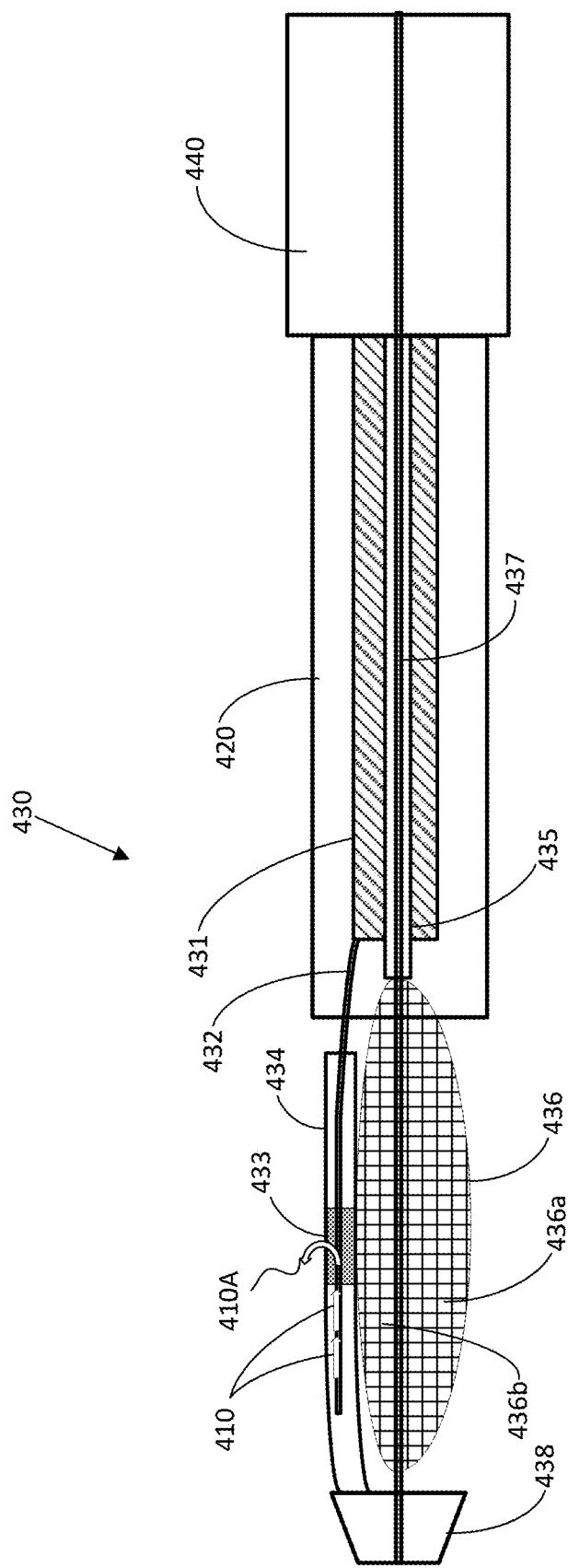

FIGS. 6A-6B schematically depict a suture delivery device including a catheter assembly 430 and a handle assembly 440. FIG. 6A depicts the suture delivery device in a first configuration where a biasing mechanism 436 of the suture delivery device is in an unexpanded or undeployed configuration, while FIG. 6B depicts the suture delivery device in a second configuration where the biasing mechanism 436 is in an expanded or deployed configuration. The suture delivery device depicted in FIGS. 6A and 6B, as well as the catheter assembly 430 and the handle assembly 440, can be structurally and/or functionally similar to other suture delivery devices, catheter assemblies, and/or handle assemblies described herein. For example, catheter assembly 430 includes an introducer tip 438, a biasing mechanism 436, a suture advancement/retraction element (SARE) 432, a suture housing 434, a set of sutures 410, and a deployment window 433. Further, catheter assembly 430 includes shafts 431, 435, 437 and an outer sheath 420.

The shafts 431, 435, 437 can be concentrically positioned within the sheath 420. For example, shaft 431 can be positioned around shaft 435, which in turn can be positioned around shaft 437. As such, the shafts 431, 435, 437 and the sheath 420 can have a common longitudinal axis. Each of the shafts 431, 435, 437 can be coupled to different components of the catheter assembly 430 such that movement of the shafts 431, 435, 437 relative to one another can move and/or manipulate such components. The shaft 437 can extend through an entire length of the suture delivery device, e.g., from the introducer tip 438 to a proximal side 441 of handle assembly 440. In some embodiments, the shaft 437 can be viewed as a central shaft which is aligned with a longitudinal axis of the catheter assembly 430. The shaft 437 can define a lumen, e.g., for receiving a guidewire. As such, the suture delivery device can be configured to be advanced or guided along a guidewire that has been positioned within the patient vasculature. In some embodiments, the shaft 437 can be coupled to a distal end of the biasing mechanism 436, and the shaft 435 can be coupled to a proximal end of the biasing mechanism 436. Accordingly, the biasing mechanism can be expanded by moving shaft 435 relative to shaft 437. In some embodiments, the shaft 431 can be coupled to a proximal end of the SARE 432. The SARE 432 can have a distal portion that is disposed within the suture housing 434 and can translate or slide within the suture housing 434. As described above with reference to FIGS. 1-4 and therefore not restated in detail herein, the SARE 432 can include formations that are configured to receive sutures 410, and collectively with the suture housing 434, the SARE 432 can constrain the sutures 410 in a flattened configuration within the suture housing 434.

In various embodiments, a distal portion of the catheter assembly 430, e.g., a portion including introducer tip 438, suture housing 434, and biasing mechanism 436, is configured to be fixed in place by using biasing mechanism 436 expanded within a cavity or body lumen. As described above, biasing mechanism 436 can be expanded in response to a motion of shaft 435 relative to shaft 437. In an example embodiment, biasing mechanism 346 is an expandable and contractable mesh, cage, or basket. The mesh, cage, or basket may be made from wires formed of any suitable material (e.g., nitinol, stainless steel, plastic, and the like).

Biasing mechanism 436 may be expanded when shaft 435 is moved towards introducer tip 438. In some embodiments, biasing mechanism 436 can be configured to expand asymmetrically, as schematically depicted in FIG. 6B. For example, biasing mechanism 436 can be configured to expand on a side 436a facing away from the suture housing 434 a greater amount than on a side 436b facing toward the suture housing 434. The biasing mechanism 436 can be disposed symmetrically about the shaft 437 (or substantially symmetrically about the shaft 437) in an unexpanded state, and can be disposed asymmetrically about the shaft 437 in the expanded state.

After expansion, biasing mechanism 436 can be configured to anchor in place introducer tip 438 and suture housing 434 (see FIG. 6B). For example, the biasing mechanism 436 can be configured to contact and press against the wall of a vessel to anchor itself and other components attached to it in place. In particular, side 436a of the biasing mechanism 436 can be configured to directly contact and press against the wall of a vessel and/or graft material, and side 436b of the biasing mechanism 436 can be configured to press the suture housing 434 against the wall of the vessel and/or graft material. As such, collectively, the sides of the catheter assembly 430 are pressed against the walls of the vessel and/or graft material to anchor the distal portion of the catheter assembly 430 in place.

In various embodiments, other elements of catheter assembly 430 are configured to move relative to introducer tip 438 and suture housing 434. For example, shaft 431 can be configured to move in a direction away from introducer tip 438 and pull along an attached SARE 432 containing sutures 410 placed over a top surface of SARE 432. SARE 432 can be disposed within the suture housing 434 without being fixed to any portion of the housing 434. As such, SARE 432 is configured to move within housing 434 to move sutures 410. In some embodiments, sutures 410 can be constrained between formations on a top surface of SARE 432 and an internal surface 434A of housing 434 that faces the formations. Such constraining of sutures 410 results in sutures 410 being held in a flattened state. As described above, the SARE 432 can be configured to interface with each suture 410 along its entire length and therefore prevent the suture 410 from twisting or bending in undesirable ways within suture housing 434. When the SARE 432 moves proximally, i.e., toward the handle assembly 440, the SARE 432 can move sutures 410 toward the deployment window 433. As sutures 410 pass next to deployment window 433, sutures 410 are configured to curve while being released from inside of suture housing 434 through deployment window 433. FIG. 6B schematically depicts a suture 410A being released through deployment window 433.

In various embodiments, an outer sheath 420 is used to shield at least some of the elements of catheter assembly 430, e.g., during insertion and/or advancement of the catheter assembly 430. In some embodiments, outer sheath 420 can be configured to cover suture housing 434 and biasing mechanism 436 during insertion of catheter assembly 430 into a body of a patient (e.g., into an aorta of a patient) and be retracted to uncover suture housing 434 and biasing mechanism 436 (e.g., outer sheath 420 may move away from introducer tip 438 to uncover suture housing 434 and biasing mechanism 436. In various embodiments, motions of various components of suture delivery device may be controlled by a surgeon by operating various control mechanisms of handle assembly 440, as further described below.

Figure 7A:
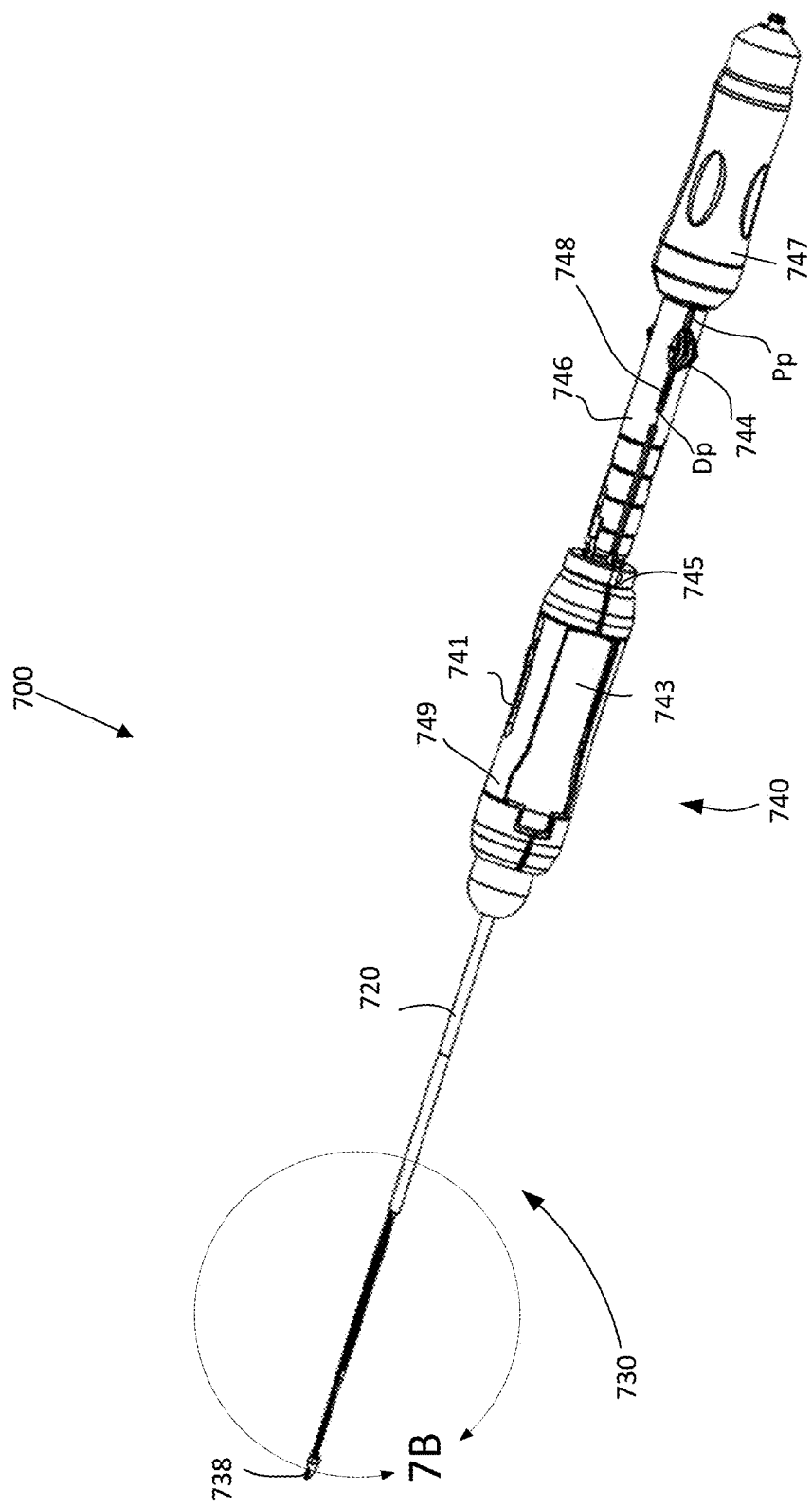
FIG. 7A is a side view of an example suture delivery system for endovascularly delivering sutures, according to an embodiment.

FIG. 7A shows a perspective view of an example suture delivery device 700, according to embodiments. Suture delivery device 700 can include components that are structurally and/or functionally similar to other suture delivery devices described herein, including, for example, suture delivery device 100. Device 700 includes a catheter assembly 730 and a handle assembly 740. Various details of a distal portion of catheter assembly 730 are further shown in FIG. 7B. Handle assembly 740 includes a suture deployment control mechanism 743, a mode selection system 741, a handle housing 749, an SNSM 745, a ratcheting tube 746, a biasing mechanism actuator 744, and a support handle 747.

As described above, suture deployment control mechanism 743 may interact with a drive system to facilitate deployment of sutures by catheter assembly 730. The drive system can include the ratcheting tube 746, which is coupled to the introducer tip 738 (e.g., via a central shaft). The suture deployment control mechanism 743 can be implemented as a lever that can be pumped or pressed to move the ratcheting tube 746 relative to the outer housing 749. Movement of the ratcheting tube 746 relative to the outer housing 749 can cause movement of a suture deployment element or SARE, as further described below. Mode selection system 741 controls the coupling of suture deployment control mechanism 743 and ratcheting tube 746. The ratcheting tube 746 extends within the housing 749. When mode selection system 741 is set to a first mode such as a drive or "D" mode, the suture deployment control mechanism 743 can be configured to engage with the ratcheting tube 746 such that each pump of the suture deployment control mechanism 743 causes the ratcheting tube 746 to move relative to the suture deployment control mechanism 743 and the housing 749. Alternatively, mode selection system 741 can be set to other modes, further described below, where the suture deployment control mechanism 743 is locked or not engaged with the ratcheting tube 746.

SNSM 745 is configured to configured to control selection of a suture for deployment. As described above and shown in greater detail in later figures, SNSM 745 is configured to advance a protrusion through one or more steps of a stepped channel that controls deployment of multiple sutures. Handle assembly 740 also includes a biasing mechanism actuator 744 configured to deploy (e.g., expand) a biasing mechanism of catheter assembly 730. In an example embodiment, biasing mechanism actuator 744 includes a slider that is configured to slide along a slit or channel 748 located in ratcheting tube 746. The biasing mechanism actuator 744 can be coupled to a proximal end of the biasing mechanism, e.g., via a shaft. As such, advancement of the biasing mechanism actuator 744 can be configured to move the proximal end of the biasing mechanism toward its distal end to expand it. In an example embodiment, at a distal position (Dp) within slit 748, biasing mechanism actuator 744 may be configured to fully expand a biasing mechanism of catheter assembly 730, and at a proximal position (Pp) within slit 748, biasing mechanism actuator 744 may be configured to fully contract or undeploy the biasing mechanism of catheter assembly 730. In positions between Dp and Pp, biasing mechanism actuator 744 may be configured to partially expand the biasing mechanism of catheter assembly 730.

Figure 7B:
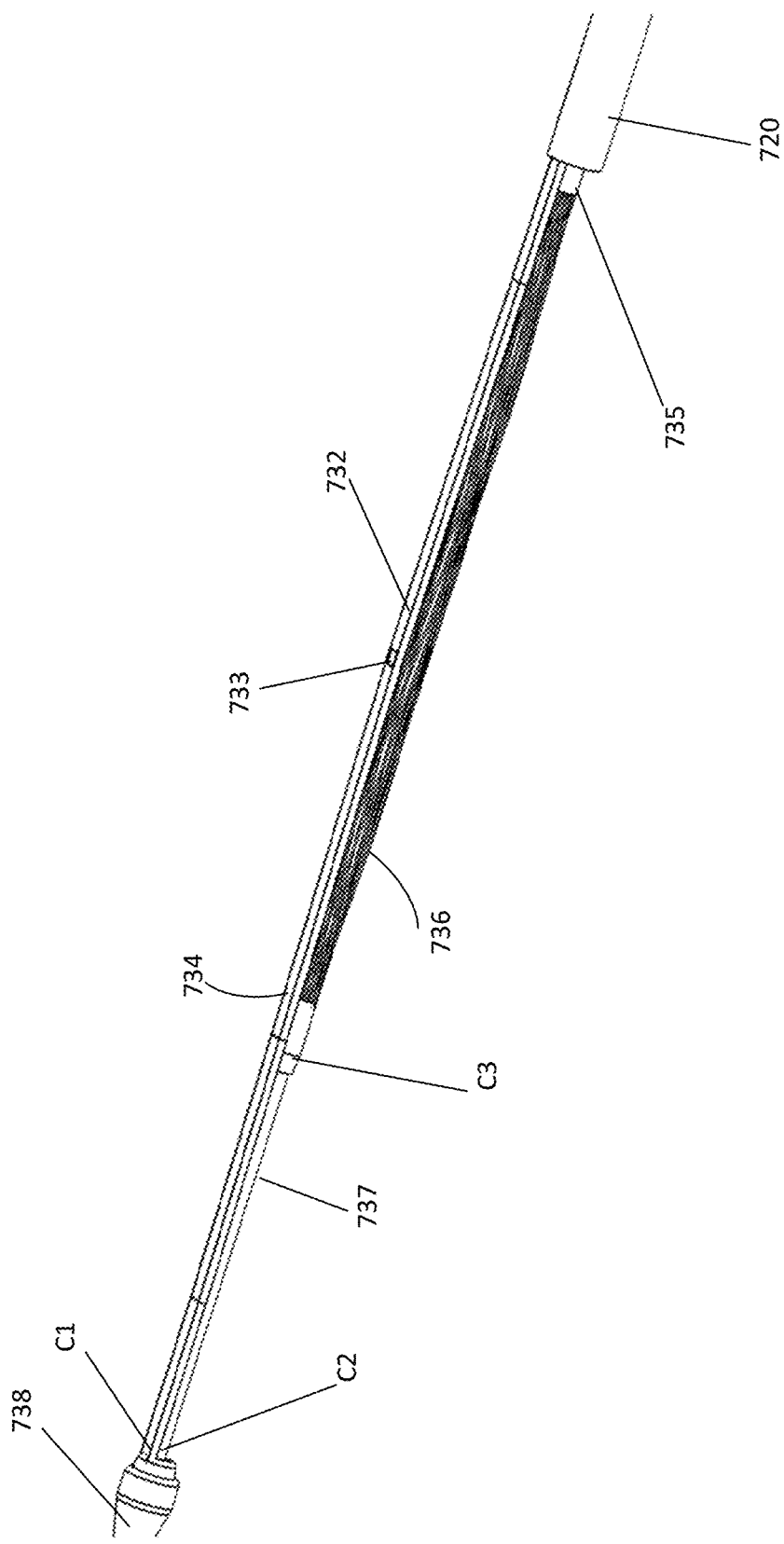
FIG. 7B is a detailed view of a distal portion of an example suture delivery system, according to an embodiment.

FIG. 7B shows further details of a distal portion of catheter assembly 730. As shown, the distal portion of the catheter assembly 730 can include an introducer tip 738, a suture housing 734, portions of shafts 735, 737, and a biasing mechanism 736. The introducer tip 738 can be connected to a suture housing 734 at a connection C1 and connected to a central shaft 737 at a connection C2. Suture housing 734 can be configured to contain a SARE. Central shaft 737 is connected to a distal end of biasing mechanism 736 at a connection C3. Further, biasing mechanism 736 is connected to shaft 735 at its proximal end. Shaft 735 may include a hollow lumen within which shaft 737 is disposed. In use, shaft 735 can slide relative to central shaft 737 to deploy the biasing mechanism 736.

FIG. 7B further shows suture housing 734 with deployment window 733, through which sutures disposed within the suture housing 734 can be released. In various embodiments, suture housing 734 is configured to be flexible such that suture housing 734 can bend or bow outward (e.g., away from a longitudinal axis of the catheter assembly 730) when the biasing mechanism 736 is deployed. FIG. 7B further shows an outer sheath 720, which can surround the shafts 735, 737. In some embodiments, portions of the biasing mechanism 736, the suture housing 734, and/or other components at the distal portion of the catheter assembly 730 can be retracted within the sheath 720, e.g., during insertion or navigation of the catheter assembly 730.

Figure 8A:
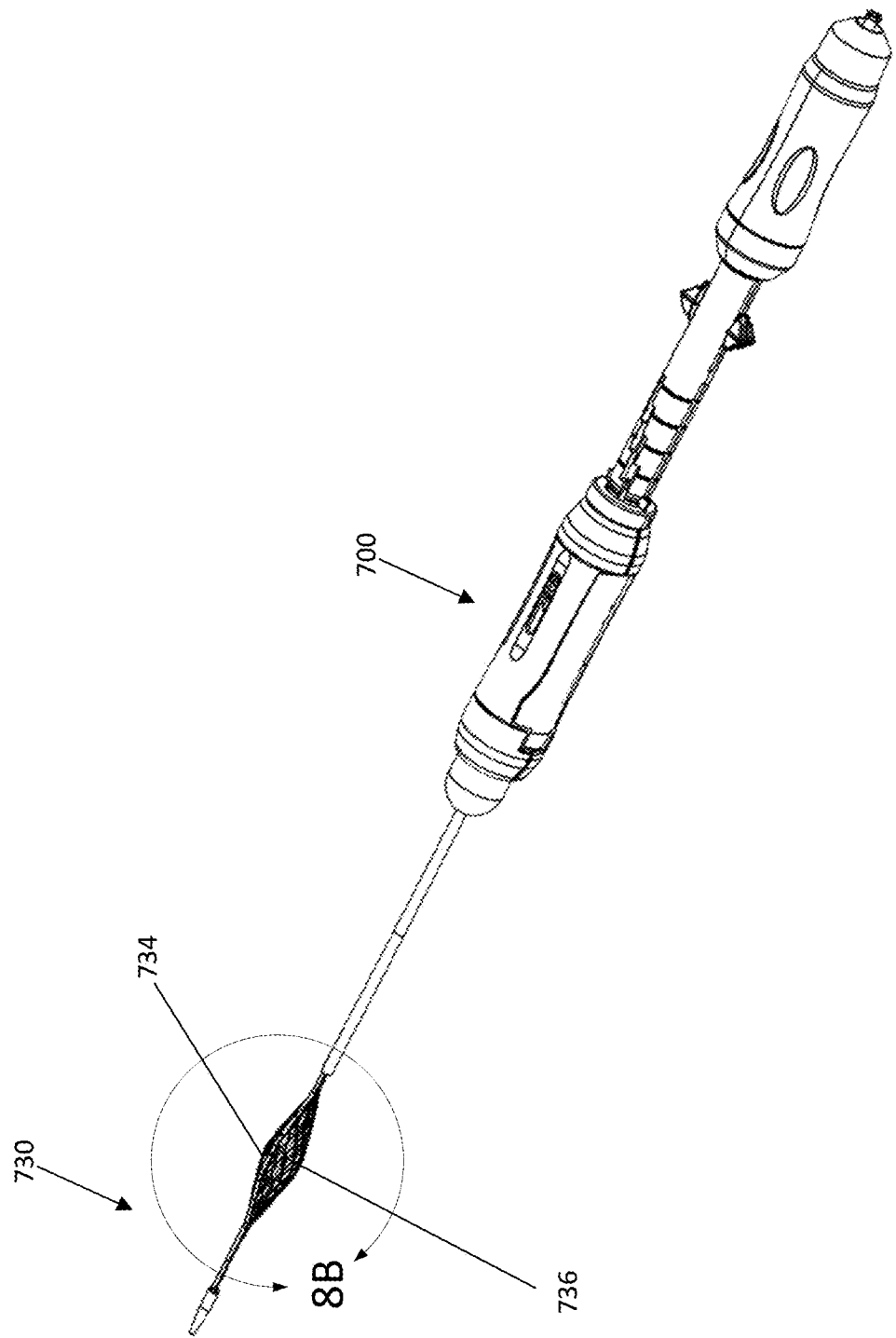
FIG. 8A is a side view of an example suture delivery system having an expanded biasing mechanism, according to an embodiment.

FIG. 8A shows a perspective view of suture delivery device 700 with biasing mechanism 736 expanded. Further details of a distal portion of catheter assembly 730 are shown in FIG. 8B.

Figure 8B:
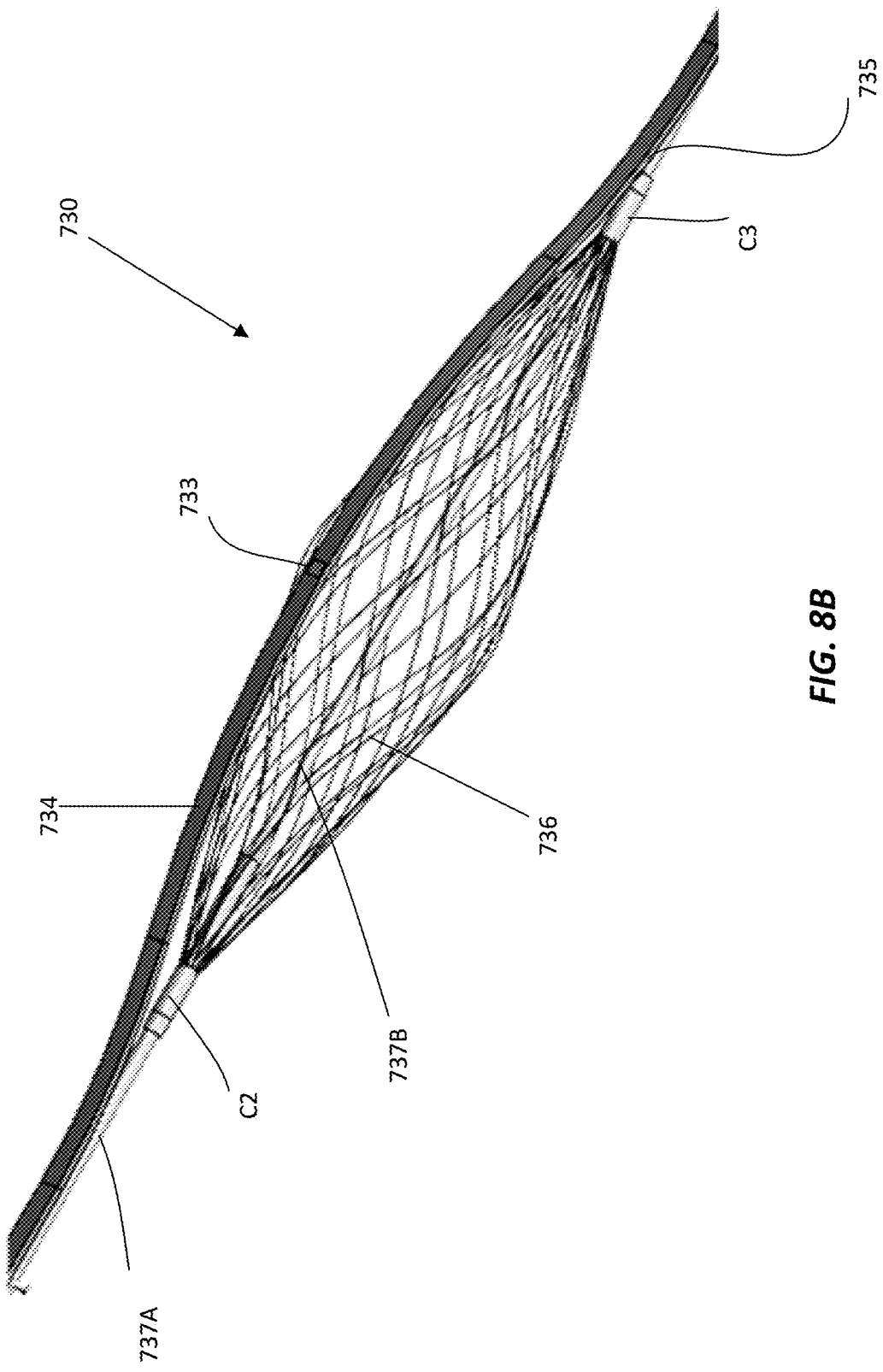
FIG. 8B is a detailed view of a distal portion of an example suture delivery system having an expanded biasing mechanism, according to an embodiment.

As shown in FIG. 8B, a first section 737A of central shaft 737 is connected at connection C2 with biasing mechanism 736 (e.g., a distal end of biasing mechanism 736), and a second section 737B of central shaft 737 passes through biasing mechanism 736 and through a lumen of shaft 735. In an example embodiment, shaft 735 is connected to biasing mechanism 736 at a connection C3 (e.g., a proximal end of biasing mechanism 736). As shown in FIG. 8B, suture housing 734 is adjacent to biasing mechanism 736. When biasing mechanism 736 is expanded, suture housing 734 can be configured to bias or bow slightly outward, e.g., such that suture housing 734 can be pressed against a surface of a portion of graft and/or tissue. In some embodiments, the deployment window 733 can be disposed at a point along suture housing 734 that is furthest from a longitudinal axis of the catheter assembly 730 (e.g., a longitudinal axis defined by shaft 737. Such positioning of the deployment window 733 can ensure that the deployment window 733 makes contact with and presses against the portion of the graft and/or tissue, which allows a suture deployed through the deployment window 733 to penetrate through the graft and/or tissue. In an example embodiment, suture housing 734 is connected to first section 737A of shaft 737, e.g., at its distal end.

FIGS. 9A-9B illustrate further details of handle assembly 740. FIG. 9A shows a side view of a portion of handle assembly 740, including mode selection system 741, handle housing 749, suture deployment control mechanism 743, and SNSM 745. Additionally, handle assembly 740 includes ratcheting tube 746 containing a set of connected channels 751 that form a stepped channel. The ratcheting tube 746 can form a part of a suture deployment drive system 742. The suture deployment drive system 742 can also include a drive clasp 763 attached to suture deployment control mechanism 743 (e.g., lever). As suture deployment control mechanism 743 is being pressed, drive clasp 763 is configured to push against rachets or teeth 761 formed on a portion of ratcheting tube 746 disposed inside handle housing 749. While not depicted in FIGS. 9A and 9B, the ratcheting tube 746 at its proximal end is attached to the central shaft 737 of the catheter assembly 730. When the distal portion of the catheter assembly 730 is disposed at a suture site and the biasing mechanism 736 is deployed, pressing of the suture deployment control mechanism 743 causes the handle housing 749 to move proximally relative to the ratcheting tube 746, e.g., the drive clasp 763 together with handle housing 749 and suture deployment control mechanism 743 move in a direction away from introducer tip 738 and towards the proximal end of device 700. The handle housing 749 can be coupled at its proximal end to shaft 731, which in turn is coupled to a SARE that is disposed within the suture housing 734. As such, movement of the handle housing 749 relative to the ratcheting tube 746 causes the SARE to move proximally within the suture housing 734, which can move a suture toward the suture deployment window 733. In an example embodiment, each pressing of suture deployment control mechanism 743 results in a small discrete motion of drive clasp 763, handle housing 749, and suture deployment control mechanism 743 towards the proximal end of device 700. The distance traveled by drive clasp 763 due to a single pressing of suture deployment control mechanism 743 may be the same as the distance between the neighboring teeth of ratcheting tube 746. In an example embodiment, to deploy a suture via deployment window 733, suture deployment control mechanism 743 is depressed multiple times, each time advancing the suture out of the deployment window 733 a predetermined distance. After each pressing of suture deployment control mechanism 743, a spring (not shown in FIGS. 9A and 9B) may be configured to return suture deployment control mechanism 743 into an open configuration. In the open configuration, suture deployment control mechanism 743 can be positioned such that a free end of suture deployment control mechanism 743 is spaced from handle housing 749, and suture deployment control mechanism 743 can be pressed toward handle housing 749 to further move handle housing 749, suture deployment control mechanism 743, etc. proximally relative to the ratcheting tube 746. In an example embodiment, during the first pressing of suture deployment control mechanism 743, ends of legs or prongs (e.g., legs or prongs 411A and 411B of suture 410) may advance out of deployment window 733. During the second pressing of suture deployment control mechanism 743, at least a portion of the elongate bodies of the legs may advance out of the deployment window 733. During the third pressing of suture deployment control mechanism 743, the legs of suture may be entirely out of the deployment window 733, and during a fourth pressing of suture deployment control mechanism 743, a tail of a suture (e.g., tail 414) may be released from deployment window 733. It should be appreciated that having four pressing actions for releasing an entire suture is an illustrative example, and other numbers of pressing actions may be used for releasing the entire suture. In various embodiments, a partially released suture may be retracted (if the suture is not fully released) as further described below.

FIG. 9B shows that suture deployment control mechanism 743 and handle housing 749 are connected (e.g., attached) to a T-shaped element 762. In an example embodiment, T-shaped element 762 is connected to the shaft 731 of catheter assembly 730, as shown in FIG. 9B. A motion of T-shaped element 762 initiated by the motion of drive clasp 763 results in the motion of shaft 731, and as a result, the motion of a SARE attached to suture deployment element 731. The motion of SAKE. (e.g., towards a proximal end of device 700) results in sutures being deployed from deployment window 733 as the sutures move past deployment window 733.

Figure 10:
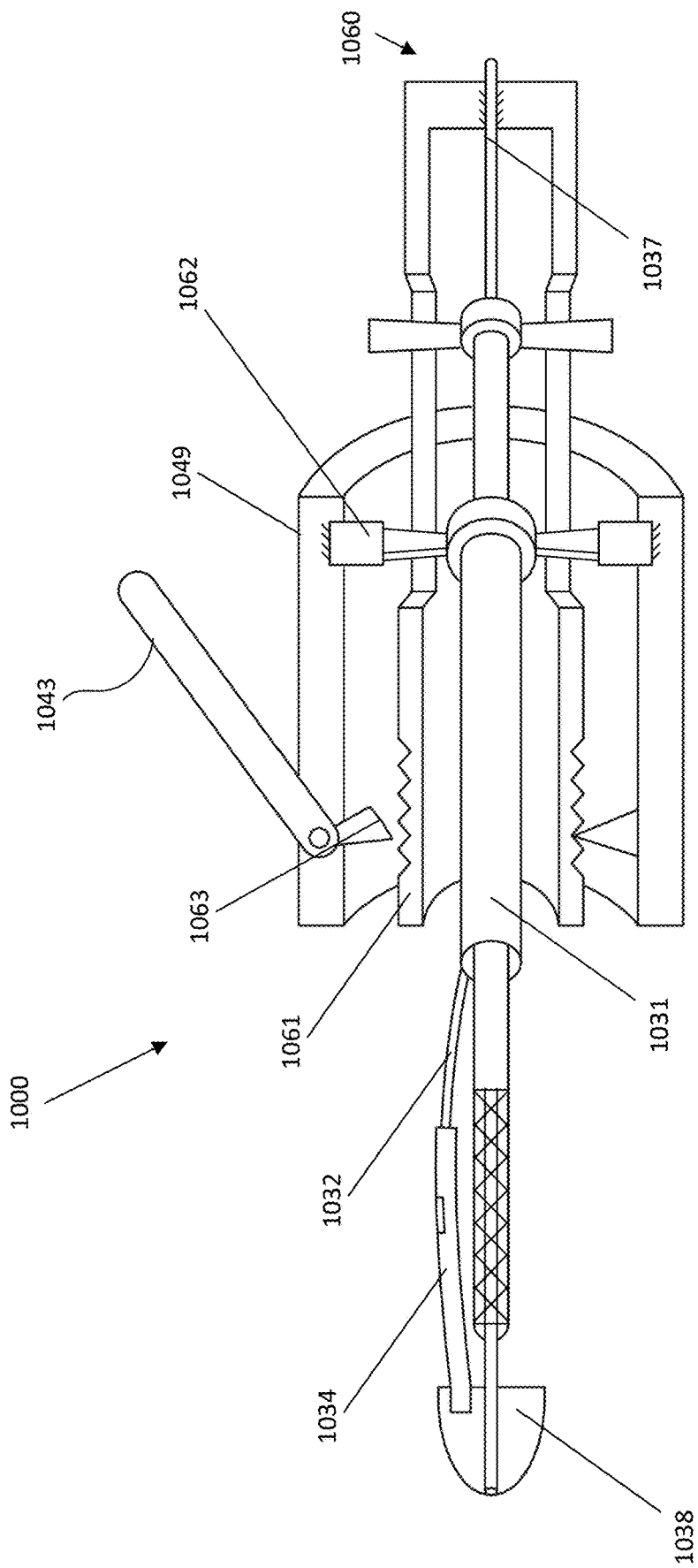
FIG. 10 a schematic diagram of a suture delivery system showing connections between proximal handle components and distal catheter components, according to an embodiment.

FIG. 10 illustratively depicts a suture delivery device 1000, providing a detailed view of connections for driving movement of different components of the suture delivery device 1000. Suture delivery device 1000 can include components that are structurally and/or functionally similar to components of other suture delivery devices described herein, including, for example, suture delivery devices 100 and/or 700. In an example embodiment, a suture deployment control mechanism 1043 with drive element 1063 (e.g., a drive clasp) is configured to push a ratcheting tube 1061 to move handle housing 1049, a T-shaped element 1062, a shaft 1031, and a suture advancement/retraction element 1032 proximally relative to the ratcheting tube 1061 (e.g., toward a proximal end 1060 of device 1000). The ratcheting tube 1061 in turn is coupled to a shaft 1037 that is coupled to an introducer tip 1038 of the catheter assembly. The introducer tip 1038 can be coupled to a suture housing 1034. As such, proximal movement of the handle housing 1049, the T shaped element 1062, and the shaft 1031 relative to the ratcheting tube 1061 can cause the suture advancement/ retraction element 1032 to move proximally relative to the suture housing 1034, thereby advancing sutures proximally toward a deployment window of the suture housing 1034.

Figure 11A:
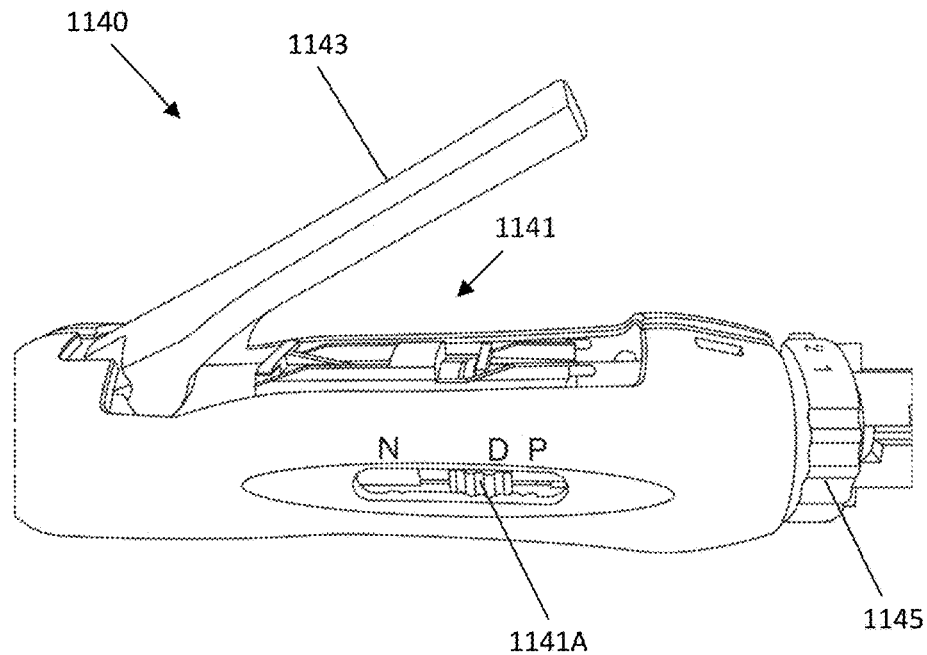
FIG. 11A is a perspective view of a handle of a suture delivery system, according to an embodiment.
Figure 11B:
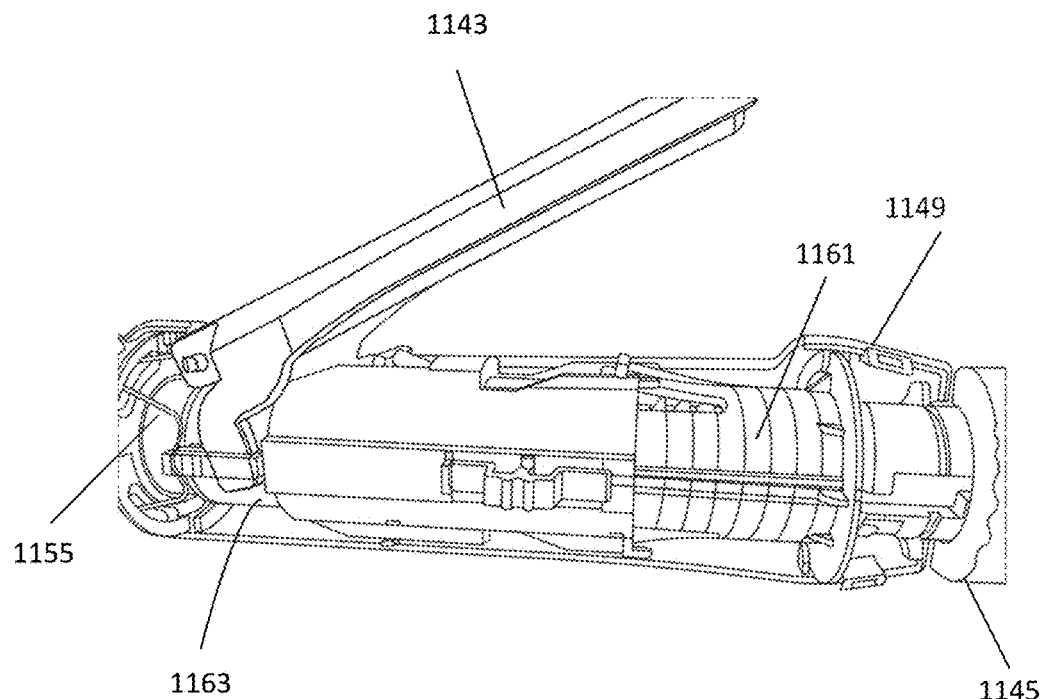
FIG. 11B is a view of the handle of the suture delivery system of FIG. 11A with certain housing portions not shown to show an interior of the handle.

FIGS. f and 11B provide detailed views of an example handle assembly 1140 for suture delivery device 1100, according to embodiments. Suture delivery device 1100 and its components can be functionally and/or structurally similar to other like components described herein. For example, FIGS. 11A and 11B show suture deployment control mechanism 1143, a mode selection system 1141 having a slider or knob 1141A that is configured to move (e.g., slide) between "N," "D," and "P" positions as previously described, suture number selection mechanism 1145, and a handle housing 1149. While mode selection system 1141 may be implemented in a variety of ways, the mode selection system 1141 is configured to lock the suture deployment control mechanism 1143 and/or disengage or engage the suture deployment control mechanism 1143 from components that drive the movement of a suture advancement/retraction element. Mode selection system 1141 can be functionally and/or structurally similar to mode selection system 341 described with reference to FIG. 3. For example, when slider 1141A is positioned at position "P," a "park" mode is selected. In this position, suture deployment control mechanism 1143 is locked, e.g., in a closed position, thus resulting in a suture advancement/retraction element associated with a catheter assembly for device 1100 being fixed in place.

When mode selection system 1141 is shifted in "D" mode, suture deployment control mechanism 1143 can spring to an open position, as shown in FIGS. 11A and 11B. Thus, in "D" ("drive") mode, suture deployment control mechanism 1143 can be pressed on to deploy sutures, as described above. When slider 1141A of mode selection system 1141 is placed in a "N" ("neutral") mode, teeth of ratcheting tube 1161 may be disengaged from a drive element 1163, thus allowing suture deployment control mechanism 1143 and housing 1049 to move freely forward (e.g., towards the distal end of device 1100). In some cases, when slider 1141A is in "N" position, suture deployment control mechanism 1143 may be prohibited from moving toward the proximal end of device 1100, e.g., via stepped channel of ratcheting tube 1061 (see FIG. 11E) and may only be allowed to move forward.

Figure 11C:
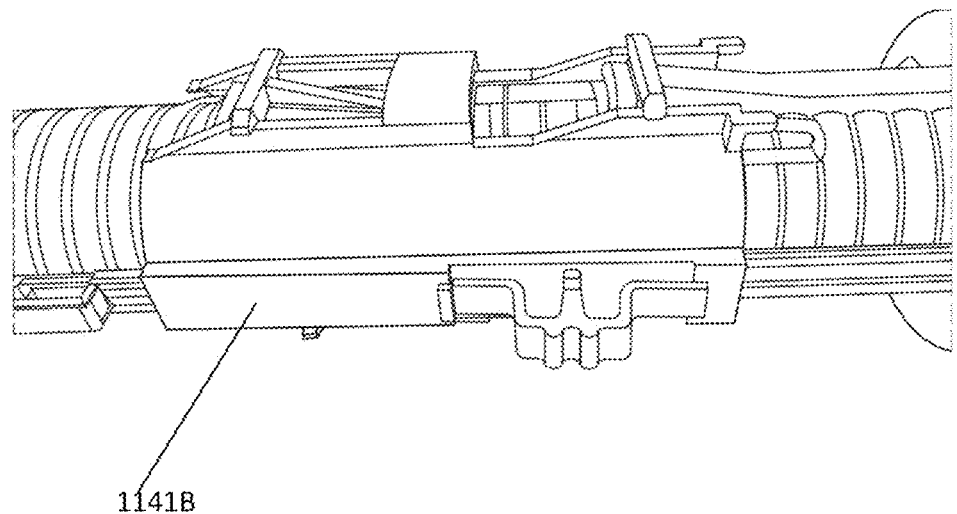
FIGS. 11C-11F are detailed views of different elements of the handle of the suture delivery system of FIG. 11A.
Figure 11D:
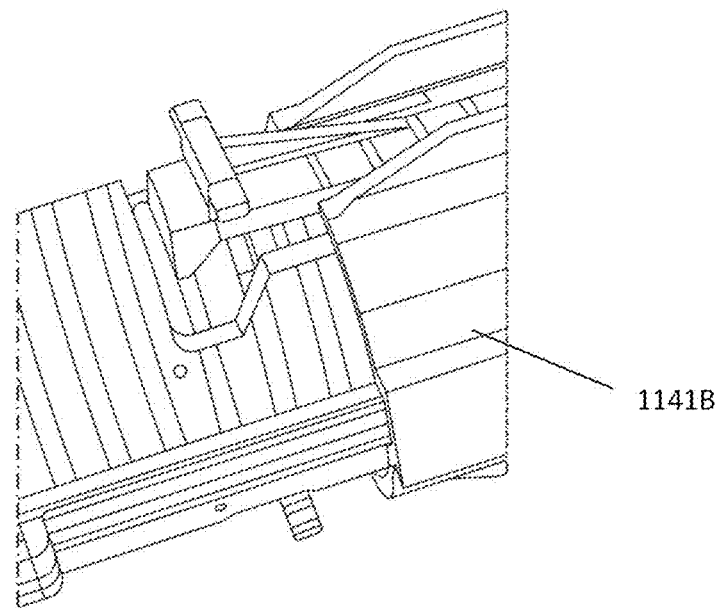

FIGS. 11C and 11D show an element 1141B of mode selection system 1141 that is configured to control coupling of drive element 1163 with ratcheting tube 1161. In some embodiments, the drive element 1163 can include teeth capable of preventing ratcheting tube 1161 from sliding relative to drive element 1163. In some embodiments, when mode selection system 1141 is shifted in "D" mode, the drive element 1163 is engaged with the ratcheting tube 1161 and can slide one tooth at a time down along the ratcheting tube 1161. When mode selection system 1141 is shifted in "N" mode, the drive element 1163 can be disengaged from the ratcheting tube 1161, allowing the handle housing 1149 to move relative to the ratcheting tube 1161. In some embodiments, separate teeth on the drive element 1163 can allow for proximal or distal movement of the handle housing 1149 relative to the ratcheting tube 1161.

Figure 11E:
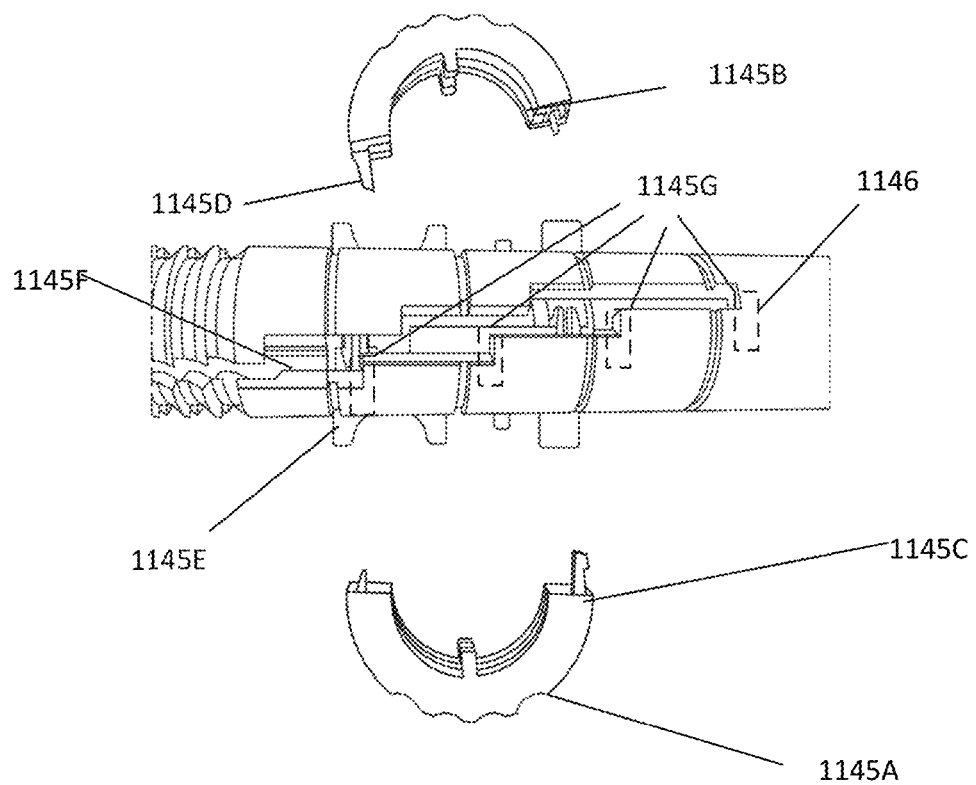
Figure 11F:
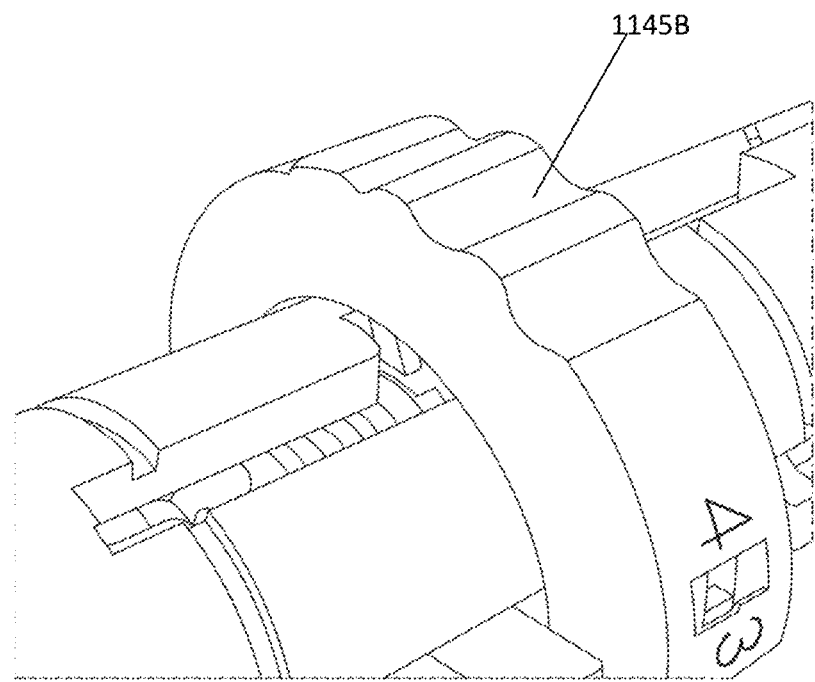

FIGS. 11E and 11F illustrate further details of suture number selection mechanism 1145. In an example embodiment, suture number selection mechanism 1145 is configured to allow a certain amount of motion for suture deployment control mechanism 1143, drive element 1163, and attached to them a suture deployment element (e.g., SDE 731), after which the motion of suture deployment control mechanism 1143 is seized. Such functionality of suture number selection mechanism 1145 prevents a surgeon from deploying multiple sutures in the same location. Once a first suture is deployed, the motion of suture deployment control mechanism 1143 is stopped and the surgeon need to reset (or move) suture number selection mechanism 1145 such that another suture may be deployed. Suture number selection mechanism 1145 may be implemented in any suitable way as long as it provides a functionality that only one suture may be deployed at a time, after which suture number selection mechanism 1145 is moved, rotated, or reset to allow for the next suture to be deployed. In an example embodiment, as shown in FIGS. 11E and 11F, suture number selection mechanism 1145 include portions 1145A and 1145B having protrusions, such as 1145C and 1145D. In an example embodiment, protrusions 1145C, 1145D, and the like may be coupled to element 1145E, such that portions 1145A and 1145B are bound to handle element 1146, but are configured to move through slots 1145F stopping at each step 1145G. To continue the motion to the next one of steps 1145G, portions 1145A and 1145B may need to be rotated around an axis of handle element 1146 by a target discrete amount. If portions 1145A and 1145B are not rotated by the target (e.g., maximum) discrete amount, movement of portions 1145A and 1145B towards a proximal end of device 1100 is prevented, thus preventing the movement of suture deployment control mechanism 1143, drive element 1163, and attached to them the suture deployment elements (e.g., shaft 731 and suture advancement/retraction element).

Figure 12:
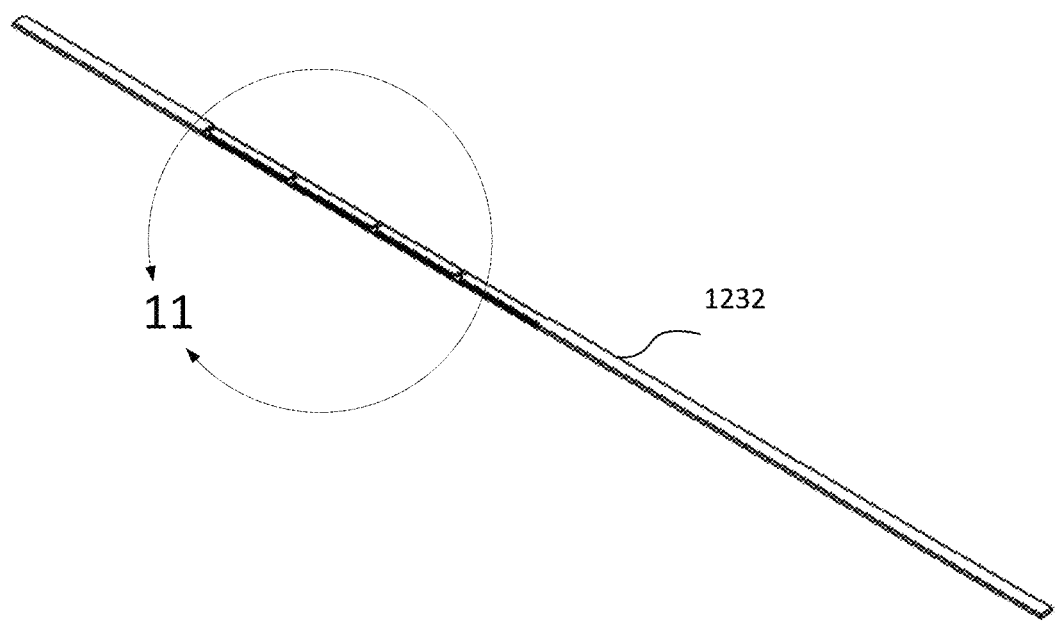
FIG. 12 is a perspective view of a suture advancement and retraction element of a suture delivery system, according to an embodiment.
Figure 13:
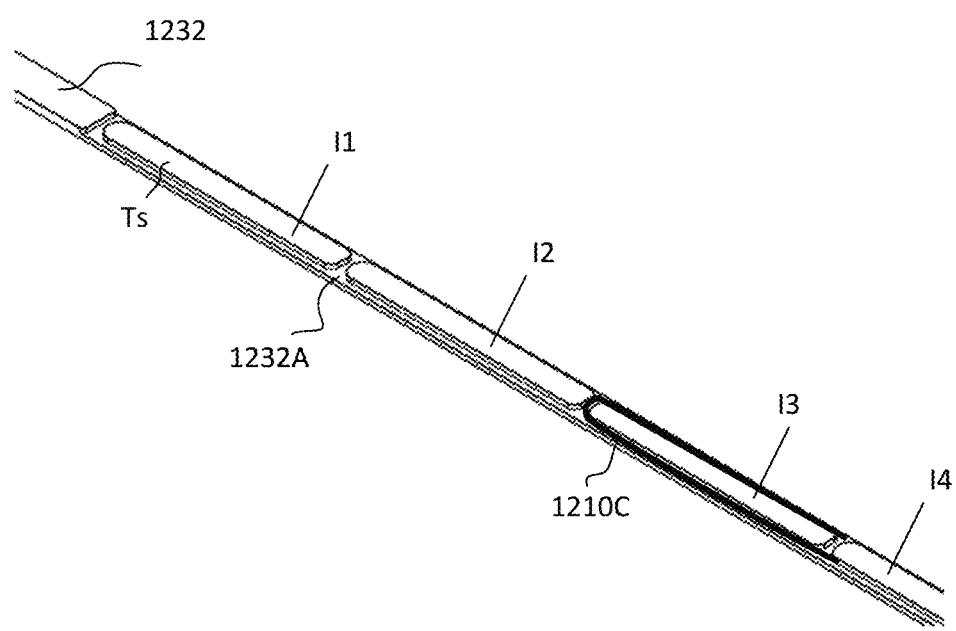
FIG. 13 is a detailed view of a distal portion of a suture advancement and retraction element of a suture delivery system, according to an embodiment.
Figure 18:
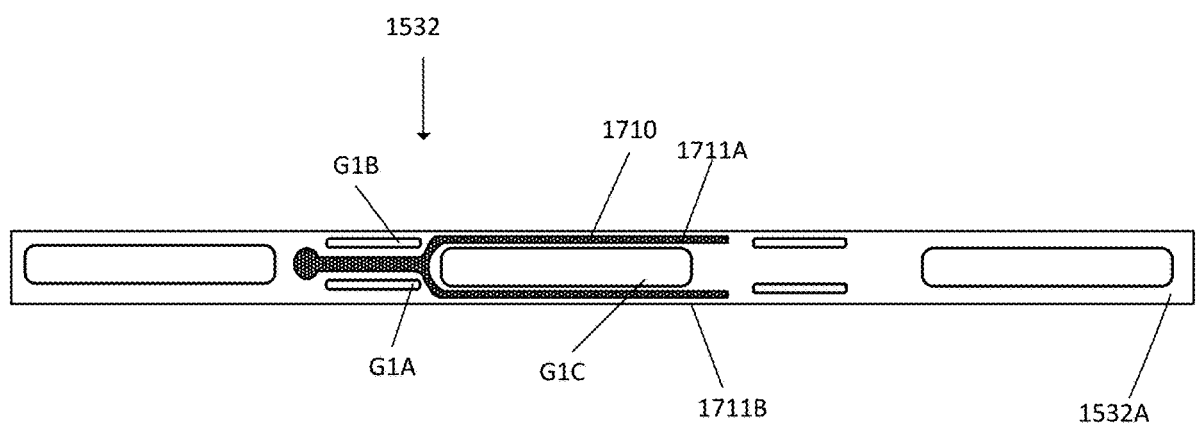
FIG. 18 is an example of a suture advancement and retraction element with a suture disposed thereon, according to embodiments.

FIGS. 12-13 and 15-16 show various example suture advancement/retraction elements configured to support various respective sutures shown in FIGS. 14A-14C, 17A-17C. Such suture advancement/retraction elements can be functionally and/or structurally similar to other suture advancement/retraction elements described herein (e.g., suture advancement/retraction element 132, 232). Further FIG. 18, shows an embodiment of suture advancement/retraction element with an example suture placed over the element. Consistent with disclosed embodiments, a SARE 1232 is shown in FIGS. 12 and 13. SARE 1232 is in an elongate structure having a ribbon-like shape (e.g., a shape with a rectangular cross-section or other cross-section where a first lateral dimension is greater than a second lateral dimension such that the elongate structure has a flattened shape). In various embodiments, the shape of SARE 1232 is configured such that it fits within an associated suture housing, which, in an example embodiment, defines a lumen having a rectangular cross-sectional area.

FIG. 13 shows a SARE 1232 implemented as a sled or ribbon-like structure that includes a set of protrusions or formations 11-14. In an example embodiment, a top surface Ts of a protrusion is configured to be adjacent to or near the internal surface of the top side of the suture housing. In an example embodiment, protrusions 11-14 are separated by a suture holding indented region 1232A. SARE 1232 is configured to support U-shaped sutures (e.g., sutures that do not include a tail region, such as tail region 414, as shown in FIG. 4). U-shaped sutures may be placed adjacent to protrusions 11-14. An example U-shaped suture 1210C placed in indented region 1232A adjacent to protrusion 13 is shown in FIG. 13. In various embodiments, suture 1210C is flattened when SARE 1232 is located within a suture housing, as suture 1210C may not have any room to expand. For example, legs of suture 1210C can be radially constrained between a formation 13 and an inner surface of suture housing such that the legs of suture 1210C are constrained along their entire length. Such constraining can prevent the legs of the suture 1210C from twisting undesirably and maintain the legs of the suture 1210C such that they extend parallel to one another. In other words, suture 1210C can be constrained between SARE 1232 and the internal surface of the suture housing and have no place to expand. As such, it remains flattened until at least a portion of suture 1210C reaches a deployment window within the suture housing. Once suture 1210C reaches the deployment window, a portion of suture 1210C may exit through the deployment window, and suture 1210C may curve in a controlled manner. For example, the suture 1210C can exit the deployment window substantially normal to a plane of the deployment window (e.g., angled between about 70 degrees and 110 degrees, including all subranges and values, from the deployment window).

Figure 14A:
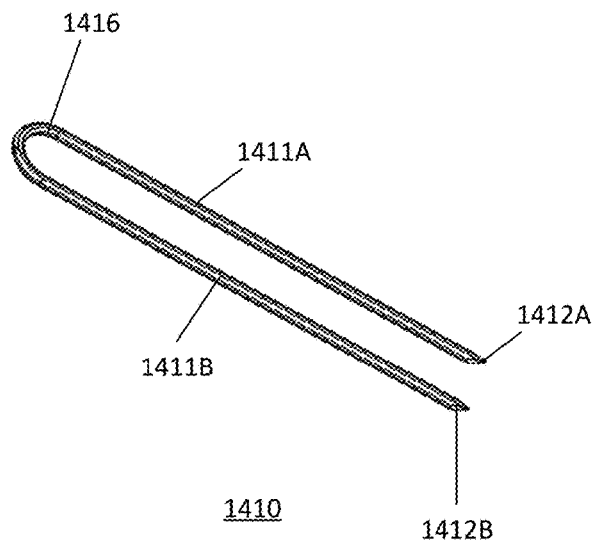
FIGS. 14A-14C are different views of an example suture that can be used with the suture advancement and retraction element depicted in FIGS. 12-13, according to an embodiment.
Figure 14B:
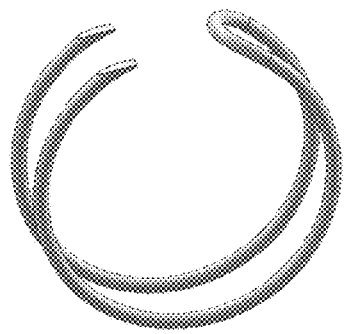
Figure 14C:
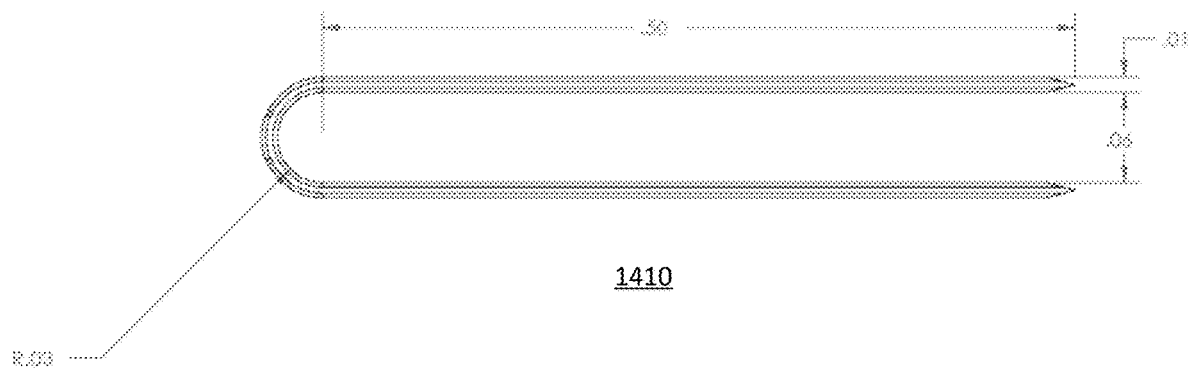

An example of a "U-shaped" suture 1410 is shown in FIG. 14A-14C. In an example embodiment, suture 1410 may be the same as suture 1210C, as shown in FIG. 13. Suture 1410 has prongs 1411A and 1411B having respective sharp ends 1412A and 1412B configured to penetrate tissue. In an example embodiment, prongs 1411A and 1411B are connected by a connecting element 1416 or connected at their proximal ends. FIG. 14A shows a flattened view of suture 1410 and FIG. 14B shows a curled suture 1410 (e.g., suture 1410 may acquire the curled shape when no external forces are acting on suture 1410).

FIG. 14C shows an example illustrative dimensions for suture 1410. In an example embodiment, the length of prongs 1411A and 1411B may be in a range of about a few tenths of an inch (e.g., in a range of about 0.1 inches to about 1 inches, including all sub-ranges and values therebetween). In an example embodiment, the length of prongs 1411A and 1411B may be about 0.5 inches. In various embodiments the distance between prongs 1411A and 1411B may also be in a range of about a few hundredth of an inch to a few tenth of an inch (e.g., in a range of about 0.01 inches to about 0.2 inches, including all sub-ranges and values therebetween). In an example embodiment, the distance between prongs 1411A and 1411B may have a value of about 0.06 inches.

In an example embodiment, connecting element 1416 may have a substantially constant curvature (e.g., connecting element 1416 may be in a shape of a half of a circle). Alternatively, connecting element 1416 may have any suitable shape. In an example embodiment, suture 1410 may not have sharp corners anywhere along the length of suture 1410. In an example embodiment, when connecting element 1416 has substantially constant curvature, a radius of curvature for connecting element 1416 may be half a distance between prongs 1411A and 1411B (e.g., as shown in FIG. 14C, if the distance between prongs 1411A and 1411B is about 0.06 inches, the radius of curvature may be about 0.03 inches). In various embodiments, a width (otherwise referred to as thickness) of prongs 1411A and 1411B may be a fraction of an inch (e.g., may be in a range of about 0.01-0.05 inches). In various embodiment, the size, shape, and thickness of suture 1410 are selected based on a type of tissue that needs to be sutured. For example, for a thicker tissue, larger sutures may be selected, and for a thinner, gentler tissue, smaller sutures may be selected. In various embodiments, a suture advancement/retraction element is selected based on a type (e.g., size, shape, and thickness) of sutures that need to be used for the surgical procedure. In various embodiments, values for the thickness of prongs 1411A and 1411B, and for the radius of curvature for connecting element 1416, may vary by as much as about 50% from the possible values described above.

Figure 15:
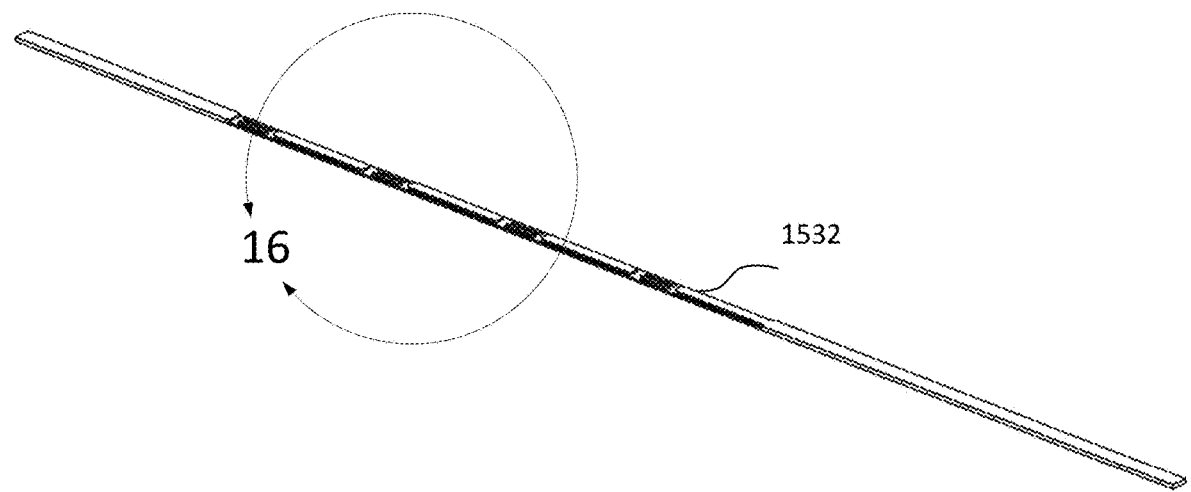
FIG. 15 is a perspective view of a suture advancement and retraction element of a suture delivery system, according to an embodiment.
Figure 16:
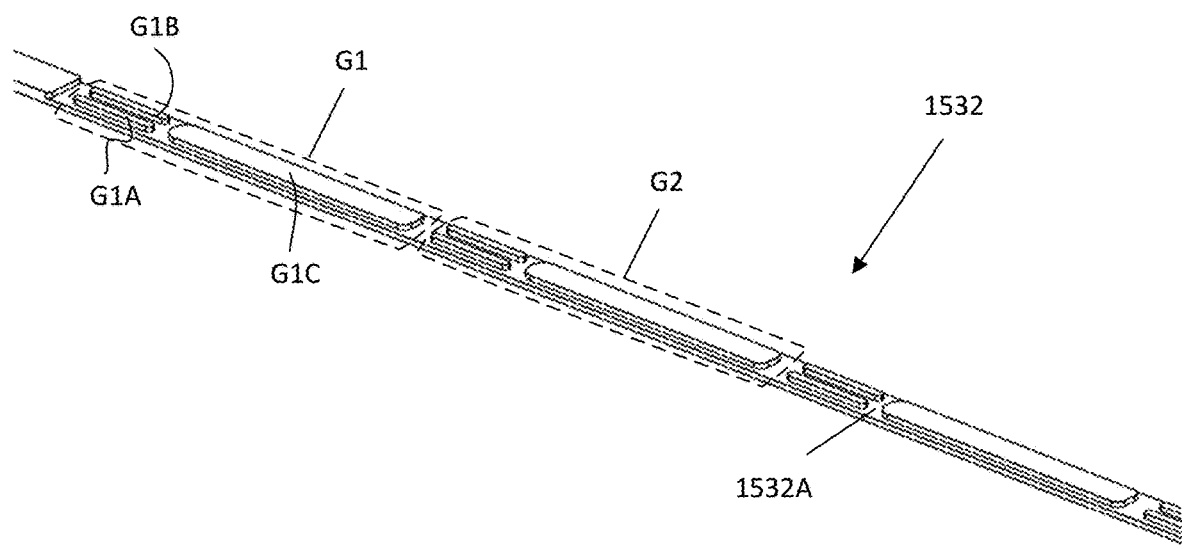
FIG. 16 is a detailed view of a distal portion of a suture advancement and retraction element of a suture delivery system, according to an embodiment.

Consistent with disclosed embodiments, a SARE 1532 is shown in FIGS. 15 and 16. Similar to SARE 1232, SARE 1532 is substantially an elongated rectangular prism. FIG. 16 shows that SARE 1532 includes a set of groups G1, G2, and so on, of protrusions, each group containing a first set of protrusions (e.g., G1A and G1B) and a second protrusion G1C. In an example embodiment, protrusions are placed over an indented region 1532A. In an example embodiment, top surfaces of protrusions G1A, G1B, and G1C are configured to be adjacent to or near the internal surface of the top side of a suture housing.

SARE 1532 is configured to support sutures containing tails (e.g., sutures that include a tail region, such as tail region 414, as shown in FIG. 4). An example suture may be placed over a surface of indented region 1532A, adjacent to protrusions G1A, G1B, and G1C. In various embodiments, a suture placed over the surface of indented region 1532A is flattened when SARE 1532 is located within a suture housing, as the suture may not have any room to expand and curl.

FIG. 17A shows an example embodiment of a suture containing a tail region 1714. Similar to suture 1410, suture 1710 has prongs 1711A and 1711B having respective sharp ends 1712A and 1712B configured to penetrate tissue. In an example embodiment, prongs 1711A and 1711B are connected by a connecting to tail region 1714. FIG. 17A shows a flattened view of suture 1710 and FIG. 17B shows a curled suture 1710 (e.g., suture 1710 may curl after being released from a suture housing). In an example embodiment, suture 1710 curls in a substantially circular shape, with a diameter 1727 having a value of about 0.16 inches. In an example embodiment, diameter 1727 may vary by as much as about 50% from the above value. FIG. 17C shows an example illustrative dimension for suture 1710. In an example embodiment, the length of prongs 1711A and 1711B may be in a range of about a few tenths of an inch (e.g., in a range of about 0.1 inches to about 1 inch, including all sub-ranges and values therebetween). In an example embodiment, the length of prongs 1711A and 1711B may have a value of about 0.5 inches. In various embodiments the distance between prongs 1711A and 1711B may also be in a range of about a few hundredth of an inch to a few tenth of an inch (e.g., in a range of about 0.01 inches to about 0.2 inches, including all sub-ranges and values therebetween). In an example embodiment, the distance between prongs 1711A and 1711B may have a value of about 0.06 inches.

In an example embodiment, tail region 1714 may have a length in a range of a few tenths of an inch and may be connected to prongs 1711A and 1711B via a connecting element 1716. Connecting element 1716 may be similar to connecting element 1416, as shown in FIG. 14A-14C, and may have the same or similar values for a radius of curvature. In various embodiments, a width of prongs 1711A and 1711B may be a fraction of an inch (e.g., may be in a range of 0.01-0.05 inches). In various embodiment, the size, shape, and thickness of suture 1710 are selected based on a type of tissue that needs to be sutured. For example, for a thicker tissue, larger sutures may be selected and for a thinner, gentler tissues, smaller sutures may be selected. In various embodiments, values for the thickness of prongs 1711A and 1711B, and for the radius of curvature for connecting element 1716, may vary by as much as about 50% from the possible values for these elements, as described above.

In various embodiments, a suture advancement/retraction element is selected based on a type (e.g., size, shape, and thickness) of sutures that need to be used for the surgical procedure.

In various embodiments, suture 1710 may be laser cut from a suitable sheet or tube of a material (e.g., nitinol, plastic, stainless steel, and the like).

FIG. 18 depicts an example of SARE 1532 implemented as a sled or ribbon-like structure with suture 1710 placed over a portion of a surface of SARE 1532 (e.g., suture 1710 is placed over surface 1532A) adjacent to protrusions or formations G1A, G1B, and G1C. The formations G1A, G1B, and G1C can include two smaller formations G1A and G1B that are configured to radially surround a portion of a tail of the suture 1710 and a larger formation G1C that is disposed between legs 1711A and 1711B of suture 1710. When the SARE 1532 is placed within a suture housing, the formation G1C can radially bound an inside of the legs 1711A and 1711B, while an outside of the legs 1711A and 1711B can be bound by an inner surface of the suture housing such that the formation and the suture housing collectively constrain the legs 1711A and 1711B of the suture in a radial direction. Such radial constraining can prevent twisting of the legs 1711A and 1711B of the suture and ensure that the legs 1711A and 1711B of the suture remain parallel to one another. When the suture then exits a deployment window of the housing, the legs 1711A and 1711B of the suture can be configured to exit parallel to one another and at an angle that is substantially normal relative to a plane of the window (e.g., at an angle of between about 70 degrees and about 110 degrees, including all subranges and values, relative to the window).

Figure 19A:
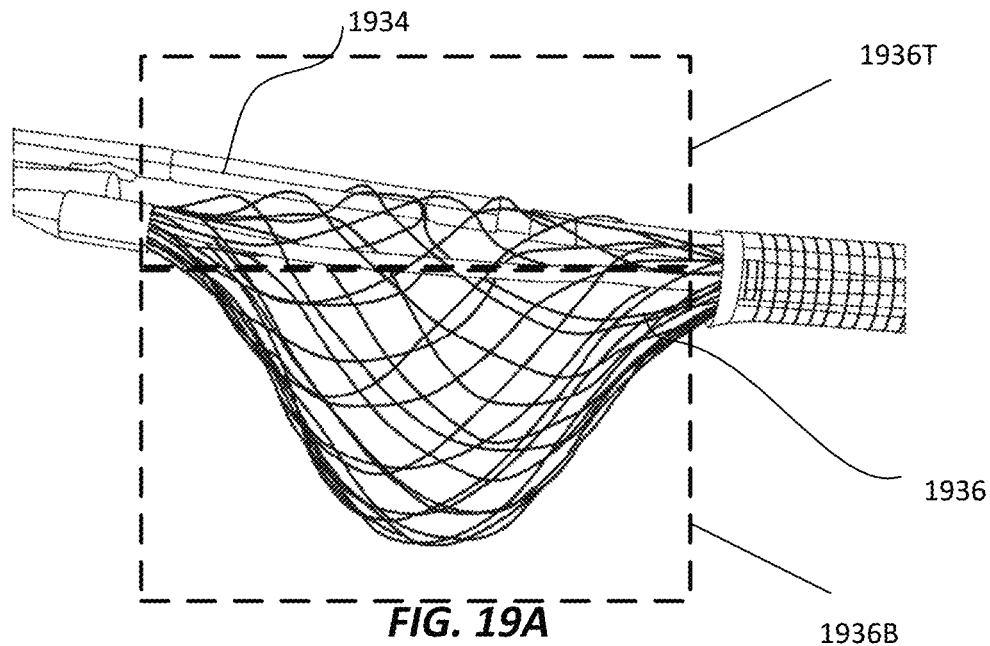
FIGS. 19A-19B are views of a biasing mechanism of a suture delivery system, according to an embodiment.
Figure 19B:
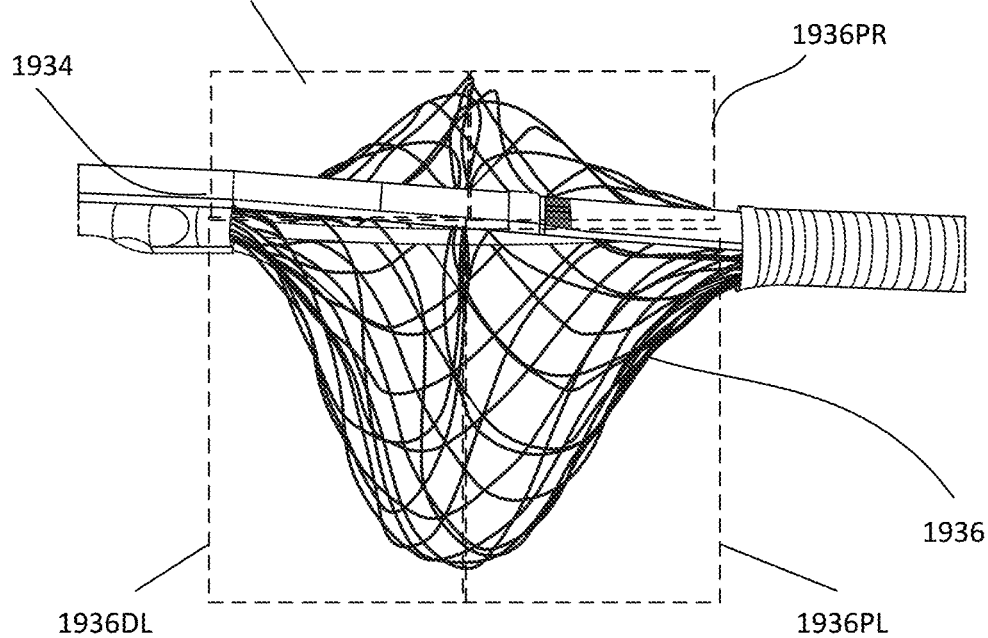

FIGS. 19A and 19B show views of a biasing mechanism 1936 and a suture housing 1934, according to embodiments. Biasing mechanism 1936 and suture housing 1934 can be structurally and/or functionally similar to other biasing mechanisms and suture housings described herein, respectively (e.g. biasing mechanism 136 and suture housing 134). FIG. 19A shows a side view of a catheter assembly 1930, including biasing mechanism 1936 and suture housing 1934 and FIG. 19B shows a substantially top view of catheter assembly 1930. FIG. 19A shows that a top portion 1936T of biasing mechanism 1936 may have a different shape than a bottom portion 1936B, thus resulting in top-to-bottom asymmetry of biasing mechanism 1936. Further, biasing mechanism 1936 may also be asymmetric along a distal-to-proximal direction and along left-to-right side direction of biasing mechanism 1936. For example, FIG. 19B shows that a distal left side 1936DL is different from a distal right side 1936DR of biasing mechanism 1936 and that both sides 1936DR and 1936DL are respectively different from proximal left side 1936PL and proximal right side 1936PR. In an example embodiment, side 1936DL may expand less than side 1936PL, and side 1936DR may expand less than side 1936DL or side 1936PL. It should be noted that any other asymmetries may be used. In some cases, depending on a specific surgical procedure, a biasing mechanism with a particular type of asymmetry may be selected.

Figure 19C:
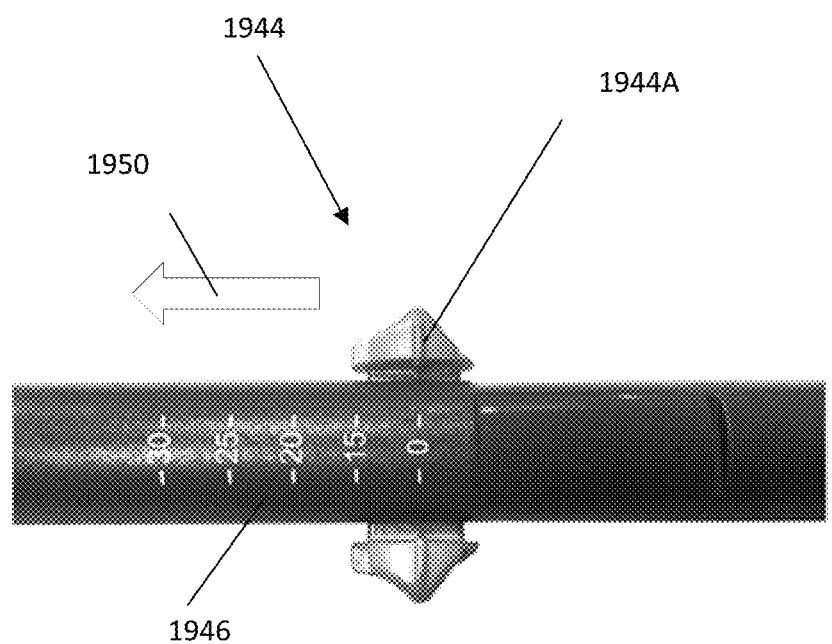
FIG. 19C depicts an example of a biasing mechanism actuator of a suture delivery system, according to an embodiment.

FIG. 19C shows an example embodiment of a biasing mechanism actuator 1944. Biasing mechanism actuator 1944 may include a slider element 1944A configured to slide in a direction shown by arrow 1950 along a handle element 1946. Handle element 1946 may include markings (e.g., 0, 5, 10, 15, 20, 25, 30) indicating how far slider element 1944A is moved along handle element 1946. In an example embodiment, as described above, a distance traveled by slider element 1944A indicates how much biasing element 1936 is expanded. For example, if slider element 1944A is at a mark 30, biasing element 1936 may be fully expanded, and if slider element 1944A is at a mark 0, biasing element 1936 may be fully contracted.

Figure 20A:
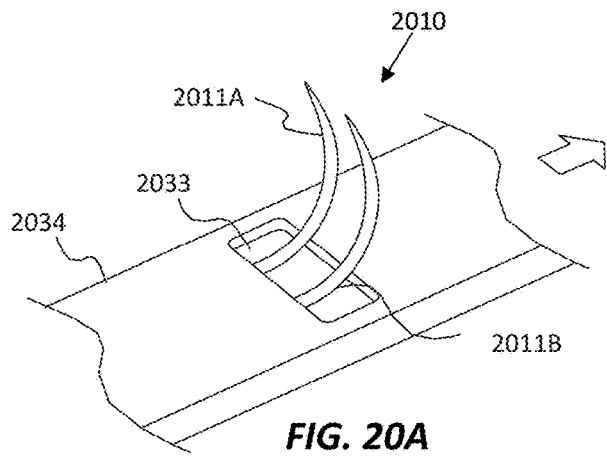
FIGS. 20A-20F depict a progression of releasing a suture from a suture delivery system where the suture is released from a side of the system, according to an embodiment.
Figure 20B:
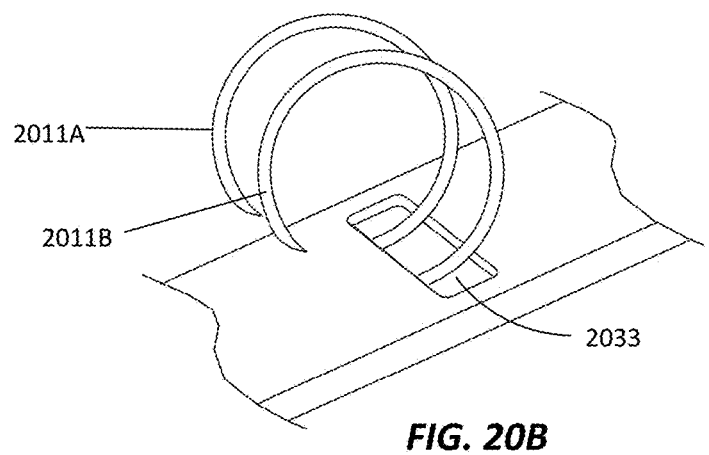
Figure 20C:
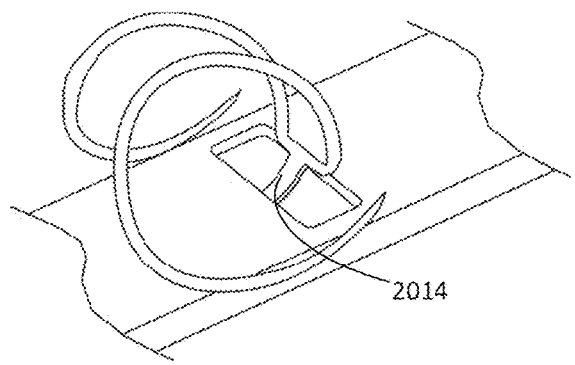
Figure 20D:
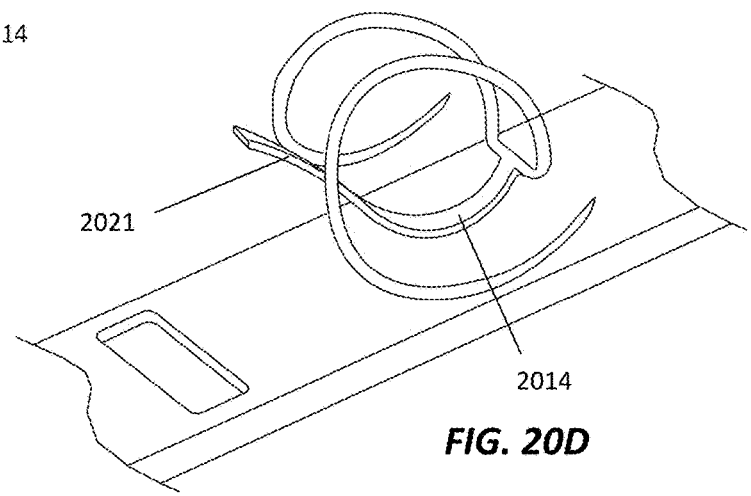

FIGS. 20A-20F indicate various steps (or stages) of deployment of a suture consistent with disclosed embodiments. At a first step, as shown in FIG. 20A prongs 2012A and 12012B of suture 2010 are configured to deploy through a deployment window 2033 of a suture housing 2034. In an example embodiment, SARE 2032 is pulled in a direction as indicated by arrow 2020. FIG. 2013 shows a second step, at which prongs 2012A and 2012B are substantially deployed, FIG. 20C shows a third step at which deployment of prongs 2012A and 2012B is complete, and a tail region 2014 may need to be deployed. At a fourth step, as shown in FIG. 20D, tail region 2014 is deployed. A tail end 2021 may be configured to push against a tissue (not shown in FIG. 20D) such that suture 2010 is well bound to the graft and tissues which it is suturing.

Figure 20E:
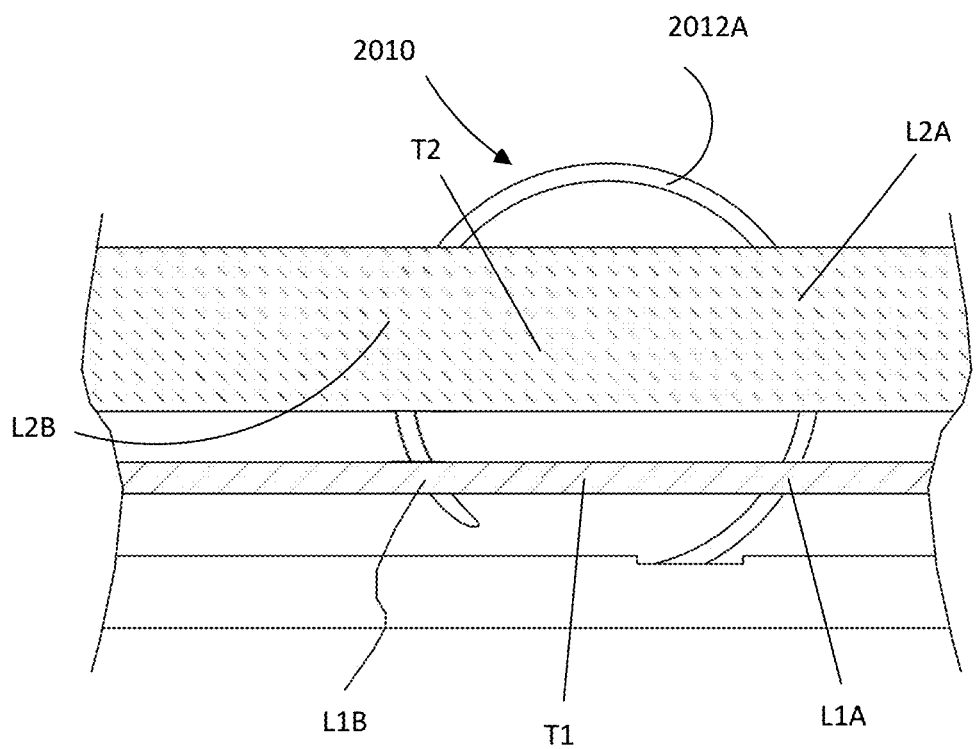
Figure 20F:
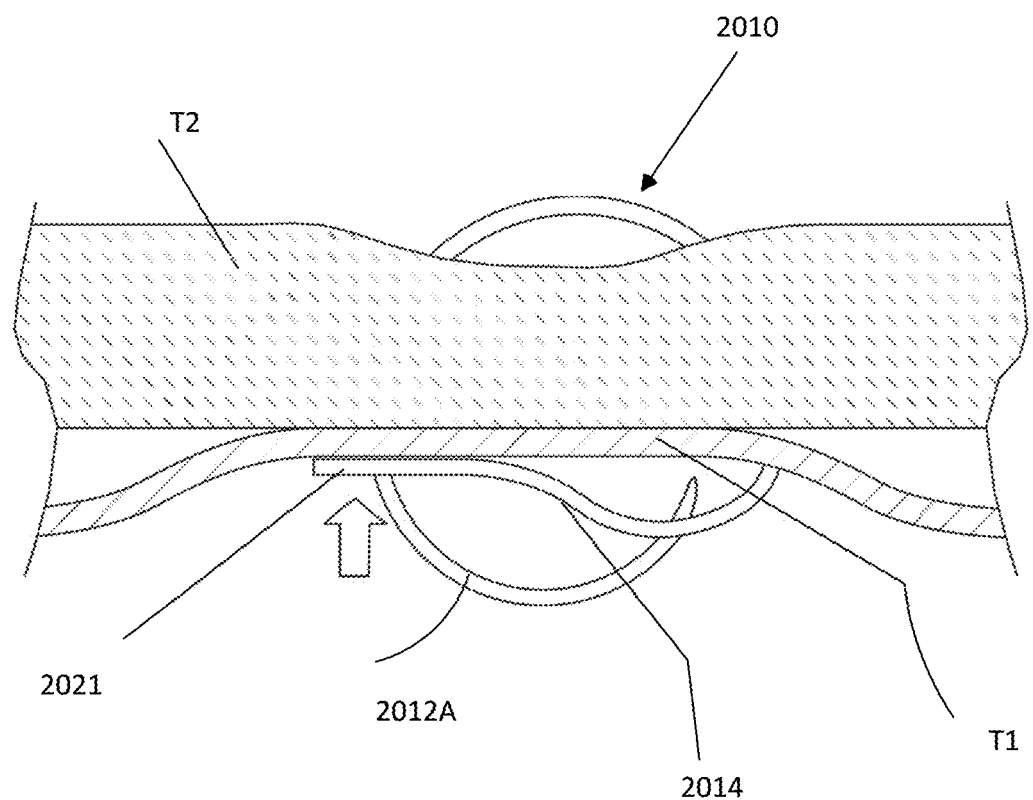

FIGS. 20E and 20F show suture 2010 penetrating and binding materials and/or tissues T1 and T2. For purposes of illustration, FIGS. 20E and 20F depict certain dimensions of suture 2010 and materials and/or tissues T1 and T2 that facilitate describing the clamping effect of suture 2010 on materials and/or tissues T1 and T2. Nevertheless, it can be appreciated that in practical applications, the dimensions of suture 2010 and materials and/or tissues T1 and T2 may be significantly different, e.g., where materials and/or tissues T1 and T2 are thicker than shown and suture 2010 is configured to be buried in materials and/or tissues T1 and T2. As such, it should be noted that the suture 2010 and materials and/or tissues T1 and T2 depicted in FIGS. 20E and 20F may not be drawn to scale. In an example embodiment, as shown in FIG. 20E, a prong (e.g., prong 2012A) of suture 2010 is configured to penetrate tissue T1 at a location L1A, penetrate tissue T2 at a location L2A, and then, due to curling of suture 2010, penetrate again tissue T2 at a location L2B, and penetrate again tissue T1 at a location L1B. Upon complete release of suture 1210, as shown in FIG. 20F, tail region 2014 is configured to press on tissue T1, using tail end 2021. By pressing with tail end 2021, suture 2010 is configured to improve binding between tissue T1 and T2.

While embodiments for deployment sutures use a deployment window (e.g., deployment window 733, as shown in FIG. 8B) located at a side of a suture housing (e.g., suture housing 734, as shown in FIG. 8B), other configurations of suture housings and deployment windows are possible. In one example embodiment, as shown in FIGS. 21A-21C, a suture housing 2134 may not be configured to be connected to an introducer tip (e.g., introducer tip 738, as shown in FIG. 7B) but may have an end with a deployment window 2133 located at that end. In an example embodiment, such suture housing 2134 (and a catheter assembly using suture housing 2134) may be used for delivering sutures to a zone that is substantially perpendicular to a direction of catheter assembly. FIG. 21A shows suture housing 2134 with SAKE 2132 moving towards T1 and T2 tissues and having suture 2110 approaching tissues T1 and T2. FIG. 21B shows suture 2110 penetrating tissue T1 and T2 as it is being deployed from deployment window 2133, and FIG. 21C shows suture 2110 being fully deployed and binding tissues T1 and T2.

FIG. 22 shows another example catheter assembly 2230 with suture housing 2234 having a deployment window 2233 at the end of suture housing 2234. In an example embodiment, sutures are deployed from deployment window 2233. In some cases, suture housing 2234 is configured to bend in a prescribed direction by a target angular amount (e.g., suture housing 2234 may bend by an angle ranging, for example, from 0 degrees to 45 degrees).

FIG. 23 shows another embodiment of catheter assembly 2330 with a suture housing 2334 capable of bending. In an example embodiment, suture housing 2334 has one or more deployment windows 2333A-2333C located on a side of suture housing 2334. In an example embodiment, suture housing 2334 could be delivered perpendicular to a surface of a tissue that needs to be sutured. Subsequently, a suitable shaping wire could be placed to create a curve for suture housing 2334. Alternatively, suture housing 2334 may be fabricated pre-curved, and a straightening wire (e.g., the wire that can straighten suture housing 2334) may temporarily be inserted along suture housing 2334 during placement of suture housing 2334. The straightening wire may be removed during a delivery of a suture, thus resulting in curved suture housing 2334. FIG. 24 shows an example of suture housing 2434 that is partially curved, and which has a deployment window 2433 on a side of suture housing 2434.

FIGS. 25A-25B, and 26A-26B show examples of sutures 2510 that are chained or connected together by a suitable flexible connecting element 2517 (e.g., a flexible wire or a flexible string). In an example embodiment, sutures 2510 may be connected, pre-loaded onto a SARE, and placed in a suture housing. In an example embodiment, the SARE may be configured to have a space to accommodate connection element 2517 between sutures 2510. Using linked sutures allows for adjusting a tension between sutures if such adjustment is needed. Such adjustment can be used to provide a means to change a tissue feature, such as an ostium of an artery, a wound, or other tissue feature or malignancy that needs to be treated. As shown in FIG. 25B, and as previously described, suture 2510 may include an opening 2515 through which connecting element 2517 may be placed.

FIGS. 26A and 26B show connecting element 2617 that may be formed from the same material as sutures 2610. In an example embodiment, connecting element 2617 and sutures 2610 may be fabricated from the same material (e.g., by laser cutting a sheet or a tube of a material such as nitinol, stainless steel, or a suitable plastic). In an example embodiment, connecting element 2617 may provide a pre-formed tension (e.g., the nitinol link may have a pre-formed tension) in order to provide tension to the tissues of a patient. In an example embodiment, connecting element 2617 may change shape (i.e., curl) when released from a suture housing. FIG. 26B shows that sutures may be prearranged to form complex shapes (e.g., three sutures may be prearranged to form a semi-circle) instead of being linearly placed on a SARE.

Figure 27A:
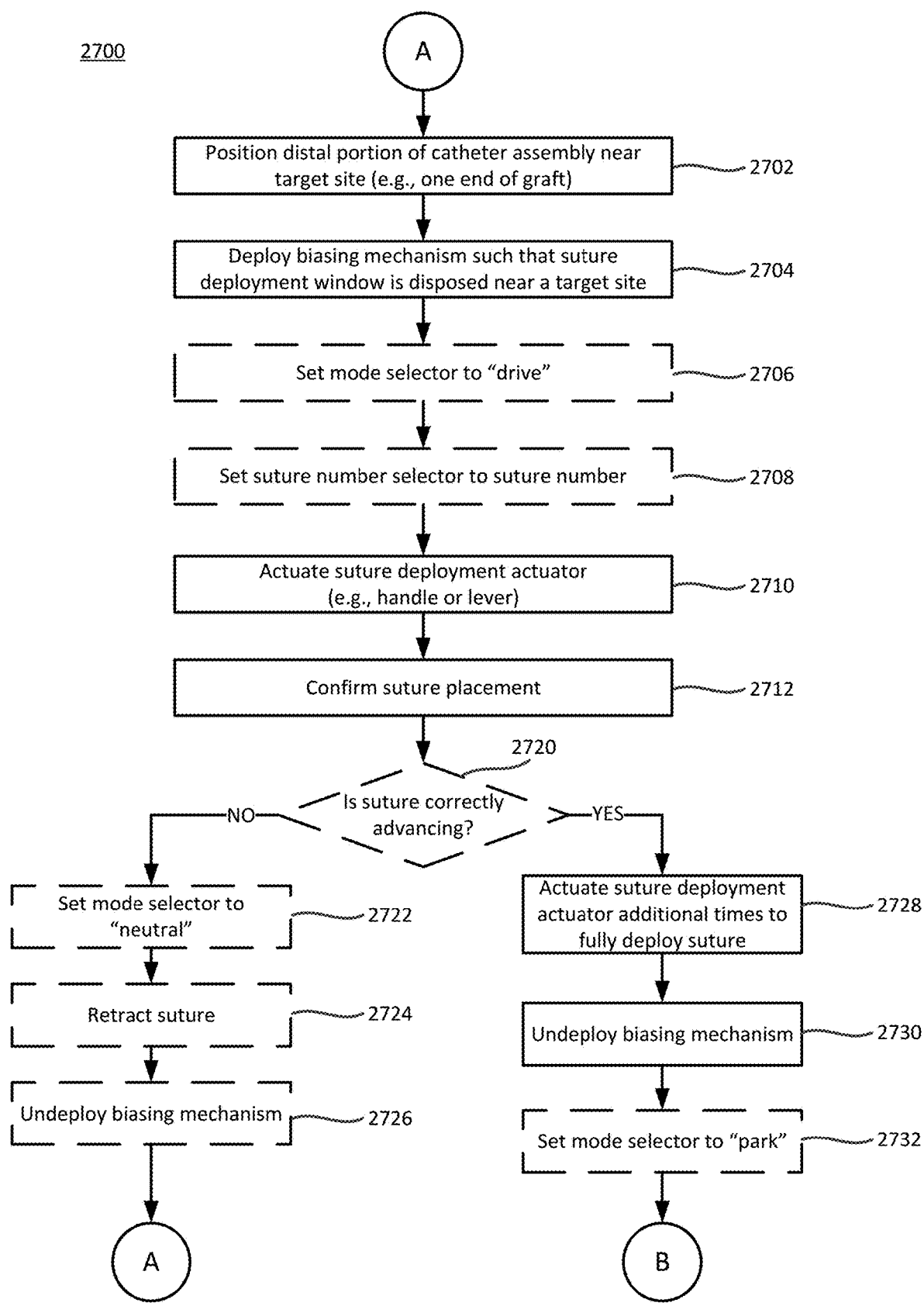
FIGS. 27A-27B are flow charts of an example process for placing a suture, according to an embodiment.

FIG. 27A shows an example process 2700 of deploying sutures consistent with a disclosed embodiment. At step 2702 of process 2700, a distal portion of a catheter assembly is positioned near a target site (e.g., near a wall of a graft, or a surface of a tissue that requires suturing). At step 2704, a device for deploying sutures (e.g., device 700, as shown in FIG. 7A) is manipulated (e.g., by a surgeon) to deploy a biasing mechanism such that a suture deployment window located in suture housing is disposed near a target site. The biasing mechanism is configured to expand within a cavity in which the catheter assembly is placed, and is configured to press at least a portion of the suture housing, having the suture deployment window, to a surface of a tissue (e.g., a graft, an aorta, and the like) that requires suturing. At step 2706, a surgeon operating the device is configured to set a mode selector of a mode selection system to "drive" (mode "D") as described above. At step 2708, the surgeon is configured to set a suture number selection mechanism to a particular suture number to deploy a particular suture, as described above, and at step 2710, actuate a suture deployment actuator by manipulating a suture deployment control mechanism (e.g., handle or lever) to initiate deployment of a suture. In an example embodiment, after partially deploying the suture, the surgeon may confirm a suture placement at step 2712. The confirmation for the suture placement may be accomplished using any suitable means (e.g., using imaging such as internal camera, CT scan, ultrasound, and the like, as described above).

If the suture is correctly placed (step 2720, Yes), at step 2728, the suture deployment actuator may be actuated several additional times (e.g., a suture deployment control mechanism 743, as shown in FIG. 9A, may be pressed several times) for the suture to be fully deployed. At step 2730, a biasing mechanism is undeployed (e.g., when the biasing mechanism is an expandable mesh, the mesh may be fully contracted). In an example embodiment, the biasing mechanism is undeployed by actuating a biasing mechanism actuator, as described above. At step 2732, the surgeon may set the mode selector into "park" mode ("P" mode) as described above. In park mode, the suture deployment control mechanism (e.g., the suture deployment control mechanism, as described above) is fixed, and no new sutures may be deployed.

If the suture is not correctly placed (step 2720, No), at step 2722 the surgeon may set the mode selector into "neutral" mode ("N" mode) as described above. By setting mode selector into the neutral configuration, the surgeon may slide a RARE (e.g., SARE 132) towards a distal end of device 700, and, as a result, at step 2724, retract the suture back into a suture housing, At step 2726, the surgeon may operate the suture delivery device and undeploy the biasing mechanism. Step 2726 may be the same as step 2730, as described above. After undeploying the biasing mechanism, the surgent may move a catheter assembly of a device (e.g., catheter assembly 730 of device 700) to a new site for performing suturing at that site. After moving to the new site, process 2700 may be repeated.

Figure 27B:
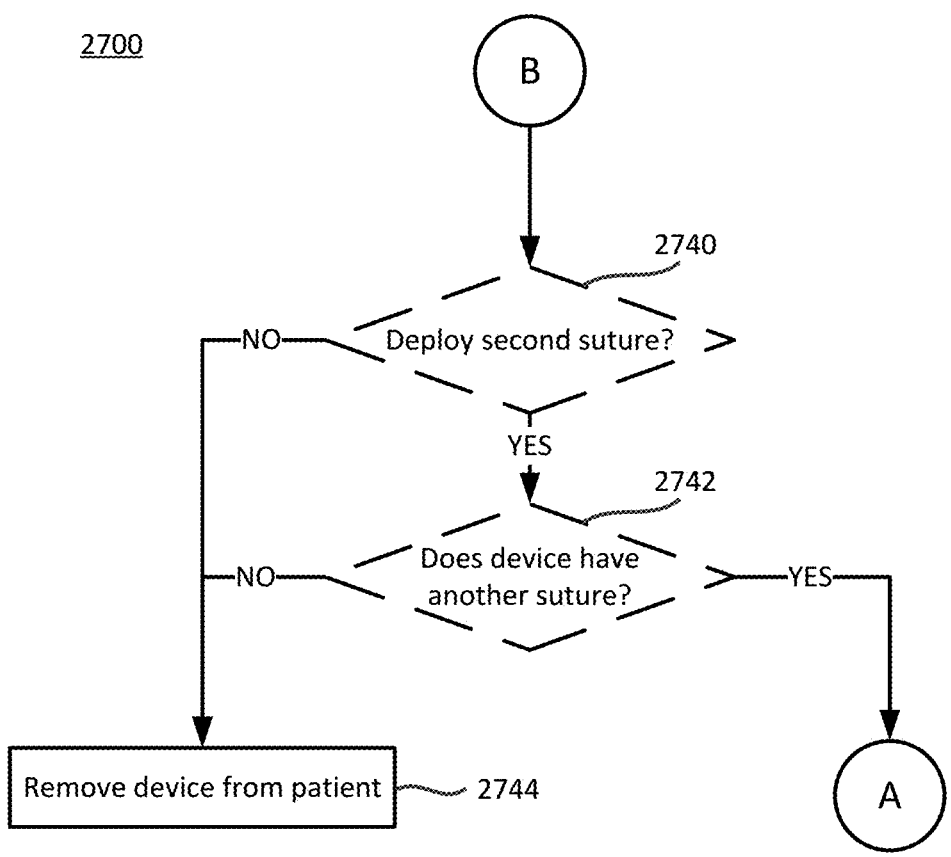

FIG. 27B shows a further set of steps of process 2700 that may be performed after step 2732. At step 2740, if a second suture needs to be deployed (step 2740, Yes), the surgeon may determine if SARE contains more sutures. If SARE contains more sutures (step 2742, Yes), process 2700 may be repeated starting with step 2702. Alternatively, if SARE does not contain more sutures (step 2742, No), at step 2744, catheter assembly 730 may be removed from a body of a patient (e.g., entire device 700 may be withdrawn, and, in some cases, be reloaded with a new catheter assembly, or a new SARE containing sutures may be changed). At step 2740, if a second suture does not need to be deployed (step 2740, No), step 2744 is performed as described above.

Figure 28A:
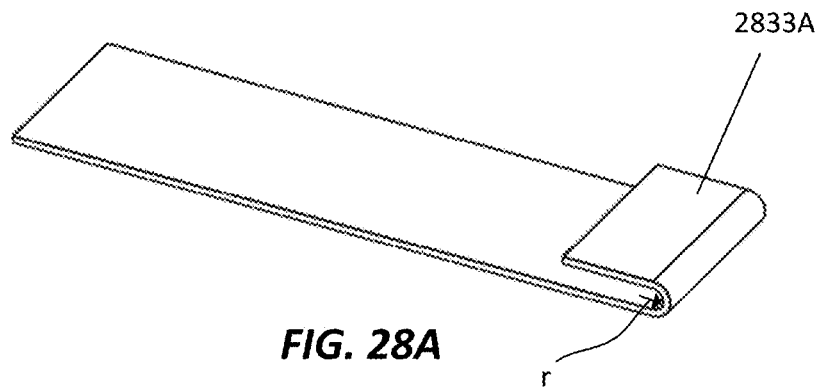
FIG. 28A-28C provide detailed view of a bearing element of a suture delivery system that is placed near a deployment window or opening of a suture housing, according to an embodiment.
Figure 28B:
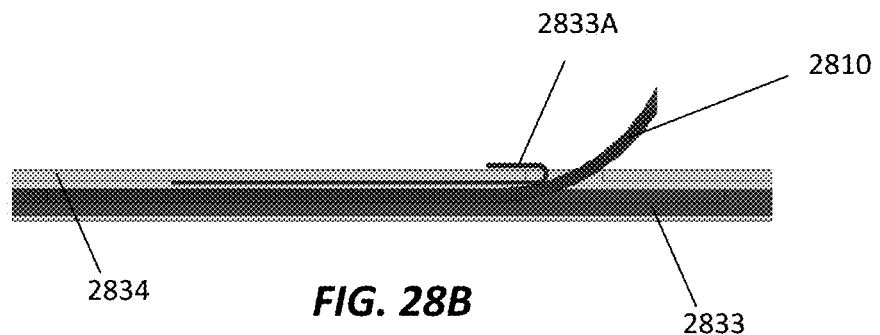
Figure 28C:
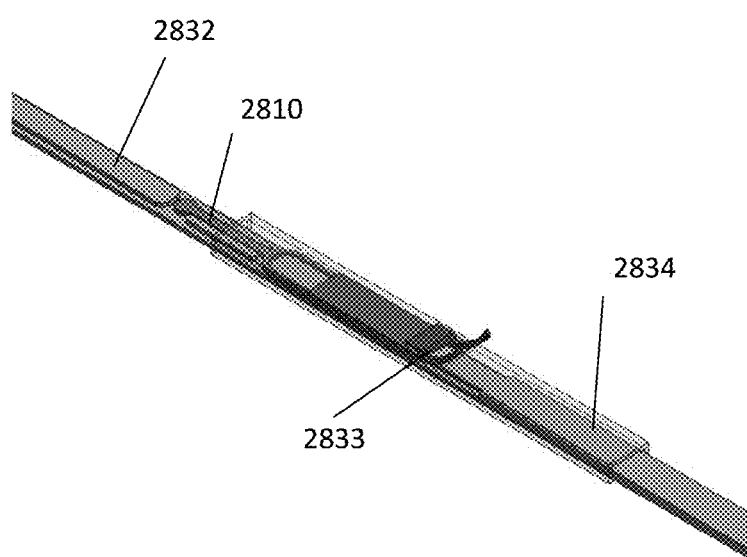

Suture housings described herein can be formed of flexible material (e.g., a flexible plastic) and therefore be susceptible to wear from sutures, which can be formed of harder (e.g., metallic material). As such, suture housing can include metallic bearings that can prevent or reduce wear along a length of the distal portions of the housings containing the sutures. For example, FIGS. 28A-28C show example views of an embodiment of a suture housing 2834 having a suture deployment window 2833. FIG. 28B shows that deployment window 2833 includes a lip element or bearing 2833A, configured to protect the suture housing 2834 in a region near the deployment window 2833 (e.g., from sharp ends of sutures) and/or smooth edges around deployment window 2833. Suture housing 2834 can be formed from a flexible material, such as a plastic (e.g., polyetheretherketone). Such material, however, can be susceptible to puncture or wearing as sutures are deployed from the device. As such, the bearing 2833A can be used to protect the inner surfaces of the suture housing 2834 where the sharpened ends of the sutures may reside and make contact with. In some embodiments, the bearing 2833A can extend through a longer length of the suture housing 2834, e.g., along an entire distal portion where the sutures are housed. In an example embodiment, as shown in FIG. 28A, lip element 2833A may be formed from a folded sheet of a suitable material (e.g., metal). In an example embodiment, a radius r, as shown in FIG. 28A is selected to ensure that a suture deployed via deployment window 2833 is released in a smooth and controlled way. Further, smooth lip element 2833A ensures that an edge around deployment window 2833 is sufficiently smooth and does not harm tissues in the proximity of window 2833. FIG. 28C shows an example embodiment, in which suture 2810 is deployed from deployment window 2833 of suture housing 2834.

Figure 29:
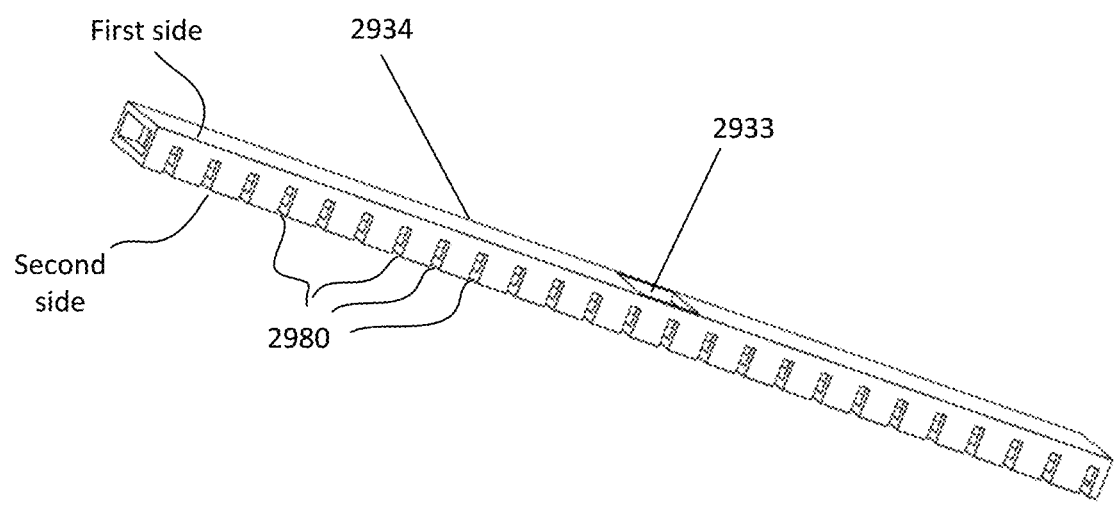
FIG. 29 depicts an example suture housing of a suture delivery system, according to an embodiment.

In some embodiments, it can be desirable to use a suture housing formed from a harder material, such as, for example, metal, e.g., to avoid wearing of the housing over time by suture advancement. Such suture housings, however, may be inflexible unless features are incorporated into such housings to increase their flexibility. For example, features such as openings, perforations, indentation, serrations, etc. can be added to increase flexibility of a suture housing. For example, FIG. 29 shows an example suture housing 2934 having a deployment window 2933 and openings 2980 (only some of the openings are labeled in FIG. 29). Openings 2980 do not impede a motion of SARE within suture housing 2934 and do not impede deployment of sutures. In an example embodiment, openings 2980 allow for improved flexibility of suture housing 2934. For example, suture housing 2934 with openings 2980 is more bendable than a similar suture housing (e.g., suture housing 734) without the openings. Suture housing 2934, for example, be formed of a rigid material such as a metal or metal composite, and therefore the openings 2980 can enable the suture housing 2934 to bend. The suture housing 2934 by being formed from the more rigid material, such as metal, can be capable of withstanding sharp ends of sutures without requiring a bearing (such as, for example, bearing 2833A). While are shown at a seconds side of suture housing 2934, in some cases, openings at a first side may be used as well to further increase the flexibility of suture housing 2934.

Figure 30:
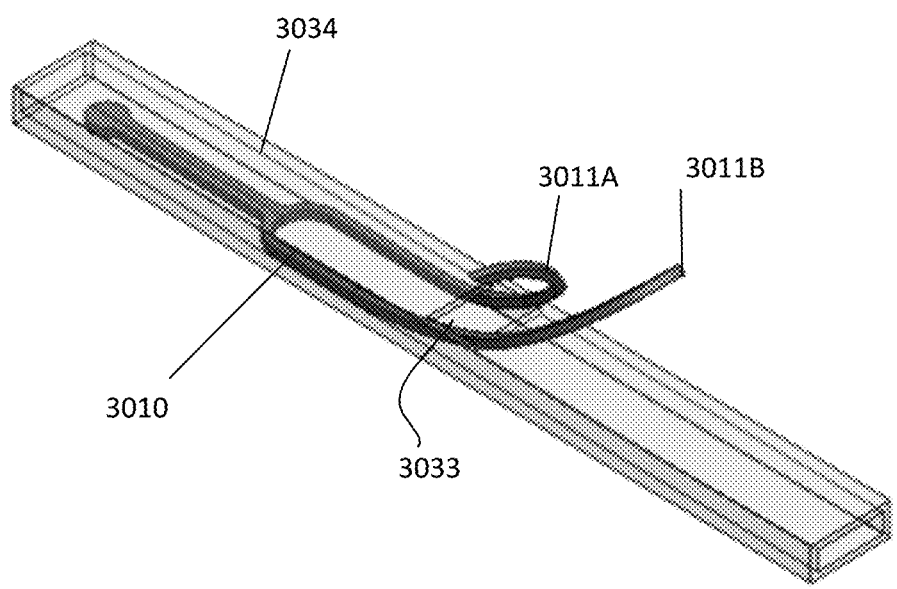
FIG. 30 depicts an example of a suture exiting a suture housing wrongly, according to an embodiment.

FIG. 30 shows an example embodiment, in which a suture 3010 is deployed ineffectively or mal-deployed from suture housing 3034 via deployment window 3033. In an example embodiment, suture 3010 includes prongs or legs 3011A and 3011B. In an example embodiment, suture 3010 may start changing shape (e.g., curling) as prongs 3011A and 3011B are being released from window 3033 because suture 3010 may not have been supported or constrained by a suture advancement/retraction mechanism or SARE, such as any of the ones described herein. For example, the SARE described herein can include formations that, together with the suture housing, can radially constrain the legs of a suture along their entire length and therefore prevent the legs from curling or twisting relative to one another and exiting the housing non-parallel to one another. Without the SARE, the suture 3010 may mal-deploy from the window, as depicted in FIG. 30. In particular, the suture 3010 can be formed of a superelastic material, as described above. The suture 3010, when constrained within the suture housing, is therefore in a high energy state. If the legs 3011A and 3011B of the suture 3010 are not constrained radially between a SARE and the suture housing, the high energy state of each suture leg when flattened would find a way to resolve to its natural condition using any free range of motion it is allowed. This can lead to suture legs exiting the suture deployment window at undesired angles and forms, such as shown in FIG. 30. Such deployment of the suture can lead to complications in placing the sutures.

It should be understood that the examples and illustrations in this disclosure serve exemplary purposes and departures and variations in shapes of elements (e.g., sutures), and operation of various components (e.g., operation of biasing member), may be varied according to the teachings herein without departing from the scope of this invention.

As used herein, the terms "about" and/or "approximately" and/or "substantially" when used in conjunction with numerical values and/or ranges generally refer to those numerical values and/or ranges near to a recited numerical value and/or range. In some instances, the terms "about" and "approximately" and "substantially" may mean within ±10% of the recited value. For example, in some instances, "about 100 [units]" may mean within ±10% of 100 (e.g., from 90 to 110). The terms "about" and "approximately" may be used interchangeably.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The invention claimed is:

1. A kit, comprising:
  a suture including:
    a set of legs;
    a bridging element coupled to the set of legs; and
    a tail coupled to the bridging element,
    the suture configured to transition from (1) a flattened configuration in which the tail extends in a proximal direction from the bridging element and the set of legs extends in a distal direction from the bridging element to (2) a curved configuration in which the tail and the set of legs are curved,
    the set of legs having distal ends that terminate in sharpened tips that are configured to penetrate through a portion of a graft and a vessel wall adjacent to the portion of the graft; and
  a suture delivery system including:
    a housing configured to contain the suture in the flattened configuration, the housing defining an opening for releasing the suture from an interior of the housing such that the suture can automatically transition from the flattened configuration into the curved configuration; and
    a deployment element having a distal portion slidably disposed in the housing, the distal portion of the deployment element having a surface configured to interface with the suture along an entire length of the suture, the deployment element including a set of formations on the distal portion of the deployment element, the set of formations defining first and second regions each for receiving a leg of the set of legs and a third region for receiving the tail of the suture,
    the housing and the deployment element configured to collectively constrain the suture in the flattened configuration until the suture is released through the opening of the housing, the deployment element slidable to release the suture from the opening of the housing.

2. The kit of claim 1, wherein the set of legs and the tail are configured to exert forces in opposite directions when the suture is in the curved configuration such that the set of legs and the tail are configured to hold the portion of the graft and the vessel wall relative to one another.

3. The kit of claim 1, wherein the sharpened tips of the suture are configured to curve and penetrate through the portion of the graft and the vessel wall while exiting from the opening of the housing.

4. The kit of claim 1, wherein the suture in the curved configuration is configured to form an annular loop, and at least a portion of the tail is configured to be disposed within the annular loop when the suture is in the curved configuration.

5. The kit of claim 1, wherein the set of formations includes a set of smaller ridges that extend parallel to one another and a larger ridge that is disposed proximal of the set of smaller ridges.

6. The kit of claim 5, wherein, when the suture is disposed within the housing and constrained at least partially by the distal portion of the deployment element, the set of two legs of the suture are disposed on opposite sides of the larger ridge and the tail of the suture is disposed between the set of smaller ridges.

7. The kit of claim 1, wherein the set of legs and the tail of the suture are configured to generate a clamping or tightening force when the suture is in the curved configuration.

8. The kit of claim 1, wherein the suture delivery system further includes an actuator configured to move the deployment element relative to the housing to release the suture from the opening of the housing,
  the deployment element having a distal end that is free-floating within the housing and a proximal end that is coupled to the actuator via an elongate shaft.

9. The kit of claim 8, wherein the elongate shaft is a first elongate shaft, the suture delivery system further including:
  a catheter defining a lumen; and
  a second elongate shaft coupled to an introducer tip, the first and second elongate shafts disposed concentrically within the lumen of the catheter.

10. The kit of claim 9, wherein the suture delivery system further includes:
a third elongate shaft; and
a biasing mechanism configured to expand to press the opening of the housing against a suture site, the biasing mechanism having a distal end coupled to the introducer tip and a proximal end coupled to the third elongate shaft,
the third elongate shaft disposed concentrically with the first and second elongate shafts within the lumen of the catheter.

11. The kit of claim 10, wherein the third elongate shaft can be moved relative to the introducer tip to expand the biasing mechanism.

12. The kit of claim 10, wherein, when the biasing mechanism is expanded, the actuator is configured to move the deployment element to release the suture from the opening of the housing such that the suture is directed through the portion of the graft and the vessel wall.

13. The kit of claim 10, wherein the suture delivery system further includes a locking mechanism configured to lock movement of the actuator until the biasing mechanism has been expanded.

14. The kit of claim 1, further comprising a biasing mechanism configured to expand to press the opening of the housing against a suture site.

15. The kit of claim 14, wherein the biasing mechanism when expanded forms an asymmetrical shape in which a first side of the biasing mechanism facing away from the housing is bowed outward while a second side of the biasing mechanism facing the housing is substantially flat.

16. The kit of claim 15, wherein the first side of the biasing mechanism is configured to bow out radially away from the housing up to about 270 degrees relative to a longitudinal axis of the elongate shaft.

17. The kit of claim 14, wherein the biasing element is formed of a plurality of braided wires.

18. The kit of claim 1, wherein the housing of the suture delivery system has a distal end that is coupled to an introducer tip and a proximal end that is disposed around the deployment element.

19. The kit of claim 1, wherein the housing of the suture delivery system includes a bearing material disposed inside the housing near the opening such that suture can slide along the bearing without damaging the housing when being released from the housing.

20. The kit of claim 1, wherein the distal portion of the deployment element has a ribbon-shaped structure.

21. A kit, comprising:
a suture including:
a set of legs having distal ends that terminate in sharpened tips that are configured to penetrate through a portion of a graft and a vessel wall adjacent to the portion of the graft; and
a tail coupled to the set of legs,
the suture configured to transition from (1) a flattened configuration in which the tail extends in a direction opposite to a direction of the set of legs to (2) a curved configuration in which the tail and the set of legs are curled in a substantially circular shape; and
a suture delivery system including:
a housing configured to contain the suture in the flattened configuration, the housing defining an opening for releasing the suture from an interior of the housing such that the suture can automatically transition from the flattened configuration into the curved configuration; and
a deployment element having a distal portion slidably disposed in the housing, the distal portion of the deployment element having a surface configured to interface with the suture along an entire length of the suture, the deployment element includes a set of formations on the distal portion of the deployment element, the set of formations defining first and second regions each for receiving a leg of the set of legs and a third region for receiving the tail of the suture,
the housing and the deployment element configured to collectively constrain the suture in the flattened configuration until the suture is released through the opening of the housing, the deployment element slidable to release the suture from the opening of the housing.

22. The kit of claim 21, wherein the tail of the suture is configured to be disposed between the set of legs of the suture when the suture is in the curved configuration.

23. The kit of claim 21, wherein the tail is configured to extend past the distal ends of the set of legs when the suture is in the curved configuration.

24. The kit of claim 21, wherein the set of legs and the tail are configured to exert forces in opposite directions when the suture is in the curved configuration such that the set of legs and the tail are configured to hold the portion of the graft and the vessel wall relative to one another.

25. The kit of claim 21, wherein the sharpened tips of the suture are configured to curve and penetrate through the portion of the graft and the vessel wall while exiting from the opening of the housing.

26. The kit of claim 21, wherein the set of formations includes a set of smaller ridges that extend parallel to one another and a larger ridge that is disposed proximal of the set of smaller ridges.

27. The kit of claim 26, wherein, when the suture is disposed within the housing and constrained at least partially by the distal portion of the deployment element, the set of two legs of the suture are disposed on opposite sides of the larger ridge and the tail of the suture is disposed between the set of smaller ridges.

28. The kit of claim 21, wherein the suture delivery system further includes an actuator configured to move the deployment element relative to the housing to release the suture from the opening of the housing, the deployment element having a distal end that is free-floating within the housing and a proximal end that is coupled to the actuator via an elongate shaft.

\* \* \* \* \*